(12) United States Patent
Fischer et al.

(10) Patent No.: US 8,410,289 B2
(45) Date of Patent: Apr. 2, 2013

(54) SPIROCYCLIC 3'-ALKOXYTETRAMIC ACIDS AND-TETRONIC ACIDS

(75) Inventors: Reiner Fischer, Monheim (DE); Oliver Gaertzen, Köln (DE); Stefan Lehr, Liederbach (DE); Thomas Bretschneider, Lohmar (DE); Dieter Feucht, Eschborn (DE); Olga Malsam, Rösrath (DE); Christian Arnold, Langenfeld (DE); Thomas Auler, Leichlingen (DE); Martin Jeffrey Hills, Idstein (DE); Heinz Kehne, Hofheim (DE); Chris Rosinger, Hofheim am Taunus (DE)

(73) Assignee: Bayer Cropscience AG, Monheim (DE)

( * ) Notice: Subject to any disclaimer, the term of this patent is extended or adjusted under 35 U.S.C. 154(b) by 864 days.

(21) Appl. No.: 11/630,246

(22) PCT Filed: Jun. 18, 2005

(86) PCT No.: PCT/EP2005/006588
§ 371 (c)(1),
(2), (4) Date: Oct. 9, 2007

(87) PCT Pub. No.: WO2006/000355
PCT Pub. Date: Jan. 5, 2006

(65) Prior Publication Data
US 2009/0029858 A1  Jan. 29, 2009

(30) Foreign Application Priority Data
Jun. 25, 2004  (DE) .......................... 10 2004 030 753

(51) Int. Cl.
C07D 207/26 (2006.01)

(52) U.S. Cl. ...................................... 548/544

(58) Field of Classification Search ............... 548/544
See application file for complete search history.

(56) References Cited

U.S. PATENT DOCUMENTS

| | | | |
|---|---|---|---|
| 4,021,224 A | 5/1977 | Pallos et al. | |
| 4,186,130 A | 1/1980 | Teach | |
| 4,623,727 A | 11/1986 | Hübele | |
| 4,639,266 A | 1/1987 | Heubach et al. | |
| 4,881,966 A | 11/1989 | Nyffeler et al. | |
| 4,891,057 A | 1/1990 | Sohn et al. | |
| 4,902,340 A | 2/1990 | Hubele | |
| 5,258,527 A | 11/1993 | Krauskopf et al. | |
| 5,262,383 A | 11/1993 | Fischer et al. | |
| 5,314,863 A | 5/1994 | Löher et al. | |
| 5,380,852 A | 1/1995 | Schütze et al. | |
| 5,401,700 A | 3/1995 | Sohn et al. | |
| 5,407,897 A | 4/1995 | Cary et al. | |
| 5,504,057 A | 4/1996 | Fischer et al. | |
| 5,508,436 A | 4/1996 | Fischer et al. | |
| 5,516,750 A | 5/1996 | Willms et al. | |
| 5,567,671 A | 10/1996 | Fischer et al. | |
| 5,589,469 A | 12/1996 | Fischer et al. | |
| 5,610,122 A | 3/1997 | Fischer et al. | |
| 5,622,917 A | 4/1997 | Fischer et al. | |
| 5,677,449 A | 10/1997 | Fischer et al. | |
| 5,700,758 A | 12/1997 | Rösch et al. | |
| 5,739,079 A | 4/1998 | Holdgrün et al. | |
| 5,830,825 A | 11/1998 | Fischer et al. | |
| 5,830,826 A | 11/1998 | Fischer et al. | |
| 5,847,211 A * | 12/1998 | Fischer et al. | 564/123 |
| 5,922,732 A | 7/1999 | Urch et al. | |
| 6,114,374 A | 9/2000 | Lieb et al. | |
| 6,140,358 A | 10/2000 | Lieb et al. | |
| 6,200,932 B1 | 3/2001 | Fischer et al. | |
| 6,235,560 B1 | 5/2001 | Ma et al. | |
| 6,235,680 B1 | 5/2001 | Ziemer et al. | |
| 6,251,827 B1 | 6/2001 | Ziemer et al. | |
| 6,288,102 B1 | 9/2001 | Hagemann et al. | |

(Continued)

FOREIGN PATENT DOCUMENTS

| | | |
|---|---|---|
| CA | 2 492 096 A1 | 1/2004 |
| CA | 2 497 074 A1 | 3/2004 |

(Continued)

OTHER PUBLICATIONS

Rauch et al. (Pesticide Biochemistry and Physiology (2003), 74(2), 91-101).*
O'Neill et al. (Pharmacol. Ther., vol. 77, No. 1, pp. 27-58 (1998).*
Delaney et al. (Drug Discovery Today, vol. 11, Nos. 17/18, Sep. 2006).*
Bretschneider et al., Chimia, 57 (2003), 697-701.*
Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem.* 6:341-345, Council of Scientific & Industrial Research (1968).
Compagnon, P.L. and Miocque, M., "Addition des Réactifs Nucléophiles Sur la Triple Liaison Nitrile," *Ann. Chim.* 5:11-22, Societa. Chimica Italiana (1970).

(Continued)

*Primary Examiner* — Robert Havlin
(74) *Attorney, Agent, or Firm* — Sterne, Kessler, Goldstein & Fox PLLC

(57) ABSTRACT

The invention relates to novel 3'-alkoxy spirocyclic tetramic and tetronic acids of formula (I), wherein A, B, D, Q1, Q2, G, W, X, Y and Z are as defined in the description, to several methods and intermediate products for the production and the use thereof in the form of pesticides and/or herbicides and/or microbicides, to selective herbicide agents, 3'-alkoxy spicrorylic tetramic and tetronic acids and to at least one compound which improves cultivated plants compatibility.

(I)

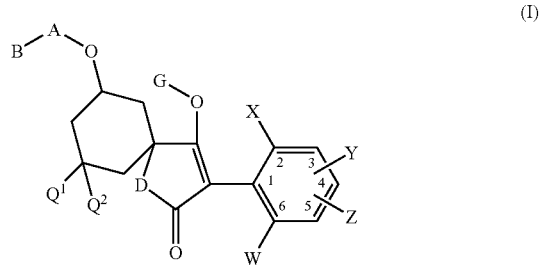

14 Claims, No Drawings

U.S. PATENT DOCUMENTS

| | | | |
|---|---|---|---|
| 6,316,486 B1 * | 11/2001 | Lieb et al. | 514/411 |
| 6,472,419 B1 | 10/2002 | Fischer et al. | |
| 6,589,976 B1 | 7/2003 | Fischer et al. | |
| 6,861,391 B1 | 3/2005 | Fischer et al. | |
| 2002/0022575 A1 | 2/2002 | Fischer et al. | |
| 2002/0061913 A1 | 5/2002 | Urch et al. | |
| 2002/0072617 A1 | 6/2002 | Hagemann et al. | |
| 2002/0188136 A1 | 12/2002 | Lieb et al. | |
| 2003/0045432 A1 | 3/2003 | Fischer et al. | |
| 2003/0073851 A1 | 4/2003 | Lieb et al. | |
| 2003/0096806 A1 | 5/2003 | Lieb et al. | |
| 2003/0171219 A1 * | 9/2003 | Lieb et al. | 504/221 |
| 2003/0171220 A1 | 9/2003 | Ziemer et al. | |
| 2003/0199572 A1 | 10/2003 | Lieb et al. | |
| 2003/0216260 A1 | 11/2003 | Ruther et al. | |
| 2003/0228984 A1 | 12/2003 | Hagemann et al. | |
| 2004/0009999 A1 | 1/2004 | Fischer et al. | |
| 2005/0054535 A1 | 3/2005 | Fischer et al. | |
| 2005/0164883 A1 | 7/2005 | Maetzke et al. | |
| 2006/0160847 A1 | 7/2006 | Fischer et al. | |
| 2006/0166829 A1 | 7/2006 | Fischer et al. | |
| 2007/0275858 A1 | 11/2007 | Fischer et al. | |
| 2009/0281157 A1 | 11/2009 | Fischer et al. | |

FOREIGN PATENT DOCUMENTS

| | | |
|---|---|---|
| CA | 2 518 620 A1 | 9/2004 |
| CA | 2 544 537 A1 | 5/2005 |
| CA | 2 544 548 A1 | 5/2005 |
| CA | 2 546 815 A1 | 6/2005 |
| CA | 2 546 817 A1 | 6/2005 |
| CA | 2 552 737 A1 | 7/2005 |
| DE | 2 218 097 | 11/1972 |
| DE | 2 350 547 | 4/1974 |
| DE | 196 21 522 A1 | 12/1997 |
| DE | 103 51 646 A1 | 6/2005 |
| DE | 103 51 647 A1 | 6/2005 |
| DE | 103 54 628 A1 | 6/2005 |
| DE | 103 54 629 A1 | 6/2005 |
| EP | 0 086 750 A2 | 8/1983 |
| EP | 0 094 349 A2 | 11/1983 |
| EP | 0 174 562 A2 | 3/1986 |
| EP | 0 191 736 A2 | 8/1986 |
| EP | 0 269 806 A1 | 6/1988 |
| EP | 0 333 131 A1 | 9/1989 |
| EP | 0 346 620 A1 | 12/1989 |
| EP | 0 456 063 A2 | 11/1991 |
| EP | 0 492 366 A2 | 7/1992 |
| EP | 0 521 334 A1 | 1/1993 |
| EP | 0 528 156 A1 | 2/1993 |
| EP | 0 582 198 A2 | 2/1994 |
| EP | 0 595 130 A1 | 5/1994 |
| EP | 0 596 298 A2 | 5/1994 |
| EP | 0 613 618 A1 | 9/1994 |
| EP | 0 613 884 A2 | 9/1994 |
| EP | 0 613 885 A2 | 9/1994 |
| EP | 0 647 637 A1 | 4/1995 |
| EP | 0 668 267 A1 | 8/1995 |
| WO | WO 91/07874 A1 | 6/1991 |
| WO | WO 91/08202 A1 | 6/1991 |
| WO | WO 94/29268 A1 | 12/1994 |
| WO | WO 95/01358 A1 | 1/1995 |
| WO | WO 95/07897 A1 | 3/1995 |
| WO | WO 95/20572 A1 | 8/1995 |
| WO | WO 95/26954 A1 | 10/1995 |
| WO | WO 96/20196 A1 | 7/1996 |
| WO | WO 96/25395 A1 | 8/1996 |
| WO | WO 96/35664 A1 | 11/1996 |
| WO | WO 96/37494 A1 | 11/1996 |
| WO | WO 97/01535 A1 | 1/1997 |
| WO | WO 97/02243 A1 | 1/1997 |
| WO | WO 97/36868 A1 | 10/1997 |
| WO | WO 98/05638 A2 | 2/1998 |
| WO | WO 98/06721 A1 | 2/1998 |
| WO | WO 98/25923 A1 | 6/1998 |
| WO | WO 98/25928 A1 | 6/1998 |
| WO | WO 99/16748 A1 | 4/1999 |
| WO | WO 99/24437 A1 | 5/1999 |
| WO | WO 99/43649 A1 | 9/1999 |
| WO | WO 99/48869 A1 | 9/1999 |
| WO | WO 99/55673 A1 | 11/1999 |
| WO | WO 99/66795 A1 | 12/1999 |
| WO | WO 01/17972 A2 | 3/2001 |
| WO | WO 01/23354 A2 | 4/2001 |
| WO | WO 01/74770 A1 | 10/2001 |
| WO | WO 03/013249 A1 | 2/2003 |
| WO | WO 2004/007448 A1 | 1/2004 |
| WO | WO 2004/024688 A1 | 3/2004 |
| WO | WO 2004/065366 A1 | 8/2004 |
| WO | WO 2004/080962 A1 | 9/2004 |
| WO | WO 2004/111042 A1 | 12/2004 |
| WO | WO 2005/044796 A1 | 5/2005 |
| WO | WO 2005/049569 A1 | 6/2005 |
| WO | WO 2005/066125 A1 | 7/2005 |

OTHER PUBLICATIONS

Edward, J.T. and Jitrangsri, C., "Stereochemistry of the Bucherer-Bergs and Strecker Reactions of 4-*tert*-Butylcyclohexanone," *Can. J. Chem.* 53:3339-3350, NRC Research Press (1975).

Harrison, H.R., et al., "Use of molecular sieves in the methyl esterification of carboxylic acids," *Chem. Ind.*, p. 1568, Society of Chemical Industry (1968).

Ito, M., et al., "Efficient *N*-sulfenylation of Dihydropyrrole Derivatives Using *N*-sulfenylphthalimides," *Heterocycles* 57:909-914, Elsevier (2002).

Munday, L., "Amino-acids of the Cyclohexane Series. Part I.," *J. Chem. Soc.*, pp. 4372-4379, Royal Society of Chemistry (1961).

Sonntag, N.O.V., "The Reactions of Aliphatic Acid Chlorides," *Chem. Rev.* 52:237-416, American Chemical Society (1953).

Dialog File 351, Accession No. 4963457, English language abstract for EP 0 346 620 A1 (listed on accompanying PTO/SB/08A as FP9).

International Search Report for International Application No. PCT/EP2005/006588, European Patent Office, Netherlands, mailed on Sep. 29, 2005.

Office Action, U.S. Appl. No. 10/542,514, inventors Fischer, R., et al., filed on Feb. 2, 2006, mailed on Mar. 13, 2009.

Office Action mailed Nov. 18, 2009, in U.S. Appl. No. 10/542,514, Fischer et al., with a 35 U.S.C. § 371(c) date of Feb. 2, 2006.

* cited by examiner

SPIROCYCLIC 3'-ALKOXYTETRAMIC ACIDS AND-TETRONIC ACIDS

This application is a National Stage of International Application No. PCT/EP2005/006588, filed Jun. 18, 2005, which claims the benefit of German Patent Application No. 102004030753.9, filed Jun. 25, 2004. The entirety of each of these applications is incorporated by reference herein.

The present invention relates to novel 3'-alkoxy-substituted spirocyclic ketoenols, to a plurality of processes for their preparation and to their use as pesticides, microbicides and/or herbicides. The invention also provides selective herbicidal compositions comprising firstly the 3'-alkoxy-substituted spirocyclic ketoenols and secondly a compound which improves crop plant tolerance.

1H-arylpyrrolidinedione derivatives having herbicidal, insecticidal or acaricidal action are known: EP-A-456 063, EP-A-521 334, EP-A-613 884, EP-A-613 885, WO 95/01 358, WO 98/06 721, WO 98/25 928, WO 99/16 748, WO 99/24 437 or WO 01/17 972.

Also known are alkoxy-substituted spirocyclic 1H-arylpyrrolidinedione derivatives: EP-A-596 298, WO 95/26 954, WO 95/20 572, EP-A-0 668 267, WO 96/25 395, WO 96/35 664, WO 97/01 535, WO 97/02 243, WO 97/36 868, WO 98/05 638, WO 99/43 649, WO 99/48 869, WO 99/55 673, WO 01/23 354, WO 01/74 770, WO 01/17 972, WO 03/013 249, WO 2004/02 4688, WO 2004/065 366, WO 2004/08 0962, WO 2004/007448, WO 2004/111042, DE-A-1035 1646, DE-A-1035 4628, DE-A-1035 4629, DE-A-1035 1647.

It is known that certain $\Delta^3$-dihydrofuran-2-one derivatives have herbicidal, insecticidal or acaricidal properties: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 2004/024 688, WO 2004/080 962.

However, the herbicidal and/or acaricidal and/or insecticidal activity and/or the activity spectrum and/or the compatibility of the known compounds with plants, in particular with crop plants, is not always satisfactory.

This invention now provides novel compounds of the formula (I)

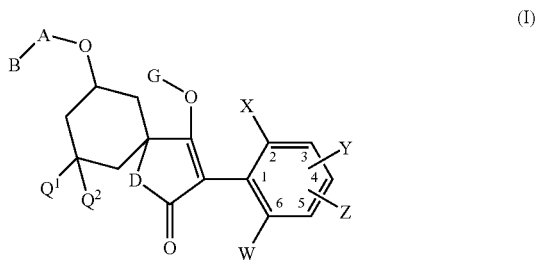

in which
  W represents hydrogen, alkyl, alkenyl, alkynyl, halogen, alkoxy, haloalkyl, haloalkoxy or cyano,
  X represents halogen, alkyl, alkenyl, alkynyl, alkoxy, alkoxyalkoxy, haloalkyl, haloalkoxy or cyano,
  Y in the 4-position represents hydrogen, halogen, alkoxy, cyano, haloalkyl or haloalkoxy,
  Z represents hydrogen.
  W also represents hydrogen, halogen or alkyl,
  X also represents halogen, alkyl, alkoxy, haloalkyl, haloalkoxy or cyano,
  Y in the 4-position also represents optionally substituted phenyl or hetaryl,
  Z also represents hydrogen.
  W likewise represents hydrogen, halogen or alkyl
  X likewise represents halogen, alkyl, alkoxy, haloalkyl, haloalkoxy or cyano,
  Y likewise in the 5-position represents optionally substituted phenyl or hetaryl,
  Z in the 4-position likewise represents hydrogen, alkyl or halogen.
  W moreover represents hydrogen, alkyl, alkenyl, alkynyl, alkoxy, halogen, cyano or trifluoromethyl,
  X moreover represents halogen, alkyl alkenyl, alkynyl, alkoxy, alkoxyalkoxy, haloalkyl, haloalkoxy or cyano,
  Y in the 4-position moreover represents alkyl,
  Z moreover represents hydrogen.
  W furthermore represents hydrogen, halogen, alkyl or alkoxy,
  X furthermore represents halogen, alkyl, alkoxy, haloalkyl, haloalkoxy or cyano,
  Y in the 4-position furthermore represents hydrogen, halogen, alkyl, haloalkyl or haloalkoxy,
  Z in the 3- or 5-position furthermore represents halogen, alkyl, haloalkyl, cyano, alkoxy or haloalkoxy.
  A represents an optionally substituted alkanediyl group or represents cycloalkyl which is optionally substituted and/or optionally interrupted by a heteroatom,
  B represents hydrogen or in each case optionally substituted alkyl, alkenyl, alkoxy, alkoxyalkyl, phenyl, hetaryl or represents cycloalkyl which is optionally substituted and/or optionally interrupted by heteroatoms and/or C=O,
  D represents NH or oxygen,
  $Q^1$ represents hydrogen, represents in each case optionally substituted alkyl, alkoxy, alkoxyalkyl or alkylthioalkyl, represents optionally substituted cycloalkyl in which optionally one methylene group is replaced by heteroatoms or represents optionally substituted phenyl, hetaryl, phenylalkyl or hetarylalkyl,
  $Q^2$ represents hydrogen or alkyl,
  $Q^1$ and $Q^2$ together with the carbon to which they are attached represent an optionally substituted $C_3$-$C_6$-ring which may optionally be interrupted by a heteroatom,
  G represents hydrogen (a) or represents one of the groups

(b)

(c)

(d)

(e)

E, or (f)

-continued

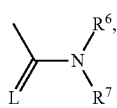
(g)

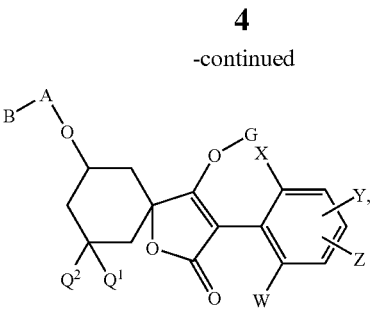
(I-2)

in which
A, B, G, $Q^1$, $Q^2$, W, X, Y and Z are as defined above.

Including the different meanings (a), (b), (c), (d), (e), (f) and (g) of the group G, the following principal structures (I-1-a) to (I-1-g) result if D represents NH (1), in which E represents a metal ion or an ammonium ion, L represents oxygen or sulphur, M represents oxygen or sulphur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the nitrogen atom to which they are attached form a cycle which is optionally substituted and which optionally contains oxygen or sulphur.

Depending inter alia on the nature of the substituents, the compounds of the formula (I) can be present as optical isomers or isomer mixtures of varying composition which, if appropriate, can be separated in the customary manner. The present invention provides both the pure isomers and the isomer mixtures, their preparation and use as well as compositions comprising them. However, hereinbelow, for the sake of simplicity, only compounds of the formula (I) are referred to although this means both the pure compounds and, if appropriate, also mixtures having varying proportions of isomeric compounds.

Including D being NH (1) and D being O (2), the following principal structures (I-1) and (I-2) result:

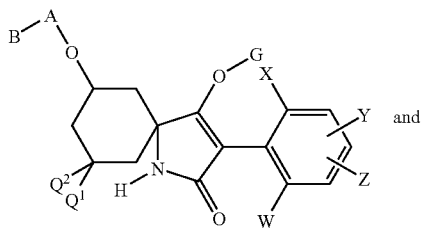
(I-1)

and

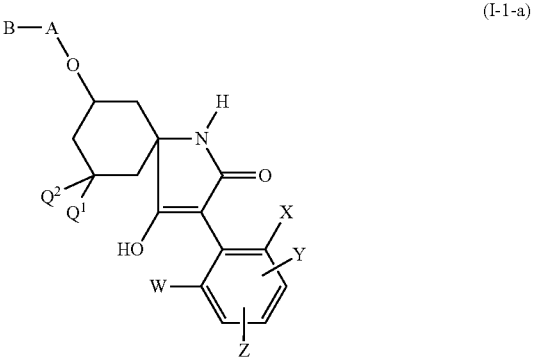
(I-1-a)

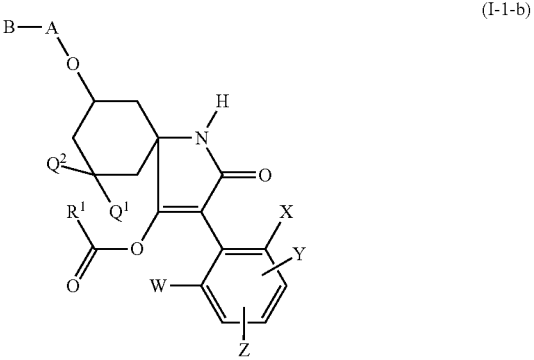
(I-1-b)

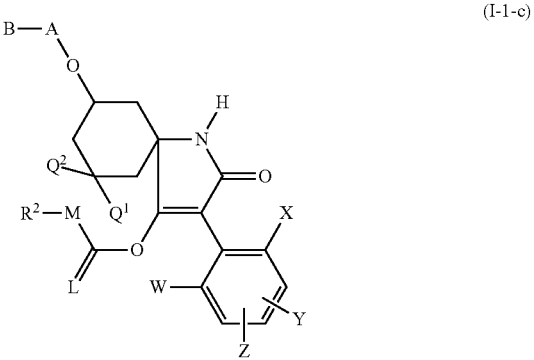
(I-1-c)

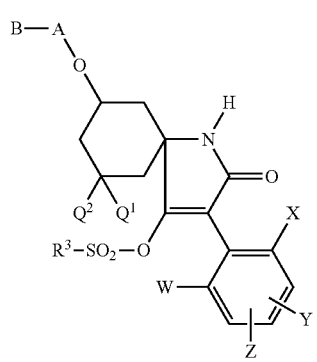
(I-1-d)
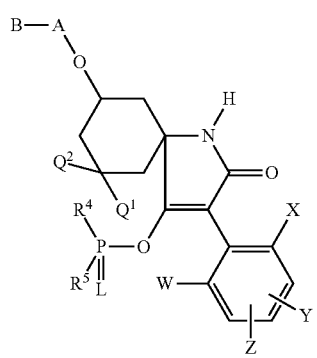
(I-1-e)
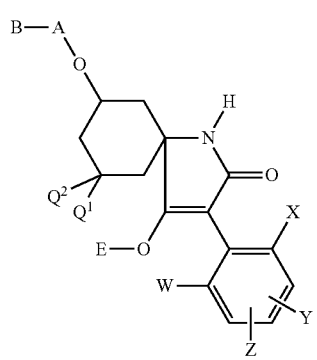
(I-1-f)
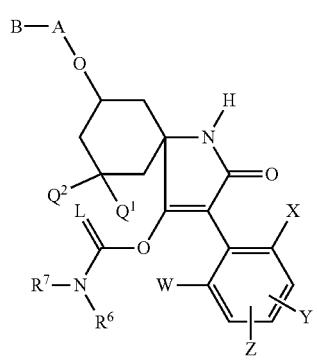
(I-1-g)
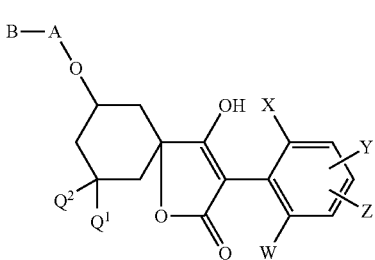
(I-2-a)
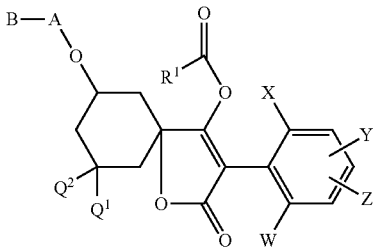
(I-2-b)
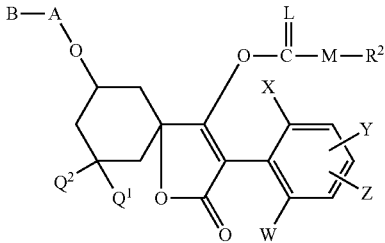
(I-2-c)
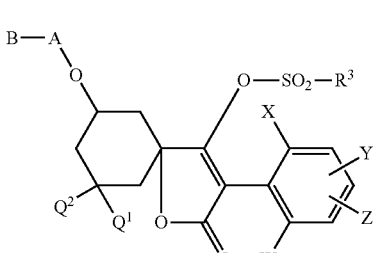
(I-2-d)
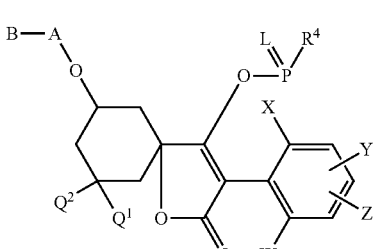
(I-2-e)
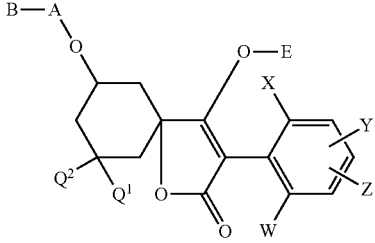
(I-2-f)
in which
A, B, E, L, M, $Q^1$, $Q^2$, W, X, Y, Z, $R^1$, $R^2$, $R^3$, $R^4$, $R^5$, $R^6$ and $R^7$ are as defined above.
Including the different meanings (a), (b), (c), (d), (e), (f) and (g) of the group G, the following principal structures (I-2-a) to (I-2-g) result if D represents O (2), -continued

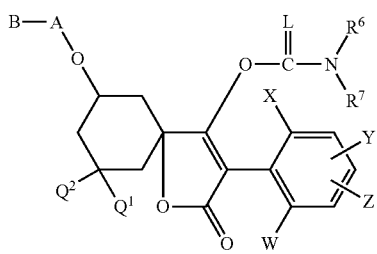
(I-2-g)

in which

A, B, E, L, M, $Q^1$, $Q^2$, W, X, Y, Z, $R^1$, $R^2$, $R^3$, $R^4$, $R^5$, $R^6$ and $R^7$ are as defined above.

Furthermore, it has been found that the novel compounds of the formula (I) are obtained by the processes described below:

(A) Compounds of the formula (I-1-a)

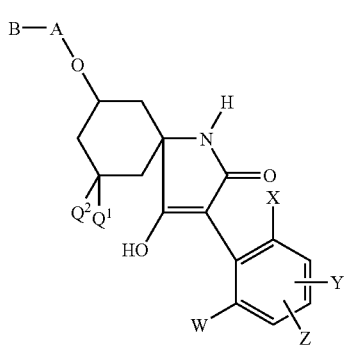
(I-1-a)

in which

A, B, $Q^1$, $Q^2$, W, X, Y and Z are as defined above are obtained when compounds of the formula (II)

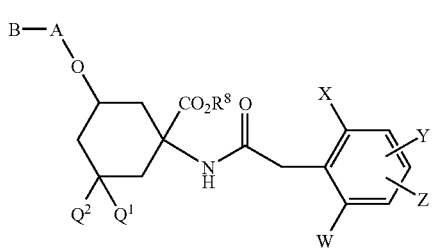
(II)

in which

A, B, $Q^1$, $Q^2$, W, X, Y and Z are as defined above and $R^8$ represents alkyl (preferably $C_1$-$C_6$-alkyl), are condensed intramolecularly in the presence of a diluent and in the presence of a base.

(B) Moreover, it has been found that compounds of the formula (I-2-a)

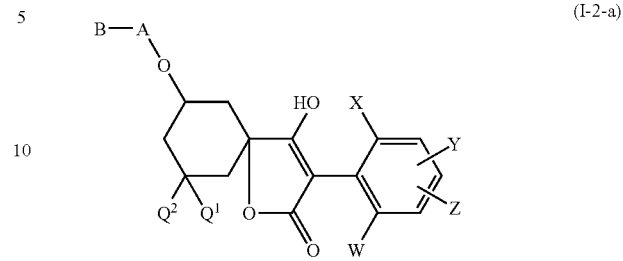
(I-2-a)

in which

A, B, $Q^1$, $Q^2$, W, X, Y and Z are as defined above, are obtained when compounds of the formula (III)

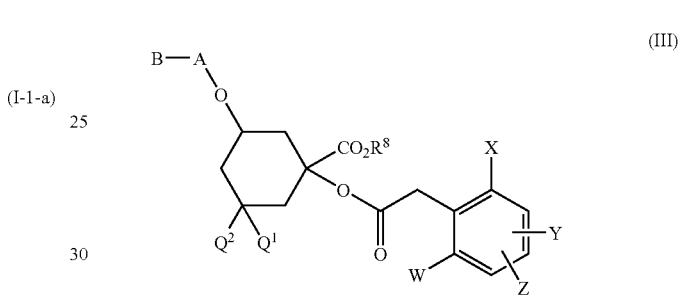
(III)

in which

A, B, $Q^1$, $Q^2$, W, X, Y, Z and $R^8$ are as defined above, are condensed intramolecularly in the presence of a diluent and in the presence of a base.

Moreover, it has been found (C) that the compounds of the formulae (I-1-b) to (I-2-b) shown above in which $R^1$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case α) reacted with compounds of the formula (IV)

(IV)

in which $R^1$ is as defined above and

Hal represents halogen (in particular chlorine or bromine)

or

β) reacted with carboxylic anhydrides of the formula (V)

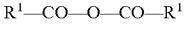
$R^1$—CO—O—CO—$R^1$ (V)

in which $R^1$ is as defined above, if appropriate in the presence of a diluent and if appropriate in the presence of an acid binder;

(D) that the compounds of the formulae (I-1-c) to (I-2-c) shown above in which $R^2$, A, B, $Q^1$, $Q^2$, W, M, X, Y and Z are as defined above and L represents oxygen are obtained when compounds of the formulae (I-1-a) to (I-2-a) shown above in which A, B, $Q^1$, $Q^2$, W, X, Y and Z are as defined above are in each case reacted with chloroformic esters or chloroformic thioesters of the formula (VI)

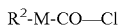 (VI)

in which
$R^2$ and M are as defined above,
if appropriate in the presence of a diluent and if appropriate in the presence of an acid binder;
(E) that compounds of the fomulae (I-1-c) to (I-2-c) shown above in which $R^2$, A, B, $Q^1$, $Q^2$, W, M, X, Y and Z are as defined above and L represents sulphur are obtained when compounds of the formulae (I-1-a) to (I-2-a) shown above in which A, B, $Q^1$, $Q^2$, W, X, Y and Z are as defined above are in each case reacted with chloromonothioformic esters or chlorodithioformic esters of the formula (VII)

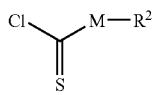 (VII)

in which
M and $R^2$ are as defined above,
if appropriate in the presence of a diluent and if appropriate in the presence of an acid binder,
(F) that compounds of the formulae (I-1-d) to (I-2-d) shown above in which $R^3$, A, B, W, $Q^1$, $Q^2$, X, Y and Z are as defined above are obtained when compounds of the formulae (I-1-a) to (I-2-a) shown above in which A, B, $Q^1$, $Q^2$, W, X, Y and Z are as defined above are in each case reacted with sulphonyl chlorides of the formula (VIII)

 (VIII)

in which
$R^3$ is as defined above,
if appropriate in the presence of a diluent and if appropriate in the presence of an acid binder,
(G) that compounds of the formulae (I-1-e) to (I-2-e) shown above in which L, $R^4$, $R^5$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case reacted with phosphorus compounds of the formula (IX)

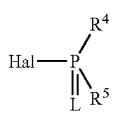 (IX)

in which
L, $R^4$ and $R^5$ are as defined above and
Hal represents halogen (in particular chlorine or bromine),
if appropriate in the presence of a diluent and if appropriate in the presence of an acid binder,
(H) that compounds of the formulae (I-1-f) to (I-2-f) shown above in which E, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case reacted with metal compounds or amines of the formulae (X) or (XI), respectively,

 (X)

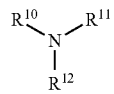 (XI)

in which
Me represents a mono- or divalent metal (preferably an alkali metal or an alkaline earth metal, such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent,
(I) that compounds of the formulae (I-1-g) to (I-2-g) shown above in which L, $R^6$, $R^7$, A, B, $Q^1$, $Q^2$, W, X, Y and Z are as defined above are obtained when compounds of the formulae (I-1-a) to (I-2-a) shown above in which A, B, $Q^1$, $Q^2$, W, X Y and Z are as defined above are in each case α) reacted with isocyanates or isothiocyanates of the formula (XII)

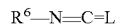 (XII)

in which
$R^6$ and L are as defined above,
if appropriate in the presence of a diluent and if appropriate in the presence of a catalyst, or
ß) reacted with carbamoyl chlorides or thiocarbamoyl chlorides of the formula (XIII)

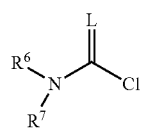 (XIII)

in which
L, $R^6$ and $R^7$ are as defined above,
if appropriate in the presence of a diluent and if appropriate in the presence of an acid binder.

Furthermore, it has been found that the novel compounds of the formula (I) are highly active pesticides, preferably insecticides, acaricides and/or fungicides and/or herbicides, and are additionally frequently tolerated very well by plants, in particular by crop plants.

Surprisingly, it has now also been found that certain substituted cyclic ketoenols, when used jointly with the compounds which improve crop plant tolerance (safeners/antidotes) described below, are extremely effective in preventing damage to the crop plants and can be used especially advantageously as combination products with a broad range of activity for the selective control of unwanted plants in crops of useful plants, such as, for example, in cereals, but also in maize, soybeans and rice.

The invention also relates to selective herbicidal compositions comprising an effective amount of an active compound combination comprising, as components,
(a') at least one substituted cyclic ketoenol of the formula (I) in which A, B, D, G, $Q^1$, $Q^2$, W, X, Y and Z are as defined above
and
(b') at least one compound which improves crop plant tolerance and which is selected from the following group of compounds:
4-dichloroacetyl-1-oxa-4-azaspiro[4.5]decane (AD-67, MON-4660), 1-dichloro-acetylhexahydro-3,3,8a-trimethylpyrrolo[1,2-a]pyrimidin-6(2H)one (dicyclonon, BAS-145138), 4-dichloroacetyl-3,4-dihydro-3-methyl-2H-1,4-benzoxazine (benoxacor), 1-methylhexyl 5-chloro-quinolin-8-oxyacetate (cloquintocet-mexyl—cf. also related compounds in EP-A-86750, EP-A-94349, EP-A-191736, EP-A492366), 3-(2-chlorobenzyl)-1-(1-methyl-1-phenylethyl)urea(cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate(dimepiperate), 2,2-dichloro-N-(2-oxo-2-(2-propenylamino)ethyl)-N-(2-propenyl)acetamide (DKA-24), 2,2-dichloro-N,N-di-2-propenylacetamide(dichlormid), 4,6-dichloro-2-phenylpyrimidine(fenclorim), ethyl 1-(2,4-dichlorophenyl)-5-trichloromethyl-1H-1,2,4-triazole-3-carboxylate(fenchlorazole-ethyl—cf. also related compounds in EP-A-174562 and EP-A-346620), phenylmethyl 2-chloro-4-trifluoromethylthiazole-5-carboxylate(flurazole), 4-chloro-N-(1,3-dioxolan-2-ylmethoxy)-α-trifluoroacetophenone oxime(fluxofenim), 3-dichloroacetyl-5-(2-furanyl)-2,2-dimethyloxazolidine(furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl-3,6-dichloro-2-methoxybenzoate(lactidichlor), (4-chloro-o-tolyloxy)acetic acid (MCPA), 2-(4-chloro-o-tolyloxy)-propionic acid(mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane 4-carbodithioate (MG-838), 1,8-naphthalic anhydride, α-(1,3-dioxolan-2-ylmethoximino)phenylacetonitrile(oxabetrinil), 2,2-dichloro-N-(1,3-dioxolan-2-ylmethyl)-N-(2-propenyl)acetamide (PPG-1292), 3-dichloroacetyl-2,2dimethyl-oxazolidine (R-28725), 3-dichloroacetyl-2,2,5-trimethyl-oxazolidine (R-29148), 4-4-chloro-o-tolyl)-butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinolin-8-oxyacetate, 4-allyloxybutyl 5-chloroquinolin-8-oxyacetate, 1-allyloxyprop-2-yl 5-chloroquinolin-8-oxyacetate, methyl 5-chloroquinoxalin-8-oxyacetate, ethyl 5-chloroquinolin-8-oxyacetate, allyl 5-chloroquinoxalin-8-oxyacetate, 2-oxoprop-1-yl 5-chloroquinolin-8-oxyacetate, diethyl 5-chloroquinolin-8-oxy-malonate, diallyl 5-chloroquinoxalin-8-oxymalonate, diethyl 5-chloroquinolin-8-oxymalonate (cf. also related compounds in EP-A-582198), 4-carboxychroman-4-ylaceticacid (AC-304415, cf. EP-A-613618), 4-chlorophenoxyacetic acid, 3,3'-dimethyl4-methoxy-benzophenone, 1-bromo-4-chloromethylsulphonylbenzene, 1-[4-(N-2-methoxybenzoyIsulphamoyl)phenyl]-3-methylurea (alias N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzenesulphonamide, and/or one of the following compounds (defined by general formulae)
of the general formula (IIa)

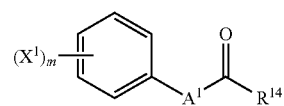

or of the general formula (IIb)

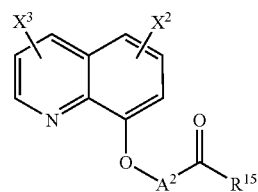

or of the formula (IIc)

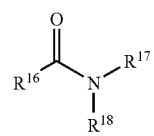

where
m represents a number 0, 1, 2, 3, 4 or 5,
$A^1$ represents one of the divalent heterocyclic groups outlined hereinbelow,

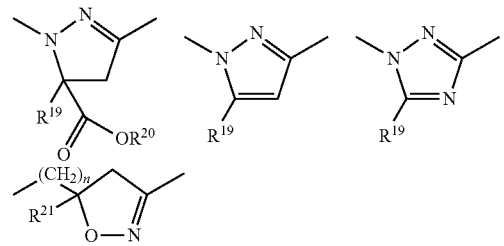

n represents a number 0, 1, 2, 3, 4 or 5,
$A^2$ represents alkanediyl having 1 or 2 carbon atoms which is optionally substituted by $C_1$-$C_4$-alkyl and/or $C_1$-$C_4$-alkoxycarbonyl and/or $C_1$-$C_4$-alkenyloxycarbonyl, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)amino, R represents $C_1$-$C_4$-alkyl which is optionally substituted by fluorine, chlorine and/or bromine, $R^{17}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, $R^{18}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyi, piperidinyl, each of which is optionally substituted by fluorine, chlorine and/or bromine, or represents phenyl which is optionally substituted by fluorine, chlorine and/or bromine or $C_1$-$C_4$-alkyl, $R^{17}$ and $R^{18}$ together also represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $R^{20}$ represents hydrogen, or represents $C_1$-$C_6$-alkyl, $C_3$-$C_6$-cycloalkyl or tri($C_1$-$C_4$-alkyl)silyl, each of which is optionally substituted by hydroxyl, cyano, halogen or $C_1$-$C_4$-alkoxy, $R^{21}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds (defined by general formulae)

of the general formula (IId)

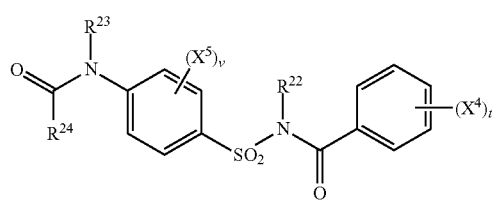

(IId)

or of the general formula (IIe)

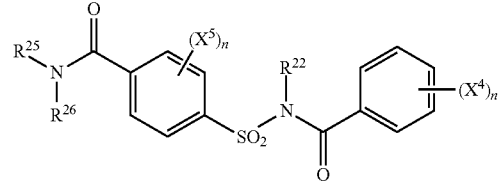

(IIe)

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, or represents $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, each of which is optionally substituted by cyano, halogen or $C_1$-$C_4$-alkoxy, or represents $C_3$-$C_6$-cycloalkyl, $C_3$-$C_6$-cycloalkyloxy, $C_3$-$C_6$-cycloalkylthio or $C_3$-$C_6$-cycloalkylamino, each of which is optionally substituted by cyano, halogen or $C_1$-$C_4$-alkyl, $R^{25}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, $R^{26}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, or represents phenyl which is optionally substituted by nitro, cyano, halogen, $C_1$-$C_4$-alkyl, $C_1$-$C_4$-haloalkyl, $C_1$-$C_4$-alkoxy or $C_1$-$C_4$-haloalkoxy, or together with $R^{25}$ represents $C_2$-$C_6$-alkanediyl or $C_2$-$C_5$-oxaalkanediyl, each of which is optionally substituted by $C_1$-$C_4$-alkyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals given in the formulae mentioned hereinabove and hereinbelow are illustrated below:

W preferably represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y in the 4-position preferably represents hydrogen, halogen, $C_1$-$C_6$-alkoxy, cyano, $C_1$-$C_4$-haloalkyl or $C_1$-$C_4$-haloalkoxy, Z preferably represents hydrogen.

W also preferably represents hydrogen, halogen or $C_1$-$C_6$-alkyl,

X also preferably represents halogen, $C_1$-$C_6$-alkyl, $C_1$-$C_6$-alkoxy, $C_1$-$C_4$-haloalkyl, $C_1$-$C_4$-haloalkoxy or cyano, Y also in the 4-position preferably represents $V^1$- and $V^2$-substituted phenyl or pyridyl, Z also preferably represents hydrogen, $V^1$ also preferably represents halogen, $C_1$-$C_{12}$-alkyl, $C_1$-$C_6$-alkoxy, $C_1$-$C_4$-haloalkyl or $C_1$-$C_4$-haloalkoxy, $V^2$ also preferably represents hydrogen, halogen, $C_1$-$C_6$-alkyl, $C_1$-$C_6$-alkoxy or $C_1$-$C_4$-haloalkyl, $V^1$ and $V^2$ together also preferably represent $C_3$-$C_4$-alkanediyl which may optionally be substituted by halogen and/or $C_1$-$C_2$-alkyl and which may optionally be interrupted by one or two oxygen atoms.

W likewise preferably represents hydrogen, halogen or $C_1$-$C_6$-alkyl,

X likewise preferably represents halogen, $C_1$-$C_6$-alkyl, $C_1$-$C_6$-alkoxy, $C_1$-$C_4$-haloalkyl, $C_1$-$C_4$-haloalkoxy or cyano, Y likewise in the 5-position preferably represents $V^1$- and $V^2$-substituted phenyl or pyridyl, Z likewise in the 4-position preferably represents hydrogen, $C_1$-$C_6$-alkyl or halogen, $V^1$ likewise preferably represents halogen, $C_1$-$C_{12}$-alkyl, $C_1$-$C_6$-alkoxy, $C_1$-$C_4$-haloalkyl or $C_1$-$C_4$-haloalkoxy, $V^2$ likewise preferably represents hydrogen, halogen, $C_1$-$C_6$-alkyl, $C_1$-$C_6$-alkoxy or $C_1$-$C_4$-haloalkyl, $V^1$ and $V^2$ together likewise preferably represent $C_3$-$C_4$-alkanediyl which may optionally be substituted by halogen and/or $C_1$-$C_2$-alkyl and which may optionally be interrupted by one or two oxygen atoms.

W moreover preferably represents hydrogen, $C_1$-$C_6$-alkyl, $C_2$-$C_6$-alkenyl, $C_2$-$C_6$-alkynyl, $C_1$-$C_6$-alkoxy, halogen, trifluoromethyl or cyano, X moreover preferably represents halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y moreover in the 4-position preferably represents $C_1$-$C_6$-alkyl, Z moreover preferably represents hydrogen.

W furthermore preferably represents hydrogen, halogen, $C_1$-$C_6$-alkyl or $C_1$-$C_6$-alkoxy, X furthermore preferably represents halogen, $C_1$-$C_6$-alkyl, $C_1$-$C_6$-alkoxy, $C_1$-$C_4$-haloalkyl, $C_1$-$C_4$-haloalkoxy or cyano, Y furthermore in the 4-position preferably represents hydrogen, halogen or $C_1$-$C_6$-alkyl, $C_1$-$C_4$-haloalkyl or $C_1$-$C_4$-haloalkoxy, Z furthermore in the 3- or 5-position preferably represents halogen, $C_1$-$C_6$-alkyl, $C_1$-$C_4$-haloalkyl, cyano, $C_1$-$C_6$-alkoxy or $C_1$-$C_4$-haloalkoxy.

A preferably represents an optionally $C_1$-$C_4$-alkyl-substituted $C_1$-$C_4$-alkanediyl group or represents optionally $C_1$-$C_4$-alkyl-substituted $C_5$-$C_8$-cycloalkyl in which optionally one methylene group is replaced by oxygen.

B preferably represents hydrogen or represents in each case optionally halogen-substituted $C_1$-$C_8$-alkyl, $C_2$-$C_8$-alkenyl, $C_1$-$C_6$-alkoxy, $C_1$-$C_6$-alkoxy-$C_1$-$C_4$-alkoxy, $C_1$-$C_4$-alkoxy-bis-$C_1$-$C_4$-alkoxy, represents optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl, represents optionally halogen-, $C_1$-$C_4$-alkyl- or $C_1$-$C_2$-haloalkyl-substituted pyridyl, pyrimidyl, thiazolyl or thienyl or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which optionally one or two not directly adjacent methylene groups are replaced by oxygen, two methylene groups are replaced by the radical —O—CO— or three methylene groups are replaced by the radical —O—CO—O—.

D preferably represents NH or oxygen.

$Q^1$ preferably represents hydrogen or represents in each case optionally halogen-substituted $C_1$-$C_6$-alkyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl or represents optionally halogen-, $C_1$-$C_4$-alkyl- or $C_1$-$C_4$-alkoxy-substituted $C_3$-$C_6$-cycloalkyl in which optionally one methylene group is replaced by oxygen or represents phenyl, phenyl-$C_1$-$C_2$-alkyl or hetaryl, each of which is optionally mono- or disubstituted by halogen, $C_1$-$C_4$-alkyl, $C_1$-$C_4$-alkoxy, $C_1$-$C_4$-haloalkyl or $C_1$-$C_4$-haloalkoxy, $Q^2$ preferably represents hydrogen or $C_1$-$C_6$-alkyl, or $Q^1$ and $Q^2$ together with the carbon to which they are attached preferably represent a $C_3$-$C_6$-ring which is optionally mono- or disubstituted by fluorine, chlorine, $C_1$-$C_4$-alkyl, $C_1$-$C_4$-alkoxy or trifluoromethyl and in which optionally one methylene group may be replaced by oxygen.

G preferably represents hydrogen (a) or represents one of the groups

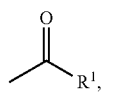 (b)

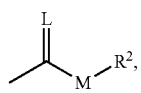 (c)

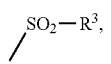 (d)

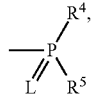 (e)

E, or (f)

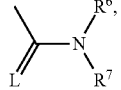 (g)

in which

E represents a metal ion or an ammonium ion,

L represents oxygen or sulphur and

M represents oxygen or sulphur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulphur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen.

$R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl.

$R^3$ preferably represents optionally halogen-substituted $C_1$-$C_9$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl.

$R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio.

$R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X particularly preferably represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y in the 4-position particularly preferably represents hydrogen, fluorine, chlorine, bromine, methoxy, ethoxy, cyano, trifluoromethyl, difluoromethoxy or trifluoromethoxy, Z particularly preferably represents hydrogen.

W also particularly preferably represents hydrogen, chlorine, bromine or $C_1$-$C_4$-alkyl, X also particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y also in the 4-position particularly preferably represents the radical

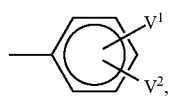

Z also particularly preferably represents hydrogen, $V^1$ also particularly preferably represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ also particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together also particularly preferably represent —O—$CH_2$—O— or —O—$CF_2$—O—.

W likewise particularly preferably represents hydrogen, chlorine, bromine or $C_1$-$C_4$-alkyl, X likewise particularly preferably represents chlorine, bromine, $C_1$-$C_4$-alkyl or $C_1$-$C_2$-haloalkyl, Y likewise in the 5-position particularly preferably represents the radical

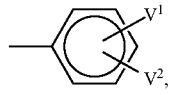

Z likewise in the 4-position particularly preferably represents hydrogen, $C_1$-$C_4$-alkyl or chlorine, $V^1$ likewise particularly preferably represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ likewise particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together likewise particularly preferably represent —O—$CH_2$—O— or —O—$CF_2$—O—.

W moreover particularly preferably represents hydrogen, $C_1$-$C_4$-alkyl, $C_2$-$C_4$-alkenyl, $C_2$-$C_4$-alkynyl, $C_1$-$C_4$-alkoxy, chlorine, bromine or trifluoromethyl, X moreover particularly preferably represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y moreover in the 4-position particularly preferably represents $C_1$-$C_4$-alkyl, Z moreover particularly preferably represents hydrogen.

W furthermore particularly preferably represents hydrogen, chlorine, bromine, $C_1$-$C_4$-alkyl or $C_1$-$C_4$-alkoxy, X furthermore particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y furthermore in the 4-position particularly preferably represents hydrogen, chlorine, bromine, $C_1$-$C_4$-alkyl, $C_1$-$C_2$-haloalkyl or $C_1$-$C_2$-haloalkoxy, Z furthermore in the 3- or 5-position particularly preferably represents fluorine, chlorine, bromine, $C_1$-$C_4$-alkyl, $C_1$-$C_2$-haloalkyl, $C_1$-$C_4$-alkoxy or $C_1$-$C_2$-haloalkoxy.

A particularly preferably represents an optionally $C_1$-$C_2$-alkyl-substituted $C_1$-$C_3$-alkanediyl group or represents $C_5$-$C_6$-cycloalkyl in which optionally one methylene group is replaced by oxygen.

B particularly preferably represents hydrogen or represents $C_1$-$C_6$-alkyl, $C_2$-$C_6$-alkenyl, $C_1$-$C_4$-alkoxy, $C_1$-$C_4$-alkoxy-$C_1$-$C_3$-alkoxy, $C_1$-$C_4$-alkoxy-bis-$C_1$-$C_3$-alkoxy, each of which is optionally mono- to trisubstituted by fluorine or chlorine, represents phenyl which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, represents pyridyl, pyrimidyl, thiazolyl or thienyl, each of which is optionally mono- or disubstituted by fluorine, chlorine, bromine, methyl, ethyl or trifluoromethyl or represents $C_3$-$C_6$-cycloalkyl which is optionally mono- or disubstituted by fluorine, chlorine, methyl, methoxy or trifluoromethyl and in which optionally two not directly adjacent methylene groups are replaced by oxygen.

D particularly preferably represents NH or oxygen.

$Q^1$ particularly preferably represents hydrogen, represents $C_1$-$C_4$-alkyl, $C_1$-$C_4$-alkoxy, $C_1$-$C_2$-alkoxy-$C_1$-$C_2$-alkyl, each of which is optionally mono- to trisubstituted by fluorine, or represents $C_3$-$C_6$-cycloalkyl which is optionally mono- or disubstituted by fluorine, chlorine, methyl, ethyl or methoxy and in which optionally one methylene group may be replaced by oxygen.

$Q^2$ particularly preferably represents hydrogen or $C_1$-$C_4$-alkyl.

$Q^1$ and $Q^2$ together with the carbon atom to which they are attached particularly preferably represent a $C_3$-$C_6$-ring which is optionally monosubstituted by fluorine, methyl, methoxy or trifluoromethyl and in which optionally one methylene group may be replaced by oxygen.

G particularly preferably represents hydrogen (a) or represents one of the groups

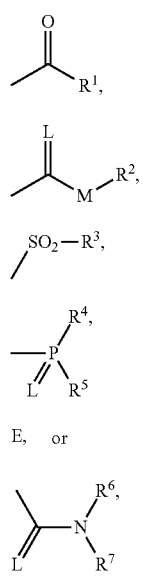

in which

E represents a metal ion or an ammonium ion,

L represents oxygen or sulphur and

M represents oxygen or sulphur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- or trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl, which is optionally mono- or disubstituted by fluorine, chorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or —$C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl.

$R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy.

$R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro.

$R^4$ and $R^5$ independently of one another particularly preferably represent $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl.

$R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-allyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, methyl, chlorine, bromine, ethyl, methoxy, ethoxy or trifluoromethyl, X very particularly preferably represents chlorine, bromine, methyl, ethyl, propyl, methoxy, ethoxy, propoxy, methoxyethoxy, ethoxyethoxy, trifluoromethyl, difluoromethoxy, trifluoromethoxy or cyano, Y in the 4-position very particularly preferably represents hydrogen, chlorine, bromine, trifluoromethyl or trifluoromethoxy, Z very particularly preferably represents hydrogen.

W also very particularly preferably represents hydrogen, chlorine, bromine, methyl or ethyl, X also very particularly preferably represents chlorine, bromine, methyl, ethyl, propyl, methoxy, trifluoromethyl, difluoromethoxy or cyano, Y also in the 4-position very particularly preferably represents the radical

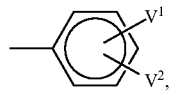

Z also very particularly preferably represents hydrogen, $V^1$ also very particularly preferably represents fluorine, chlorine, methyl, methoxy, trifluoromethyl or trifluoromethoxy, $V^2$ also very particularly preferably represents hydrogen, fluorine, chlorine, methyl, methoxy or trifluoromethyl.

W likewise very particularly preferably represents hydrogen, chlorine or methyl, X likewise very particularly preferably represents chlorine, methyl or trifluoromethyl, Y likewise in the 5-position very particularly preferably represents the radical

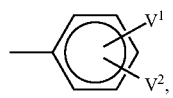

Z likewise in the 4-position very particularly preferably represents hydrogen or methyl, $V^1$ likewise very particularly preferably represents fluorine, chlorine, methyl, methoxy, trifluoromethyl or trifluoromethoxy, $V^2$ likewise very particularly preferably represents hydrogen, fluorine, chlorine, methyl, methoxy or trifluoromethyl.

W moreover very particularly preferably represents hydrogen, methyl, ethyl, methoxy, ethoxy, chlorine or bromine, X moreover very particularly preferably represents chlorine, bromine, methyl, ethyl, propyl, methoxy, ethoxy, propoxy, methoxyethoxy, ethoxyethoxy, trifluoromethyl, difluoromethoxy, trifluoromethoxy or cyano, Y moreover in the 4-position very particularly preferably represents methyl or ethyl, Z moreover very particularly preferably represents hydrogen.

W furthermore very particularly preferably represents hydrogen, chlorine, bromine, methyl or ethyl, X furthermore very particularly preferably represents chlorine, bromine, methyl, methoxy, trifluoromethyl, difluoromethoxy or trifluoromethoxy, Y furthermore in the 4-position very particularly preferably represents hydrogen, chlorine, bromine, methyl or ethyl, Z furthermore in the 3- or 5-position very particularly preferably represents fluorine, chlorine, bromine, methyl, ethyl, trifluoromethyl or trifluoromethoxy.

A very particularly preferably represents —CH$_2$—, —CHCH$_3$—, —CH$_2$—CH$_2$—, —CH$_2$—CHCH$_3$—, —CH$_2$—CH$_2$—CH$_2$—.

B very particularly preferably represents hydrogen, methyl, ethyl, propyl, isopropyl, butyl, isobutyl, C$_2$-C$_4$-alkenyl, methoxy, ethoxy, propoxy, isopropoxy, butoxy, isobutoxy, methoxyethoxy, ethoxyethoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen.

D very particularly preferably represents NH or oxygen.

$Q^1$ very particularly preferably represents hydrogen, methyl, ethyl, propyl, isopropyl, cyclopropyl, cyclopentyl or cyclohexyl.

$Q^2$ very particularly preferably represents hydrogen, methyl or ethyl.

$Q^1$ and $Q^2$ together with the carbon atom to which they are attached very particularly preferably represent cyclopropyl, cyclopentyl or cyclohexyl.

G very particularly preferably represents hydrogen (a) or represents one of the groups

(b)

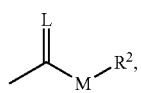

(c)

(d)

(e)

E, or (f)

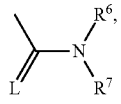

(g)

in which

E represents a metal ion or an ammonium ion,

L represents oxygen or sulphur and

M represents oxygen or sulphur, $R^1$ very particularly preferably represents C$_1$-C$_{10}$-alkyl, C$_2$-C$_{10}$-alkenyl, C$_1$-C$_4$-alkoxy-C$_1$-C$_2$-alkyl, C$_1$-C$_4$-alkylthio-C$_1$-C$_2$-alkyl, each of which is optionally mono- to trisubstituted by fluorine or chlorine, or represents C$_3$-C$_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, i-propyl, methoxy, ethoxy, trifluoromethyl or trifluoromethoxy, represents furanyl, thienyl or pyridyl, each of which is optionally monosubstituted by chlorine, bromine or methyl.

$R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl, or represents phenyl or benzyl, each of which is optionally mono- or disubstituted by fluorine, chlorine, cyano, nitro, methyl, ethyl, methoxy, trifluoromethyl or trifluoromethoxy.

$R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro.

$R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy.

$R^6$ and $R^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulphur.

W especially preferably represents hydrogen, methyl, ethyl, chlorine or bromine (in particular hydrogen, methyl, ethyl or chlorine), X especially preferably represents chlorine, bromine, methyl, ethyl, propyl, methoxy, ethoxy, propoxy, methoxyethoxy, cyclopropylmethyloxy, trifluoromethyl or difluoromethoxy (in particular chlorine, bromine, ethyl, methoxy or ethoxy), Y in the 4-position especially preferably represents hydrogen, chlorine, bromine, trifluoromethyl or trifluoromethoxy (in particular chlorine or bromine), Z especially preferably represents hydrogen, A especially preferably represents —$CH_2$—, —$CHCH_3$— or —$CH_2$—$CH_2$— (in particular —$CH_2$— or —$CH_2$—$CH_2$—), B especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, cyclopentyl or cyclohexyl (in particular hydrogen, methyl, ethyl, propyl or methoxy), D especially preferably represents NH, $Q^1$ especially preferably represents hydrogen or methyl (in particular hydrogen), $Q^2$ especially preferably represents hydrogen or methyl (in particular hydrogen), G especially preferably represents hydrogen (a) or represents one of the groups

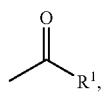
(b)

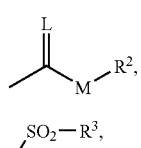
(c)

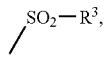
(d)

in which L represents oxygen and

M represents oxygen or sulphur (in particular oxygen), $R^1$ especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl, represents phenyl which is optionally monosubstituted by fluorine, chlorine, bromine, cyano, nitro, methyl, methoxy, trifluoromethyl or trifluoromethoxy, represents furanyl, thienyl or pyridyl, each of which is optionally monosubstituted by chlorine or methyl (in particular $C_1$-$C_6$-alkyl, $C_1$-$C_2$-alkoxy-$C_1$-$C_2$-alkyl, cyclopropyl or in each case chlorine-substituted phenyl or thienyl), $R^2$ especially preferably represents $C_1$-$C_6$-alkyl, $C_2$-$C_6$-alkenyl or $C_1$-$C_2$-alkoxy-$C_2$-$C_3$-alkyl, represents cyclopentyl or cyclohexyl, or represents phenyl or benzyl, each of which is optionally monosubstituted by fluorine, chlorine, cyano, nitro, methyl, methoxy, trifluoromethyl or trifluoromethoxy (in particular $C_1$-$C_8$-alkyl, $C_2$-$C_6$-alkenyl or benzyl).

$R^3$ especially preferably represents methyl-substituted phenyl.

W also especially preferably represents hydrogen, chlorine, bromine, methyl or ethyl, X also especially preferably represents chlorine, bromine, methyl, ethyl, propyl, methoxy, trifluoromethyl, difluoromethoxy or cyano, Y in the 4-position also especially preferably represents the radical

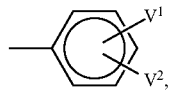

Z also especially preferably represents hydrogen, $V^1$ also especially preferably represents fluorine, chlorine, methyl, methoxy, trifluoromethyl or trifluoromethoxy, $V^2$ also especially preferably represents hydrogen, fluorine, chlorine, methyl, methoxy or trifluoromethyl, A also especially preferably represents —$CH_2$—, —$CHCH_3$— or —$CH_2$—$CH_2$—, B also especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, D also especially preferably represents NH, Q¹ also especially preferably represents hydrogen or methyl, Q² also especially preferably represents hydrogen or methyl, G also especially preferably represents hydrogen (a) or represents one of the groups

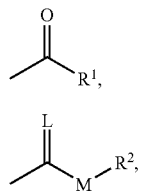

in which
L represents oxygen and
M represents oxygen or sulphur,

R¹ also especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl,
   represents phenyl which is optionally monosubstituted by fluorine, chlorine, bromine, cyano, nitro, methyl, methoxy, trifluoromethyl or trifluoromethoxy,
   represents furanyl, thienyl or pyridyl, each of which is optionally monosubstituted by chlorine or methyl, R² also especially preferably represents $C_1$-$C_8$-alkyl, $C_2$-$C_6$-alkenyl or $C_1$-$C_2$-alkoxy-$C_2$-$C_3$-alkyl,
   represents cyclopentyl or cyclohexyl,
   or represents phenyl or benzyl, each of which is optionally monosubstituted by fluorine, chlorine, cyano, nitro, methyl, methoxy, trifluoromethyl or trifluoromethoxy.

W likewise especially preferably represents hydrogen or methyl (in particular hydrogen), X likewise especially preferably represents chlorine or methyl (in particular methyl), Y in the 5-position likewise especially preferably represents the radical

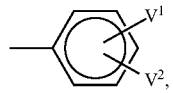

Z in the 4-position likewise especially preferably represents hydrogen or methyl (in particular hydrogen), V¹ likewise especially preferably represents fluorine, chlorine, methyl, methoxy, trifluoromethyl or trifluoromethoxy, V² likewise especially preferably represents hydrogen, fluorine, chlorine, methyl, methoxy or trifluoromethyl (Y represents in particular chlorine-substituted phenyl), A likewise especially preferably represents —CH₂—, —CHCH₃— or —CH₂—CH₂— (in particular —CH₂—), B likewise especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro (in particular propyl), D likewise especially preferably represents NH, Q¹ likewise especially preferably represents hydrogen or methyl (in particular hydrogen), Q² likewise especially preferably represents hydrogen or methyl (in particular hydrogen), G likewise especially preferably represents hydrogen (a) or represents one of the groups

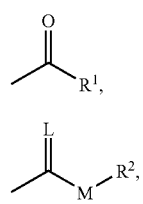

(in particular hydrogen),
in which
L represents oxygen and
M represents oxygen or sulphur, R¹ likewise especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl,
   represents phenyl which is optionally monosubstituted by fluorine, chlorine, bromine, cyano, nitro, methyl, methoxy, trifluoromethyl or trifluoromethoxy,
   represents furanyl, thienyl or pyridyl, each of which is optionally monosubstituted by chlorine or methyl, R¹ likewise especially preferably represents $C_1$-$C_8$-alkyl, $C_2$-$C_6$-alkenyl or $C_1$-$C_2$-alkoxy-$C_2$-$C_3$-alkyl,
   represents cyclopentyl or cyclohexyl,
   or represents phenyl or benzyl, each of which is optionally monosubstituted by fluorine, chlorine, cyano, nitro, methyl, methoxy, trifluoromethyl or trifluoromethoxy.

W moreover especially preferably represents hydrogen, methyl, ethyl, chlorine or bromine (in particular methyl, ethyl, chlorine or bromine), X moreover especially preferably represents chlorine, bromine, methyl, ethyl, propyl, methoxy, ethoxy, propoxy, H₃CO—(CH₂)₂—O, cyclopropylmethoxy, trifluoromethyl or difluoromethoxy (in particular chlorine, bromine, methyl, ethyl, methoxy or H₃CO—(CH₂)₂—O)), Y moreover especially preferably in the 4-position represents methyl, Z moreover especially preferably represents hydrogen, A moreover especially preferably represents —CH₂—, —CHCH₃— or —CH₂—CH₂— (in particular —CH₂— or —CH₂—CH₂—), B moreover especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen (in particular hydrogen, methyl, ethyl, propyl, isopropyl, methoxy or cyclopropyl), $Q^1$ moreover especially preferably represents hydrogen or methyl, $Q^2$ moreover especially preferably represents hydrogen or methyl, D moreover especially preferably represents NH, G moreover especially preferably represents hydrogen (a) or represents one of the groups

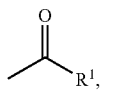 (b)

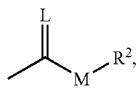 (c)

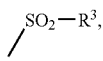 (d)

 (f)

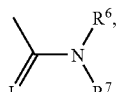 (g)

in which
E represents an ammonium ion,
  L represents oxygen or sulphur and
  M represents oxygen or sulphur,
$R^1$ moreover especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl,
  represents phenyl which is optionally monosubstituted by fluorine, chlorine, bromine, cyano, nitro, methyl, methoxy, trifluoromethyl or trifluoromethoxy,
  represents

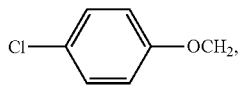

represents furanyl, thienyl or pyridyl, each of which is optionally monosubstituted by chlorine or methyl (in particular represents C1-C6-alkyl, which is optionally monosubstituted by chlorine represents C1-C2-alkoxy-C1-C2-alkyl, cyclopropyl, represents chlorine-substituted phenyl, pyridyl,

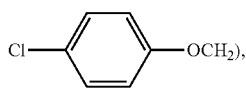

thienyl or
$R^2$ moreover especially preferably represents $C_1$-$C_{10}$-alkyl, $C_2$-$C_{10}$-alkenyl or $C_1$-$C_2$-alkoxy-$C_2$-$C_4$-alkyl, represents cyclopentyl or cyclohexyl,
  or represents phenyl or benzyl, each of which is optionally monosubstituted by fluorine, chlorine, cyano, nitro, methyl, methoxy, trifluoromethyl or trifluoromethoxy (in particular $C_1$-$C_{10}$-alkyl, $C_2$-$C_{10}$-alkenyl or benzyl), $R^3$ moreover especially preferably represents methyl or methyl-substituted phenyl, $R^6$ and $R^7$ together moreover especially preferably represent a $C_5$-$C_6$-alkylene radical in which one methylene group represents oxygen.

W furthermore especially preferably represents hydrogen, methyl, chlorine or bromine (in particular hydrogen or methyl), X furthermore especially preferably represents chlorine, bromine, methyl, methoxy or trifluoromethyl (in particular methyl), Y in the 4-position furthermore especially preferably represents hydrogen, chlorine, bromine or methyl (in particular hydrogen or methyl), Z in the 3- or 5-position furthermore especially preferably represents chlorine, bromine, methyl, ethyl, trifluoromethyl or trifluoromethoxy (in particular methyl), A furthermore especially preferably represents —CH$_2$—, —CHCH$_3$— or —CH$_2$—CH$_2$— (in particular —CH$_2$—), B furthermore especially preferably represents hydrogen, methyl, ethyl, propyl, isopropyl, $C_2$-$C_4$-alkenyl, methoxy, ethoxy, propoxy, isopropoxy, butoxy, isobutoxy, cyclopropyl, represents phenyl which is optionally mono- or disubstituted by fluorine, chlorine, bromine, methyl, methoxy, trifluoromethyl, trifluoromethoxy, cyano or nitro (in particular hydrogen, methyl, ethyl or cyclopropyl), D furthermore especially preferably represents NH, $Q^1$ furthermore especially preferably represents hydrogen or methyl (in particular hydrogen), $Q^2$ furthermore especially preferably represents hydrogen or methyl (in particular hydrogen), G furthermore especially preferably represents hydrogen (a) or represents one of the groups

 (b)

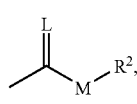 (c)

(in particular hydrogen or the group (c)),
in which
L represents oxygen and
M represents oxygen or sulphur (in particular oxygen), $R^1$ furthermore especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl each of which is optionally mono- to trisubstituted by fluorine or chlorine, or represents cyclopropyl, cyclopentyl or cyclohexyl,
  represents phenyl which is optionally monosubstituted by fluorine, chlorine, bromine, cyano, nitro, methyl, methoxy, trifluoromethyl or trifluoromethoxy,
  represents furanyl, thienyl or pyridyl, each of which is optionally monosubstituted by chlorine or methyl, $R^2$ furthermore especially preferably represents $C_1$-$C_8$-alkyl, $C_2$-$C_6$-alkenyl or $C_1$-$C_2$-alkoxy-$C_2$-$C_3$-alkyl, represents cyclopentyl or cyclohexyl, or represents phenyl or benzyl, each of which is optionally monosubstituted by fluorine, chlorine, cyano, nitro, methyl, methoxy, trifluoromethyl or trifluoromethoxy (in particular $C_1$-$C_8$-alkyl).

W additionally especially preferably represents hydrogen, methyl, ethyl, chlorine or bromine (in particular hydrogen, chlorine, methyl or ethyl), X additionally especially preferably represents chlorine, bromine, methyl, ethyl, propyl, methoxy, ethoxy, propoxy, trifluoromethyl, difluoromethoxy or cyano (in particular chlorine, bromine, methyl, ethyl or trifluoromethyl), Y in the 4-position additionally especially preferably represents hydrogen, chlorine, bromine, methoxy, trifluoromethyl or trifluoromethoxy (in particular hydrogen, chlorine, bromine or methoxy), Z additionally especially preferably represents hydrogen, A additionally especially preferably represents —$CH_2$—, B additionally especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, cyclopentyl or cyclohexyl (in particular hydrogen or propyl), D additionally especially preferably represents oxygen, $Q^1$ additionally especially preferably represents hydrogen or methyl (in particular hydrogen), $Q^2$ additionally especially preferably represents hydrogen or methyl (in particular hydrogen), G especially preferably represents hydrogen (a) or represents one of the groups

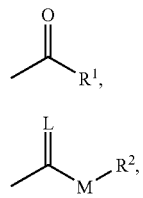

(b)

(c)

(in particular hydrogen or the group (b)),
in which
L represents oxygen and
M represents oxygen or sulphur, $R^1$ additionally especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which may be mono- to trisubstituted by fluorine or chlorine, or represents cyclopropyl, cyclopentyl or cyclohexyl,
represents phenyl which is optionally monosubstituted by fluorine, chlorine, bromine, cyano, nitro, methyl, methoxy, trifluoromethyl or trifluoromethoxy,
represents furanyl, thienyl or pyridyl, each of which is optionally monosubstituted by chlorine or methyl (in particular $C_1$-$C_6$-alkyl), $R^2$ additionally especially preferably represents $C_1$-$C_8$-alkyl, $C_2$-$C_6$-alkenyl or $C_1$-$C_2$-alkoxy-$C_2$-$C_3$-alkyl,
represents cyclopentyl or cyclohexyl,
or represents phenyl or benzyl, each of which is optionally monosubstituted by fluorine, chlorine, cyano, nitro, methyl, methoxy, trifluoromethyl or trifluoromethoxy.

W additionally also especially preferably represents hydrogen, chlorine, bromine, methyl or ethyl (in particular methyl), X additionally also especially preferably represents chlorine, bromine, methyl, ethyl, propyl, methoxy, trifluoromethyl, difluoromethoxy or cyano (in particular methyl or ethyl), Y additionally also especially preferably in the 4-position represents the radical

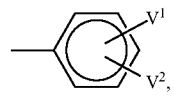

Z additionally also especially preferably represents hydrogen, $V^1$ additionally also especially preferably represents fluorine, chlorine, methyl, methoxy, trifluoromethyl or trifluoromethoxy, $V^2$ additionally also especially preferably represents hydrogen, fluorine, chlorine, methyl, methoxy or trifluoromethyl, Y additionally also especially preferably represents

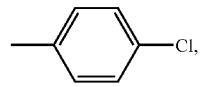

A additionally also especially preferably represents —$CH_2$—,

B additionally also especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro (in particular hydrogen or methyl), D additionally also especially preferably represents oxygen, $Q^1$ additionally also especially preferably represents hydrogen or methyl (in particular hydrogen), $Q^2$ additionally also especially preferably represents hydrogen or methyl (in particular hydrogen), G additionally also especially preferably represents hydrogen (a) or represents one of the groups

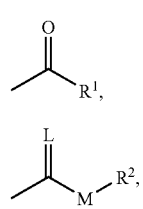

(b)

(c)

(in particular hydrogen),
in which
L represents oxygen and
M represents oxygen or sulphur, $R^1$ additionally also especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl, represents phenyl which is optionally monosubstituted by fluorine, chlorine, bromine, cyano, nitro, methyl, methoxy, trifluoromethyl or trifluoromethoxy, represents furanyl, thienyl or pyridyl, each of which is optionally monosubstituted by chlorine or methyl, $R^2$ additionally also especially preferably represents $C_1$-$C_8$-alkyl, $C_2$-$C_6$-alkenyl or $C_1$-$C_2$-alkoxy-$C_2$-$C_3$-alkyl, represents cyclopentyl or cyclohexyl, or represents phenyl or benzyl, each of which is optionally monosubstituted by fluorine, chlorine, cyano, nitro, methyl, methoxy, trifluoromethyl or trifluoromethoxy (in particular $C_1$-$C_8$-alkyl).

W additionally likewise especially preferably represents hydrogen or methyl,

X additionally likewise especially preferably represents chlorine or methyl,

Y additionally likewise especially preferably in the 5-position represents the radical

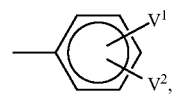

Z in the 4-position additionally likewise especially preferably represents hydrogen or methyl, $V^1$ additionally likewise especially preferably represents fluorine, chlorine, methyl, methoxy, trifluoromethyl or trifluoromethoxy, $V^2$ additionally likewise especially preferably represents hydrogen, fluorine, chlorine, methyl, methoxy or trifluoromethyl, Y additionally likewise especially preferably represents

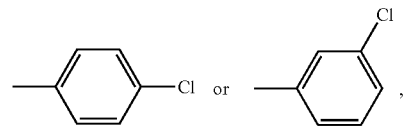

A additionally likewise especially preferably represents —CH$_2$—,

B additionally likewise especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro (in particular hydrogen), D additionally likewise especially preferably represents oxygen, $Q^1$ additionally likewise especially preferably represents hydrogen or methyl (in particular hydrogen), $Q^2$ additionally likewise especially preferably represents hydrogen or methyl (in particular hydrogen), G additionally likewise especially preferably represents hydrogen (a) or represents one of the groups

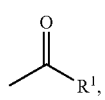

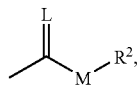

in which

L represents oxygen and

M represents oxygen or sulphur (in particular oxygen), $R^1$ additionally likewise especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl, represents phenyl which is optionally monosubstituted by fluorine, chlorine, bromine, cyano, nitro, methyl, methoxy, trifluoromethyl or trifluoromethoxy, represents furanyl, thienyl or pyridyl, each of which is optionally monosubstituted by chlorine or methyl (in particular $C_1$-$C_6$-alkyl), $R^1$ additionally likewise especially preferably represents $C_1$-$C_8$-alkyl, $C_2$-$C_6$-alkenyl or $C_1$-$C_2$-alkoxy-$C_2$-$C_3$-alkyl, represents cyclopentyl or cyclohexyl, or represents phenyl or benzyl, each of which is optionally monosubstituted by fluorine, chlorine, cyano, nitro, methyl, methoxy, trifluoromethyl or trifluoromethoxy (in particular $C_1$-$C_8$-alkyl).

W additionally moreover especially preferably represents hydrogen, methyl, chlorine or bromine, X additionally moreover especially preferably represents chlorine, bromine, methyl, ethyl, propyl, methoxy, ethoxy, propoxy, trifluoromethyl, difluoromethoxy or cyano (in particular chlorine, bromine, methyl or methoxy), Y in the 4-position additionally moreover especially preferably represents methyl or ethyl, Z additionally moreover especially preferably represents hydrogen, A additionally moreover especially preferably represents —CH$_2$—, B additionally moreover especially preferably represents hydrogen, methyl, ethyl, propyl, isopropyl, $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen (in particular hydrogen or propyl), $Q^1$ additionally moreover especially preferably represents hydrogen or methyl (in particular hydrogen), $Q^2$ additionally moreover especially preferably represents hydrogen or methyl (in particular hydrogen), D additionally moreover especially preferably represents oxygen, G additionally moreover especially preferably represents hydrogen (a) or represents eine one of the groups

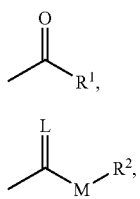

(b)

(c)

in which
L represents oxygen and
M represents oxygen or sulphur (in particular oxygen),
R$^1$ additionally moreover especially preferably represents C$_1$-C$_6$-alkyl, C$_2$-C$_6$-alkenyl, C$_1$-C$_2$-alkoxy-C$_1$-C$_2$-alkyl, C$_1$-C$_2$-alkylthio-C$_1$-C$_2$-alkyl, each of which is optionally mono- to trisubstituted by fluorine or chlorine, or represents cyclopropyl, cyclopentyl or cyclohexyl,
represents phenyl which is optionally monosubstituted by fluorine, chlorine, bromine, cyano, nitro, methyl, methoxy, trifluoromethyl or trifluoromethoxy,
represents furanyl, thienyl or pyridyl, each of which is optionally monosubstituted by chlorine or methyl (in particular C$_1$-C$_6$-alkyl),
R$^2$ additionally moreover especially preferably represents C$_1$-C$_{10}$-alkyl, C$_2$-C$_{10}$-alkenyl or C$_1$-C$_2$-alkoxy-C$_2$-C$_4$-alkyl,
represents cyclopentyl or cyclohexyl,
or represents phenyl or benzyl, each of which is optionally monosubstituted by fluorine, chlorine, cyano, nitro, methyl, methoxy, trifluoromethyl or trifluoromethoxy (in particular C$_1$-C$_{10}$-alkyl).
W additionally furthermore especially preferably represents hydrogen, methyl, chlorine or bromine (in particular hydrogen, chlorine or methyl),
X additionally furthermore especially preferably represents chlorine, bromine, methyl, methoxy or trifluoromethyl (in particular chlorine, bromine or methyl),
Y in the 4-position additionally furthermore especially preferably represents hydrogen, chlorine, bromine or methyl,
Z in the 3- or 5-position additionally furthermore especially preferably represents chlorine, fluorine, bromine, methyl, ethyl, trifluoromethyl or trifluoromethoxy (in particular fluorine, chlorine, bromine or methyl),
A additionally furthermore especially preferably represents —CH$_2$—,
B additionally furthermore especially preferably represents hydrogen, methyl, ethyl, propyl, isopropyl, C$_2$-C$_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl, in which optionally one methylene group is replaced by oxygen (in particular hydrogen or propyl),
Q$^1$ additionally furthermore especially preferably represents hydrogen or methyl (in particular hydrogen),
Q$^2$ additionally furthermore especially preferably represents hydrogen or methyl (in particular hydrogen),
D additionally furthermore especially preferably represents oxygen,
G additionally furthermore especially preferably represents hydrogen (a) or represents one of the groups

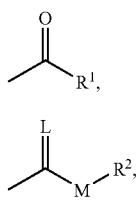

(b)

(c)

(in particular hydrogen),
in which
L represents oxygen and
M represents oxygen or sulphur,
R$^1$ additionally furthermore especially preferably represents C$_1$-C$_6$-alkyl, C$_2$-C$_6$-alkenyl, C$_1$-C$_2$-alkoxy-C$_1$-C$_2$-alkyl, C$_1$-C$_2$-alkylthio-C$_1$-C$_2$-alkyl, each of which is optionally mono- to trisubstituted by fluorine or chlorine, or represents cyclopropyl, cyclopentyl or cyclohexyl,
represents phenyl which is optionally monosubstituted by fluorine, chlorine, bromine, cyano, nitro, methyl, methoxy, trifluoromethyl or trifluoromethoxy,
represents furanyl, thienyl or pyridyl, each of which is optionally monosubstituted by chlorine or methyl,
R$^2$ additionally furthermore especially preferably represents C$_1$-C$_{10}$-alkyl, C$_2$-C$_{10}$-alkenyl or C$_1$-C$_2$-alkoxy-C$_2$-C$_4$-alkyl,
represents cyclopentyl or cyclohexyl,
or represents phenyl or benzyl, each of which is optionally monosubstituted by fluorine, chlorine, cyano, nitro, methyl, methoxy, trifluoromethyl or trifluoromethoxy.

The general or preferred radical definitions or illustrations given above can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Special preference according to the invention is given to the compounds of the formula (I) which contain a combination of the meanings given above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Optionally substituted radicals can, unless stated otherwise, be mono- or polysubstituted, where in the case of polysubstitution the substituents can be identical or different.

In addition to the compounds mentioned in the Preparation Examples, the following compounds of the formula (I-1-a) may be specifically mentioned:

TABLE 1

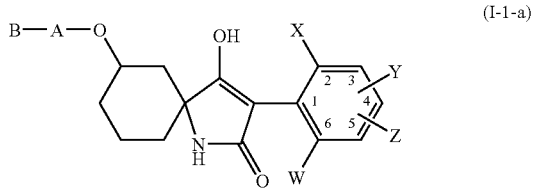

(I-1-a)

| A | B | X | W | Y | Z |
|---|---|---|---|---|---|
| $CH_2$ | H | $CH_3$ | H | H | H |
| $CH_2$ | H | Br | H | H | H |
| $CH_2$ | H | Cl | H | H | H |
| $CH_2$ | H | $CF_3$ | H | H | H |
| $CH_2$ | H | $OCH_3$ | H | H | H |
| $CH_2$ | H | Br | H | 4-Cl | H |
| $CH_2$ | H | Cl | H | 4-Br | H |
| $CH_2$ | H | Cl | H | 4-Cl | H |
| $CH_2$ | H | Cl | H | 4-$CH_3$ | H |
| $CH_2$ | H | $CH_3$ | H | 4-Cl | H |
| $CH_2$ | H | $CH_3$ | H | 4-$CH_3$ | H |
| $CH_2$ | H | Cl | Cl | H | H |
| $CH_2$ | H | Cl | $OCH_3$ | H | H |
| $CH_2$ | H | Cl | $CH_3$ | H | H |
| $CH_2$ | H | Cl | $OC_2H_5$ | H | H |
| $CH_2$ | H | $OCH_3$ | $OCH_3$ | H | H |
| $CH_2$ | H | $CH_3$ | $CH_3$ | H | H |
| $CH_2$ | H | Br | $CH_3$ | 4-Br | H |
| $CH_2$ | H | Cl | Cl | 4-$CH_3$ | H |
| $CH_2$ | H | $CH_3$ | Br | 4-$CH_3$ | H |
| $CH_2$ | H | $CH_3$ | Cl | 4-$CH_3$ | H |
| $CH_2$ | H | $OCH_3$ | $CH_3$ | 4-$CH_3$ | H |
| $CH_2$ | H | $OC_2H_5$ | $CH_3$ | 4-$CH_3$ | H |
| $CH_2$ | H | $OC_3H_7$ | $CH_3$ | 4-$CH_3$ | H |
| $CH_2$ | H | $CH_3$ | $CH_3$ | 4-$CH_3$ | H |
| $CH_2$ | H | Br | Br | 4-$CH_3$ | H |
| $CH_2$ | H | $CH_3$ | $CH_3$ | 4-Br | H |
| $CH_2$ | H | $C_2H_5$ | $CH_3$ | H | H |
| $CH_2$ | H | $C_2H_5$ | $C_2H_5$ | H | H |
| $CH_2$ | H | $OCH_3$ | $C_2H_5$ | 4-$CH_3$ | H |
| $CH_2$ | H | $CH_3$ | $CH_3$ | 4-$OCH_3$ | H |
| $CH_2$ | H | Br | Cl | 4-$CH_3$ | H |
| $CH_2$ | H | Br | $CH_3$ | 4-Cl | H |
| $CH_2$ | H | Cl | $CH_3$ | 4-Br | H |
| $CH_2$ | H | $CH_3$ | $CH_3$ | 4-Cl | H |
| $CH_2$ | H | $C_2H_5$ | $CH_3$ | 4-$CH_3$ | H |
| $CH_2$ | H | $C_2H_5$ | $CH_3$ | 4-$C_2H_5$ | H |
| $CH_2$ | H | $C_2H_5$ | $C_2H_5$ | 4-$CH_3$ | H |
| $CH_2$ | H | $C_2H_5$ | $C_2H_5$ | 4-$C_2H_5$ | H |
| $CH_2$ | H | $C_2H_5$ | $CH_3$ | 4-Cl | H |
| $CH_2$ | H | $C_2H_5$ | $C_2H_5$ | 4-Cl | H |
| $CH_2$ | H | $C_2H_5$ | $CH_3$ | 4-Br | H |
| $CH_2$ | H | $C_2H_5$ | $C_2H_5$ | 4-Br | H |
| $CH_2$ | H | $C_2H_5$ | Cl | 4-$CH_3$ | H |
| $CH_2$ | H | $C_2H_5$ | Br | 4-$CH_3$ | H |
| $CH_2$ | H | $C_2H_5$ | Cl | 4-Cl | H |
| $CH_2$ | H | $C_2H_5$ | Br | 4-Br | H |
| $CH_2$ | H | $C_2H_5$ | Cl | 4-Br | H |
| $CH_2$ | H | $C_2H_5$ | Br | 4-Cl | H |
| $CH_2$ | H | $OCH_3$ | $CH_3$ | 4-Cl | H |
| $CH_2$ | H | $OCH_3$ | $C_2H_5$ | 4-Cl | H |
| $CH_2$ | H | $OC_2H_5$ | $CH_3$ | 4-Cl | H |
| $CH_2$ | H | $OC_2H_5$ | $C_2H_5$ | 4-Cl | H |
| $CH_2$ | H | Cl | $OCH_3$ | 4-$CH_3$ | H |
| $CH_2$ | H | Cl | $OC_2H_5$ | 4-$CH_3$ | H |
| $CH_2$ | H | Cl | Cl | 4-Cl | H |
| $CH_2$ | H | Cl | H | 4-Cl | 5-Cl |
| $CH_2$ | H | $CH_3$ | H | 4-$CH_3$ | 5-$CH_3$ |
| $CH_2$ | H | Br | H | 4-Cl | 5-$CH_3$ |
| $CH_2$ | H | Br | H | 4-$CH_3$ | 5-$CH_3$ |
| $CH_2$ | H | Cl | H | 4-Br | 5-$CH_3$ |
| $CH_2$ | H | Cl | H | 4-Cl | 5-$CH_3$ |
| $CH_2$ | H | $CH_3$ | H | 4-Br | 5-$CH_3$ |
| $CH_2$ | H | Cl | H | 4-$CH_3$ | 5-Cl |
| $CH_2$ | H | $CH_3$ | H | H | 5-$CH_3$ |
| $CH_2$ | H | Cl | H | H | 5-$CH_3$ |
| $CH_2$ | H | Br | H | H | 5-$CH_3$ |

TABLE 1-continued

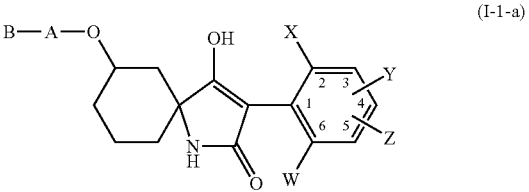

(I-1-a)

| A | B | X | W | Y | Z |
|---|---|---|---|---|---|
| $CH_2$ | H | $CH_3$ | H | H | 5-Cl |
| $CH_2$ | H | $CH_3$ | H | H | 5-Br |
| $CH_2$ | H | $CH_3$ | $CH_3$ | 4-$CH_3$ | 5-$CH_3$ |
| $CH_2$ | H | $CH_3$ | $CH_3$ | 4-$CH_3$ | 5-Cl |
| $CH_2$ | H | $CH_3$ | $CH_3$ | 4-$CH_3$ | 5-Br |
| $CH_2$ | H | $CH_3$ | $CH_3$ | H | 3-Cl |
| $CH_2$ | H | $CH_3$ | $CH_3$ | H | 3-Br |
| $CH_2$ | H | Cl | Cl | H | 3-Br |
| $CH_2$ | H | $CH_3$ | $CH_3$ | 4-(4-Cl—$C_6H_4$) | H |
| $CH_2$ | H | $C_2H_5$ | $CH_3$ | 4-(4-Cl—$C_6H_4$) | H |
| $CH_2$ | H | $C_2H_5$ | $C_2H_5$ | 4-(4-Cl—$C_6H_4$) | H |
| $CH_2$ | H | Cl | $CH_3$ | 4-(4-Cl—$C_6H_4$) | H |
| $CH_2$ | H | Cl | $C_2H_5$ | 4-(4-Cl—$C_6H_4$) | H |
| $CH_2$ | H | $CH_3$ | H | 5-(4-Cl—$C_6H_4$) | H |
| $CH_2$ | H | $CH_3$ | $CH_3$ | 5-(4-Cl—$C_6H_4$) | H |
| $CH_2$ | H | $CH_3$ | H | 5-(4-Cl—$C_6H_4$) | 4-$CH_3$ |
| $CH_2$ | H | $CH_3$ | $CH_3$ | 5-(4-Cl—$C_6H_4$) | 4-$CH_3$ |
| $CH_2$ | H | Cl | H | 5-(4-Cl—$C_6H_4$) | H |
| $CH_2$ | H | O—$(CH_2)_2$—$OCH_3$ | $CH_3$ | 4-Cl | H |
| $CH_2$ | H | O—$(CH_2)_2$—$OCH_3$ | $C_2H_5$ | 4-Cl | H |
| $CH_2$ | H | O—$CH_3$ | $CH_3$ | 4-Br | H |
| $CH_2$ | H | O—$CH_3$ | $C_2H_5$ | 4-Br | H |
| $CH_2$ | H | O—$C_2H_5$ | $CH_3$ | 4-Br | H |
| $CH_2$ | H | O—$C_2H_5$ | $C_2H_5$ | 4-Br | H |

TABLE 2

A, W, X, Y and Z are as shown in Table 1
B = $CH_3$

TABLE 3

A, W, X, Y and Z are as shown in Table 1
B = $C_2H_5$

TABLE 4

A, W, X, Y and Z are as shown in Table 1
B = $C_3H_7$

TABLE 5

A, W, X, Y and Z are as shown in Table 1
B = i-$C_3H_7$

TABLE 6

A, W, X, Y and Z are as shown in Table 1

B = △

TABLE 7

A, W, X, Y and Z are as shown in Table 1

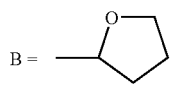

TABLE 8

A, W, X, Y and Z are as shown in Table 1
A = —CH₂—CH₂—; B = OCH₃

TABLE 9

A, W, X, Y and Z are as shown in Table 1
A = —CH₂—CH₂—; B = OC₂H₅

In addition to the compounds mentioned in the Preparation Examples the following compounds of the formula (I-2-a) may be specifically mentioned:

TABLE 10

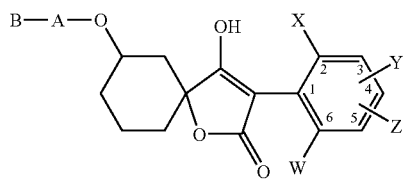
(I-2-a)

| A | B | X | W | Y | Z |
|---|---|---|---|---|---|
| CH₂ | H | CH₃ | H | H | H |
| CH₂ | H | Br | H | H | H |
| CH₂ | H | Cl | H | H | H |
| CH₂ | H | CF₃ | H | H | H |
| CH₂ | H | OCH₃ | H | H | H |
| CH₂ | H | Br | H | 4-Cl | H |
| CH₂ | H | Cl | H | 4-Br | H |
| CH₂ | H | Cl | H | 4-Cl | H |
| CH₂ | H | Cl | H | 4-CH₃ | H |
| CH₂ | H | CH₃ | H | 4-Cl | H |
| CH₂ | H | CH₃ | H | 4-CH₃ | H |
| CH₂ | H | Cl | Cl | H | H |
| CH₂ | H | Cl | OCH₃ | H | H |
| CH₂ | H | Cl | CH₃ | H | H |
| CH₂ | H | Cl | OC₂H₅ | H | H |
| CH₂ | H | OCH₃ | OCH₃ | H | H |
| CH₂ | H | CH₃ | CH₃ | H | H |
| CH₂ | H | C₂H₅ | CH₃ | H | H |
| CH₂ | H | C₂H₅ | C₂H₅ | H | H |
| CH₂ | H | Br | CH₃ | 4-Br | H |
| CH₂ | H | Cl | CH₃ | 4-CH₃ | H |
| CH₂ | H | CH₃ | Br | 4-CH₃ | H |
| CH₂ | H | CH₃ | Cl | 4-CH₃ | H |
| CH₂ | H | OCH₃ | CH₃ | 4-CH₃ | H |
| CH₂ | H | OCH₃ | C₂H₅ | 4-CH₃ | H |
| CH₂ | H | OC₂H₅ | CH₃ | 4-CH₃ | H |
| CH₂ | H | OC₃H₇ | CH₃ | 4-CH₃ | H |
| CH₂ | H | CH₃ | CH₃ | 4-CH₃ | H |
| CH₂ | H | Br | Br | 4-CH₃ | H |
| CH₂ | H | Cl | Cl | 4-CH₃ | H |
| CH₂ | H | CH₃ | CH₃ | 4-Br | H |
| CH₂ | H | CH₃ | CH₃ | 4-OCH₃ | H |
| CH₂ | H | Br | Cl | 4-CH₃ | H |
| CH₂ | H | Br | CH₃ | 4-Cl | H |
| CH₂ | H | Cl | CH₃ | 4-Br | H |
| CH₂ | H | CH₃ | CH₃ | 4-Cl | H |
| CH₂ | H | C₂H₅ | CH₃ | 4-CH₃ | H |
| CH₂ | H | C₂H₅ | C₂H₅ | 4-CH₃ | H |

TABLE 10-continued

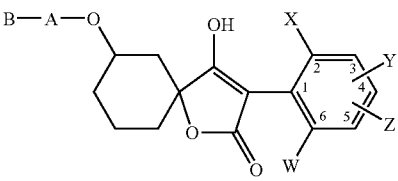
(I-2-a)

| A | B | X | W | Y | Z |
|---|---|---|---|---|---|
| CH₂ | H | C₂H₅ | CH₃ | 4-C₂H₅ | H |
| CH₂ | H | C₂H₅ | C₂H₅ | 4-C₂H₅ | H |
| CH₂ | H | C₂H₅ | CH₃ | 4-Cl | H |
| CH₂ | H | C₂H₅ | C₂H₅ | 4-Cl | H |
| CH₂ | H | C₂H₅ | CH₃ | 4-Br | H |
| CH₂ | H | C₂H₅ | C₂H₅ | 4-Br | H |
| CH₂ | H | C₂H₅ | Cl | 4-CH₃ | H |
| CH₂ | H | C₂H₅ | Br | 4-CH₃ | H |
| CH₂ | H | C₂H₅ | Cl | 4-Cl | H |
| CH₂ | H | C₂H₅ | Br | 4-Br | H |
| CH₂ | H | C₂H₅ | Cl | 4-Br | H |
| CH₂ | H | C₂H₅ | Br | 4-Cl | H |
| CH₂ | H | OCH₃ | CH₃ | 4-Cl | H |
| CH₂ | H | OCH₃ | C₂H₅ | 4-Cl | H |
| CH₂ | H | OC₂H₅ | CH₃ | 4-Cl | H |
| CH₂ | H | OC₂H₅ | C₂H₅ | 4-Cl | H |
| CH₂ | H | Cl | OCH₃ | 4-CH₃ | H |
| CH₂ | H | Cl | OC₂H₅ | 4-CH₃ | H |
| CH₂ | H | CH₃ | CH₃ | 4-Cl | H |
| CH₂ | H | Cl | H | 4-Cl | 5-Cl |
| CH₂ | H | CH₃ | H | 4-CH₃ | 5-CH₃ |
| CH₂ | H | CH₃ | H | 4-Cl | 5-CH₃ |
| CH₂ | H | Br | H | 4-Cl | 5-CH₃ |
| CH₂ | H | Br | H | 4-CH₃ | 5-CH₃ |
| CH₂ | H | Cl | H | 4-Br | 5-CH₃ |
| CH₂ | H | Cl | H | 4-Cl | 5-CH₃ |
| CH₂ | H | CH₃ | H | 4-Br | 5-CH₃ |
| CH₂ | H | Cl | H | 4-CH₃ | 5-Cl |
| CH₂ | H | CH₃ | H | H | 5-CH₃ |
| CH₂ | H | Cl | H | H | 5-CH₃ |
| CH₂ | H | Br | H | H | 5-CH₃ |
| CH₂ | H | CH₃ | H | H | 5-Cl |
| CH₂ | H | CH₃ | H | H | 5-Br |
| CH₂ | H | CH₃ | CH₃ | 4-CH₃ | 5-CH₃ |
| CH₂ | H | CH₃ | CH₃ | 4-CH₃ | 5-Cl |
| CH₂ | H | CH₃ | CH₃ | 4-CH₃ | 5-Br |
| CH₂ | H | CH₃ | CH₃ | H | 3-Cl |
| CH₂ | H | CH₃ | CH₃ | H | 3-Br |
| CH₂ | H | Cl | Cl | H | 3-Br |
| CH₂ | H | CH₃ | CH₃ | 4-(4-Cl—C₆H₄) | H |
| CH₂ | H | C₂H₅ | CH₃ | 4-(4-Cl—C₆H₄) | H |
| CH₂ | H | C₂H₅ | C₂H₅ | 4-(4-Cl—C₆H₄) | H |
| CH₂ | H | Cl | CH₃ | 4-(4-Cl—C₆H₄) | H |
| CH₂ | H | Cl | C₂H₅ | 4-(4-Cl—C₆H₄) | H |
| CH₂ | H | CH₃ | H | 5-(4-Cl—C₆H₄) | H |
| CH₂ | H | CH₃ | CH₃ | 5-(4-Cl—C₆H₄) | H |
| CH₂ | H | CH₃ | H | 5-(4-Cl—C₆H₄) | 4-CH₃ |
| CH₂ | H | CH₃ | CH₃ | 5-(4-Cl—C₆H₄) | 4-CH₃ |
| CH₂ | H | Cl | H | 5-(4-Cl—C₆H₄) | H |

TABLE 11

A, W, X, Y and Z are as shown in Table 10
B = CH₃

TABLE 12

A, W, X, Y and Z are as shown in Table 10
B = C₂H₅

TABLE 13

A, W, X, Y and Z are as shown in Table 10
B = C₃H₇

TABLE 14

A, W, X, Y and Z are as shown in Table 10
B = i-C₃H₇

TABLE 15

A, W, X, Y and Z are as shown in Table 10

B = 

TABLE 16

A, W, X, Y and Z are as shown in Table 10

B = 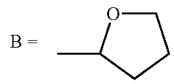

TABLE 17

W, X, Y and Z are as shown in Table 10
A = —CH₂—CH₂—; B = OCH₃

TABLE 18

W, X, Y and Z are as shown in Table 10
A = —CH₂—CH₂—; B = OC₂H₅

Preferred meanings of the groups mentioned above in connection with the compounds improving crop plant tolerance ("herbicide safeners") of the formulae (IIa), (IIb), (IIc), (IId) and (IIe) are defined hereinbelow.

m preferably represents the numbers 0, 1, 2, 3 or 4.

$A^1$ preferably represents one of the divalent heterocyclic groups outlined hereinbelow

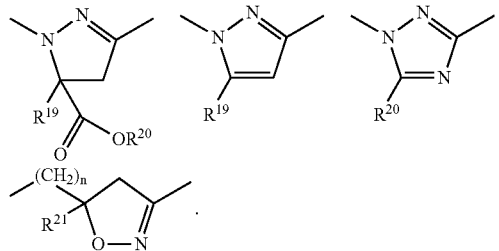

n preferably represents the numbers 0, 1, 2, 3 or 4.

$A^2$ preferably represents methylene or ethylene, each of which is optionally substituted by methyl, ethyl, methoxycarbonyl, ethoxycarbonyl or alkyloxycarbonyl.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents methyl, ethyl, n- or i-propyl, each of which is optionally substituted by fluorine, chlorine and/or bromine.

$R^{17}$ preferably represents hydrogen, or represents methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl.

$R^{18}$ preferably represents hydrogen, or represents methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl, or $R^{17}$ and $R^{18}$ together also represent one of the radicals —CH₂—O—CH₂—CH₂— and —CH₂—CH₂—O—CH₂—CH₂— which are optionally substituted by methyl, ethyl, furyl, phenyl, a fused benzene ring or by two substituents which, together with the carbon atom to which they are bonded, form a 5- or 6-membered carbocycle.

$R^{19}$ preferably represents hydrogen, cyano, fluorine, chlorine, bromine, or represents methyl, ethyl, n- or i-propyl, cyclopropyl, cyclobutyl, cyclopentyl, cyclohexyl or phenyl, each of which is optionally substituted by fluorine, chlorine and/or bromine.

$R^{20}$ preferably represents hydrogen, or represents methyl, ethyl, n- or i-propyl, n-, i-, s- or t-butyl, each of which is optionally substituted by hydroxyl, cyano, fluorine, chlorine, methoxy, ethoxy, n- or i-propoxy.

$R^{21}$ preferably represents hydrogen, cyano, fluorine, chlorine, bromine, or represents methyl, ethyl, n- or i-propyl, n-, i-, s- or t-butyl, cyclopropyl, cyclobutyl, cyclopentyl, cyclohexyl or phenyl, each of which is optionally substituted by fluorine, chlorine and/or bromine.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, 3 or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, or represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n-or i-propylamino, n-, i-, s- or t-butylamino, dimethylamino or diethylamino, each of which is optionally substituted by cyano, fluorine, chlorine, methoxy, ethoxy, n- or i-propoxy, or represents cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, each of which is optionally substituted by cyano, fluorine, chlorine, bromine, methyl, ethyl, n- or i-propyl.

$R^{25}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propynyl or butynyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl.

$R^{26}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propynyl or butynyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl, or represents phenyl which is optionally substituted by nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, or together with $R^{25}$ represents butane-1,4-diyl(trimethylene), pentane-1,5-diyl, 1-oxabutane-1,4diyl or 3-oxapentane-1,5-diyl, each of which is optionally substituted by methyl or ethyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in Table 19 below.

TABLE 19

Examples of the compounds of the formula (IIa)

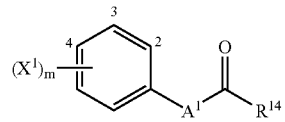

(IIa)

| Example No. | (Positions) $(X^1)_m$ | $A^1$ | $R^{14}$ |
|---|---|---|---|
| IIa-1 | (2) Cl, (4) Cl | 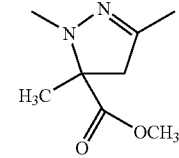 | OCH$_3$ |
| IIa-2 | (2) Cl, (4) Cl | 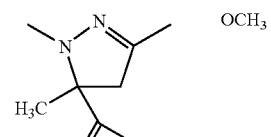 | OCH$_3$ |
| IIa-3 | (2) Cl, (4) Cl | | OC$_2$H$_5$ |
| IIa-4 | (2) Cl, (4) Cl | 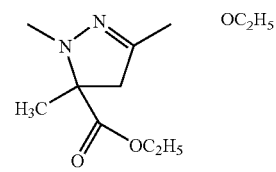 | OC$_2$H$_5$ |
| IIa-5 | (2) Cl | 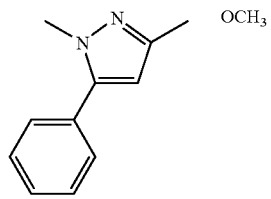 | OCH$_3$ |
| IIa-6 | (2) Cl, (4) Cl | 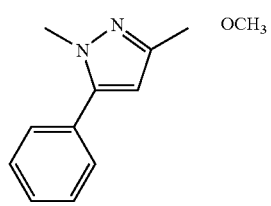 | OCH$_3$ |
| IIa-7 | (2) F | 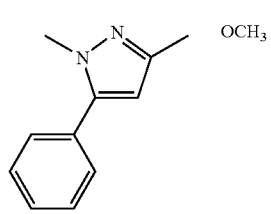 | OCH$_3$ |

TABLE 19-continued

Examples of the compounds of the formula (IIa)

(IIa)

$(X^1)_m$ — phenyl — $A^1$ — C(O) — $R^{14}$ (positions 2, 3, 4 on phenyl)

| Example No. | (Positions) $(X^1)_m$ | $A^1$ | $R^{14}$ |
|---|---|---|---|
| IIa-8 | (2) F | 1-methyl-3-methylpyrazol-5-yl with 2-Cl-phenyl | $OCH_3$ |
| IIa-9 | (2) Cl, (4) Cl | 1-methyl-5-trichloromethyl-1,2,4-triazol-3-yl | $OC_2H_5$ |
| IIa-10 | (2) Cl, (4) $CF_3$ | 1-methyl-5-phenyl-1,2,4-triazol-3-yl | $OCH_3$ |
| IIa-11 | (2) Cl | 1-methyl-3-methylpyrazol-5-yl with 2-F-phenyl | $OCH_3$ |
| IIa-12 | — | 5-phenyl-4,5-dihydroisoxazol-3-yl | $OC_2H_5$ |
| IIa-13 | (2) Cl, (4) Cl | 1,3-dimethyl-5-methylpyrazol-4-yl | $OC_2H_5$ |
| IIa-14 | (2) Cl, (4) Cl | 1-methyl-3-methyl-5-isopropylpyrazol-4-yl | $OC_2H_5$ |
| IIa-15 | (2) Cl, (4) Cl | 1-methyl-3-methyl-5-tert-butylpyrazol-4-yl | $OC_2H_5$ |
| IIa-16 | (2) Cl, (4) Cl | 5-ethyl-3-methyl-4,5-dihydroisoxazol-5-yl (via CH₂) | $OC_2H_5$ |
| IIa-17 | (2) Cl, (4) Cl | 3,5-dimethyl-4,5-dihydroisoxazol-5-yl | $OC_2H_5$ |
| IIa-18 | — | 5-methyl-5-phenyl-4,5-dihydroisoxazol-3-yl | OH |

Examples of the compounds of the formula (IIb) which are very particularly preferred as herbicide safeners according to the invention are listed in Table 20 below.

TABLE 20

Examples of the compounds of the formula (IIb)

(IIb)

Quinoline with $X^3$ at 3/4, $X^2$ at 5/6, 8-O-$A^2$-C(O)-$R^{15}$

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |

TABLE 20-continued

Examples of the compounds of the formula (IIb)

(IIb) — 8-acyloxyquinoline structure with positions 2-7, X³ at 3/4, X² at 5/6, O-A²-C(=O)-R¹⁵ at 8

| Example No. | $X^2$ (Position) | $X^3$ (Position) | $A^2$ | $R^{15}$ |
|---|---|---|---|---|
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | $OCH_2CH(OCH_3)CH_2OCH_2CH=CH_2$ (allyl glycerol ether group) |
| IIb-13 | (5) Cl | — | $CH(CH_2OCH_2CH=CH_2)$ attached via $OC(=O)CH(CH_2OCH_2CH=CH_2)$ | — |
| IIb-14 | (5) Cl | — | $CH(C_2H_5)$ via $OC(=O)CH(C_2H_5)$ | $OC_2H_5$ |
| IIb-15 | (5) Cl | — | $CH(CH_3)$ via $OC(=O)CH(CH_3)$ | $OCH_3$ |

Examples of the compounds of the formula (IIc) which are very particularly preferred as herbicide safeners according to the invention are listed in Table 21 below.

TABLE 21

Examples of the compounds of the formula (IIc)

(IIc) $R^{16}-C(=O)-N(R^{17})(R^{18})$

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 3-methyl-2,2-dimethyl-oxazolidin-3-yl |
| IIc-3 | $CHCl_2$ | 3-methyl-2,2-dimethyl-5-methyl-oxazolidin-3-yl |
| IIc-4 | $CHCl_2$ | 4-methyl-1-oxa-4-azaspiro[4.5]decan-4-yl |
| IIc-5 | $CHCl_2$ | 3-methyl-2,2-dimethyl-5-phenyl-oxazolidin-3-yl |
| IIc-6 | $CHCl_2$ | 4-methyl-3-methyl-3,4-dihydro-2H-benzo[1,4]oxazin-4-yl |
| IIc-7 | $CHCl_2$ | 3-methyl-2,2-dimethyl-5-(furan-2-yl)-oxazolidin-3-yl |

Examples of the compounds of the formula (IId) which are very particularly preferred as herbicide safeners according to the invention are listed in Table 22 below.

TABLE 22

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H |  | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H |  | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H |  | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in Table 23 below:

TABLE 23

Examples of the compounds of the formula (IIe)

(IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H |  | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H |  | (2) $OCH_3$ (5) $CH_3$ | — |
| IIe-12 | H | $CH_3$ | $CH_3$ | (2) $OCH_3$ (5) $CH_3$ | — |

Cloquintocet-mexyl, fenchlorazol-ethyl, isoxadifen-ethyl, mefenpyr-diethyl, furilazole, fenclorim, cumyluron, dymron, dimepiperate and the compounds IIe-5 and IIe-11 are most preferred as the compound which improves crop plant tolerance [component (b')], with cloquintocet-mexyl and mefenpyr-diethyl, but also isoxadifen-ethyl being especially preferred.

The compounds of the general formula (IIa) to be used according to the invention as safener are known and/or can be prepared by methods known per se (cf. WO-A-91/07874, WO-A-95/07897).

The compounds of the general formula (IIb) to be used according to the invention as safener are known and/or can be prepared by methods known per se (cf. EP-A-191736).

The compounds of the general formula (IIc) to be used according to the invention as safener are known and/or can be prepared by methods known per se (cf. DE-A-2218097, DE-A-2350547).

The compounds of the general formula (IId) to be used according to the invention as safener are known and/or can be prepared by methods known per se (cf. DE-A-19621522/U.S. Pat. No. 6,235,680).

The compounds of the general formula (IIe) to be used according to the invention as safener are known and can be prepared by methods known per se (cf. WO-A-99/66795/U.S. Pat. No. 6,251,827).

Examples of the selectively herbicidal combinations according to the invention of in each case one active compound of the formula (I) and in each case one of the above-defined safeners are listed in Table 24 below.

TABLE 24

Examples of the combinations according to the invention

| Active compounds of the formula (I) | Safener |
|---|---|
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |
| I-1-g | fenclorim |
| I-1-g | cumyluron |
| I-1-g | daimuron/dymron |
| I-1-g | dimepiperate |
| I-1-g | IIe-5 |
| I-1-g | IIe-11 |

TABLE 25

Examples of the combinations according to the invention

| Active compounds of the formula (I) | Safener |
|---|---|
| I-2-a | cloquintocet-mexyl |
| I-2-a | fenchlorazole-ethyl |
| I-2-a | isoxadifen-ethyl |
| I-2-a | mefenpyr-diethyl |
| I-2-a | furilazole |
| I-2-a | fenclorim |
| I-2-a | cumyluron |
| I-2-a | daimuron/dymron |
| I-2-a | dimepiperate |
| I-2-a | IIe-11 |
| I-2-a | IIe-5 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-11 |
| I-2-b | IIe-5 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-11 |
| I-2-d | IIe-5 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |
| I-2-f | cumyluron |

TABLE 25-continued

Examples of the combinations according to the invention

| Active compounds of the formula (I) | Safener |
|---|---|
| I-2-f | daimuron/dymron |
| I-2-f | dimepiperate |
| I-2-f | IIe-5 |
| I-2-f | IIe-11 |
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |
| I-2-g | daimuron/dymron |
| I-2-g | dimepiperate |
| I-2-g | IIe-5 |
| I-2-g | IIe-11 |

Surprisingly, it has now been found that the above-defined active compound combinations of substituted ketoenols of the general formula (I) and safeners (antidotes) from the above group (b') are not only very well tolerated by useful plants, but also have a particularly high herbicidal activity and can be used in a variety of crops, in particular in cereals (mainly wheat), but also in soybeans, potatoes, maize and rice, for the selective control of weeds.

It must be considered as surprising that, from a multiplicity of known safeners or antidotes which are capable of antagonizing the damaging effect of a herbicide on the crop plants, it is precisely the abovementioned compounds of group (b') which are capable of virtually completely compensating for the harmful effect of substituted cyclic ketoenols on the crop plants without adversely affecting the herbicidal activity towards the weeds to a substantial degree.

What must be emphasized in this context is the particularly advantageous activity of the particularly and most preferred combination partners from group (b'), in particular with regard to leaving cereal plants, such as, for example, wheat, barley and rye, but also maize and rice, as crop plants, unharmed.

Using, for example, according to process (A) ethyl N-[(4-chloro-2,6-dimethyl)-phenylacetyl]-1-amino-3-methoxycyclohexanecarboxylate as starting material, the course of the process according to the invention can be represented by the reaction scheme below:

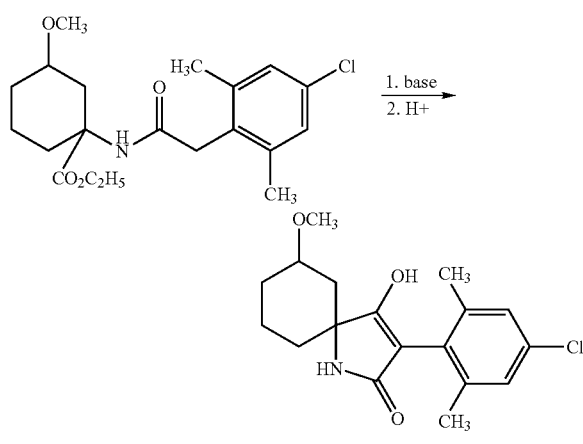

Using, for example, according to process (B) ethyl O-[(2-chloro-6-methyl)phenylacetyl]-1-hydroxy-3-ethoxycyclohexanecarboxylate, the course of the process according to the invention can be represented by the reaction scheme below:

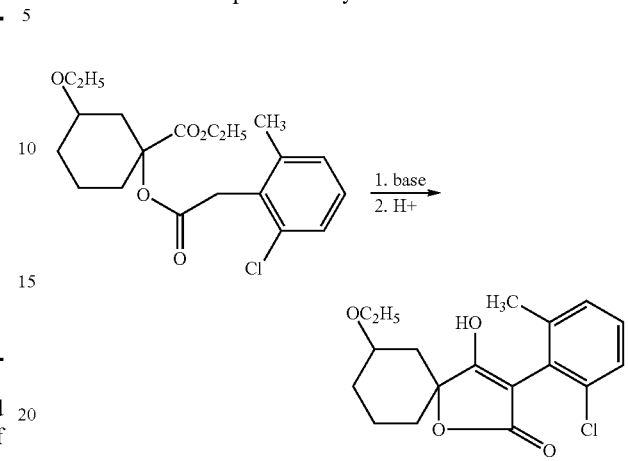

Using, for example, according to process (Cα) 7-butoxy-3-[(4-chloro-2,6-dimethyl)-phenyl]-1-azaspiro[4,5]decane-2,4-dione and pivaloyl chloride as starting materials, the course of the process according to the invention can be represented by the reaction scheme below:

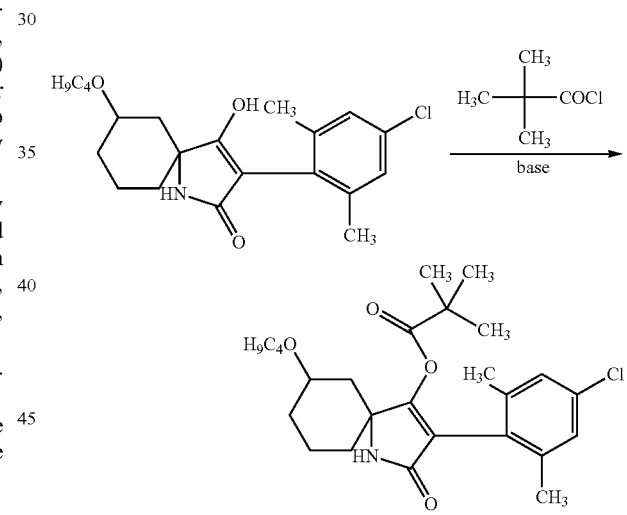

Using, for example, according to process (C) (variant β) 7-ethoxy-3-[(2,4-dichloro)-phenyl]-1-oxaspiro[4,5]decane-2,4-dione and acetic anhydride as starting materials, the course of the process according to the invention can be represented by the reaction scheme below:

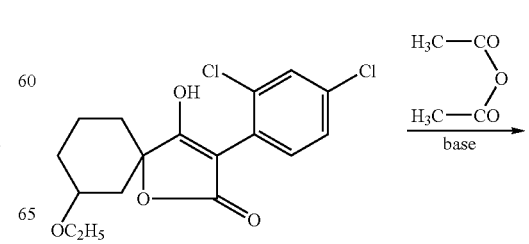

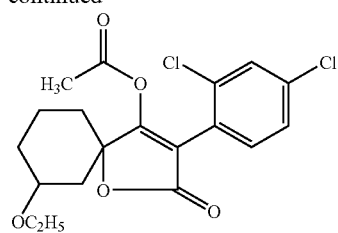

Using, for example, according to process (D) 7-methoxy-3-[(2,4-dichloro-6-methyl)-phenyl]-1-azaspiro[4,5]decane-2,4-dione and ethyl chloroformate as starting materials, the course of the process according to the invention can be represented by the reaction scheme below:

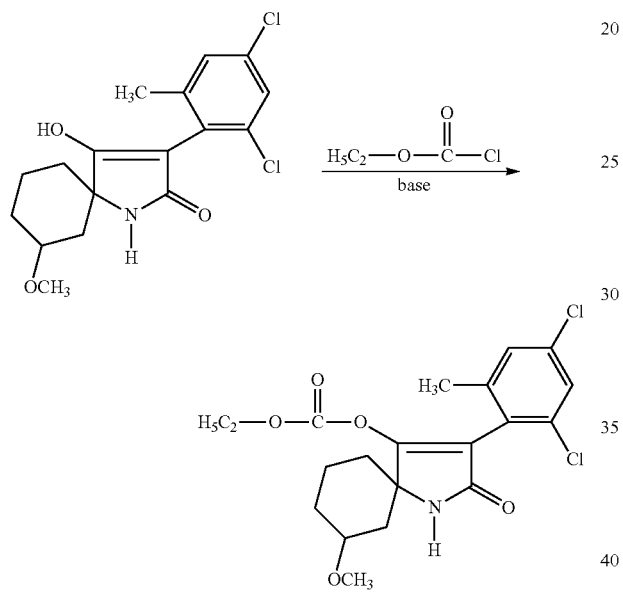

Using, for example, according to process (E) 7-ethoxy-3-[(2,4,6-trimethyl)phenyl]-1-oxaspiro[4,5]decane-2,4-dione and methyl chloromonothioformate as starting materials, the course of the reaction can be represented as follows:

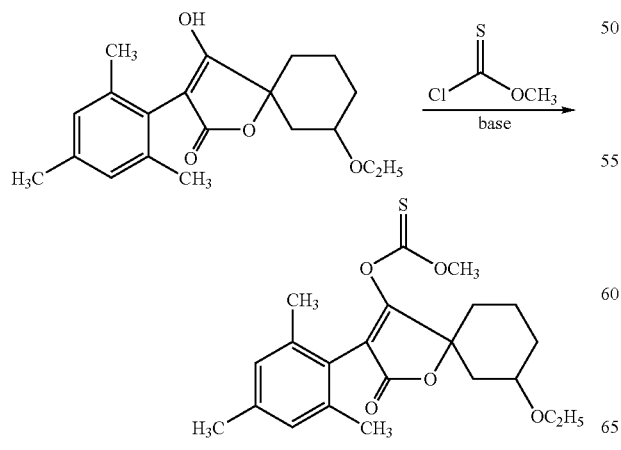

Using, for example, according to process (F) 7-butoxy-3-[(2,4,6-trimethyl)phenyl]-1-azaspiro[4,5]decane-2,4-dione and methanesulphonyl chloride as starting materials, the course of the reaction can be represented by the reaction scheme below:

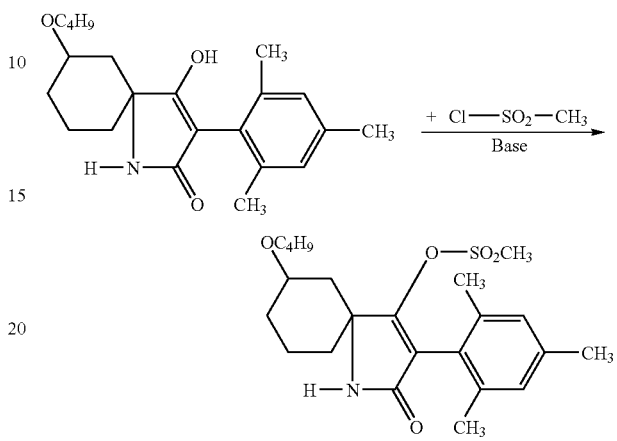

Using, for example, according to process (G) 7-methoxy-3-[(2,4-dichloro-6-methyl)-phenyl]-1-oxaspiro[4,5]decane-2,4-dione and 2,2,2-trifluoroethyl methanethiophosphonyl chloride as starting materials, the course of the reaction can be represented by the reaction scheme below:

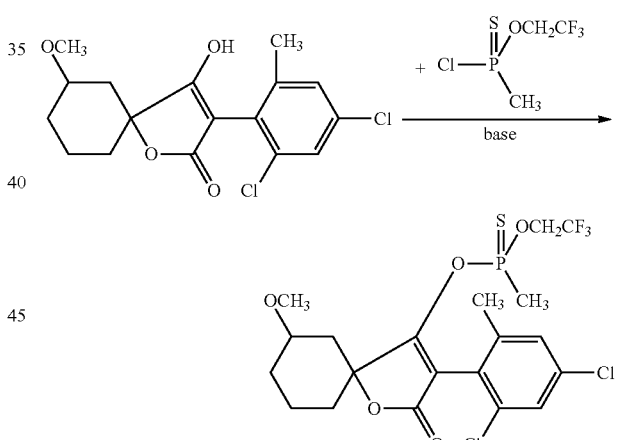

Using, for example, according to process (H) 7-methoxy-3-[(2,3,4,6-tetramethyl)-phenyl]-1-azaspiro[4,5]decane-2,4-dione and NaOH as components, the course of the process according to the invention can be represented by the reaction scheme below:

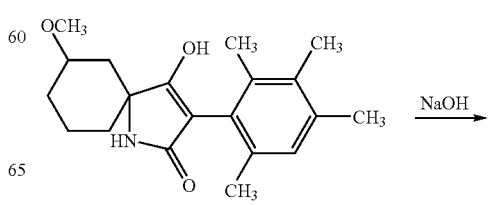

-continued

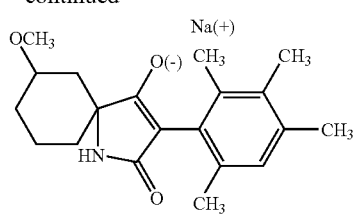

Using, for example, according to process (I) (variant α) 7-ethoxy-3-[(2,4,5-trimethyl)phenyl]-1-oxaspiro[4,5]decane-2,4-dione and ethyl isocyanate as starting materials, the course of the reaction can be represented by the reaction scheme below:

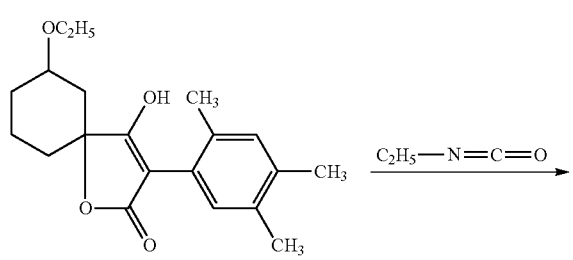

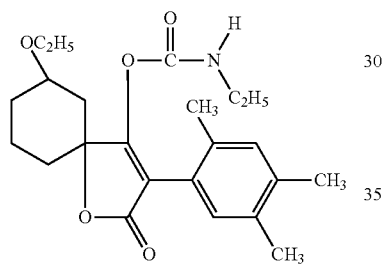

Using, for example, according to process (I) (variant β) 7-butoxy-3-[(2,4,6-trimethyl)phenyl]-1-azaspiro[4,5]decane-2,4-dione and dimethylcarbamoyl chloride as starting materials, the course of the reaction can be represented by the scheme below:

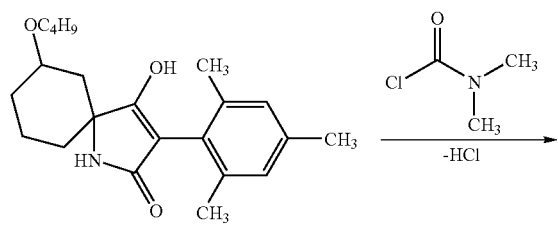

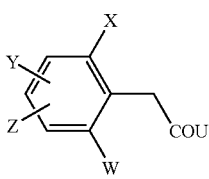

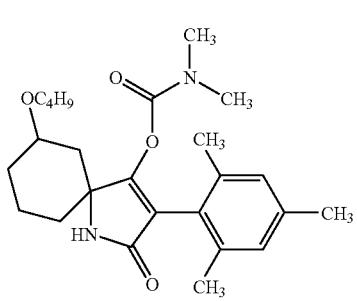

The compounds, required as starting materials in the process (A) according to the invention, of the formula (II)

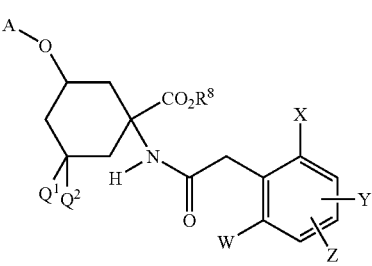
(II)

in which

A, B, $Q^1$, $Q^2$, W, X, Y, Z and $R^8$ are as defined above are novel.

The acylamino acid esters of the formula (II) are obtained, for example, when amino acid derivatives of the formula (XIV)

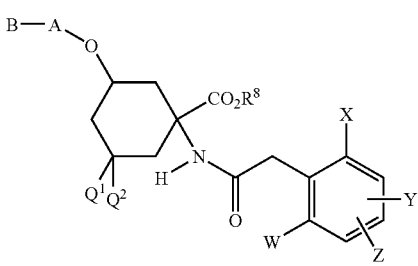
(XIV)

in which

A, B, $Q^1$ and $Q^2$ and $R^1$ are as defined above, are acylated with substituted phenylacetic acid derivatives of the formula (XV)

(XV)

in which

W, X, Y and Z are as defined above and

U represents a leaving group introduced by reagents that activate carboxylic acids, such as carbonyldiimidazole, carbonyldiimides (such as, for example, dicyclohexylcarbonyldiimide), phosphorylating reagents (such as, for example POCl$_3$, BOP—Cl), halogenating agents, for example thionyl chloride, oxalyl chloride, phosgene or chloroformic esters, (Chem. Reviews 52, 237-416 (1953); Bhattacharya, Indian J. Chem. 6 341-5, 1968) or when acylamino acids of the formula (XVI)

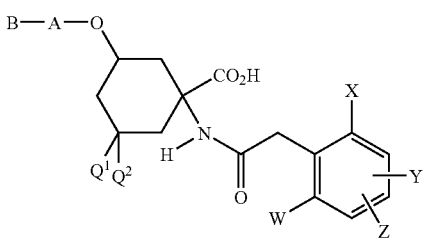

(XVI)

in which
A, B, $Q^1$, $Q^2$, W, X, Y and Z are as defined above
are esterified (Chem. Ind. (London) 1568 (1968)).
The compounds of the formula (XVI)

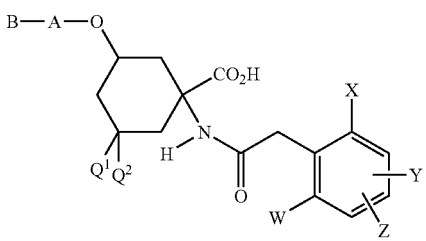

(XVI)

in which
A, B, $Q^1$, $Q^2$, W, X, Y and Z are as defined above,
are novel.

The compounds of the formula (XVI) are obtained, for example, when 1-amino-cyclohexanecarboxylic acids of the formula (XVII)

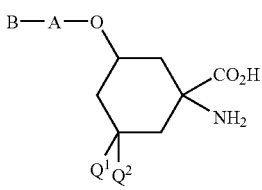

(XVII)

in which
A, B, $Q^1$ and $Q^2$ are as defined above
are acylated according to Schotten-Baumann (Organikum, VEB Deutscher Verlag der Wissenschaften, Berlin 1977, p. 505) with substituted phenylacetic acid derivatives of the formula (XV)

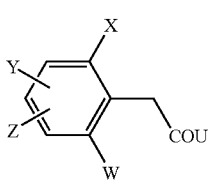

(XV)

in which
U, W, X, Y and Z are as defined above.

Some of the compounds of the formula (XV) are known, and/or they can be prepared by the known processes from the laid-open publications cited at the outset.

The compounds of the formulae (XIV) and (XVII) are novel and can be prepared by known processes (see, for example, Compagnon, Ann. Chim. (Paris) [14] 5, pp. 11-22, 23-27 (1970), L. Munday, J. Chem. Soc. 4372 (1961); J. T. Eward, C. Jitrangeri Can. J. Chem. 53, 3339 (1975)).

The novel 1-aminocyclohexanecarboxylic acids (XVII) are generally obtainable by means of a Bucherer-Bergs synthesis or a Strecker synthesis, where they are obtained in each case in different isomeric forms. Hereinbelow, for the sake of simplicity, the isomers in which the 3-substituent (O-A-B) and the amino group are equatorial/axial or axial/equatorial are referred to as β. Hereinbelow, for the sake of simplicity, the isomers in which the amino group and the 3-substituent (O-A-B) are equatorial/equatorial or axial/axial are referred to as α.

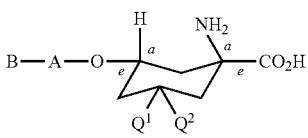

Example: β-isomer

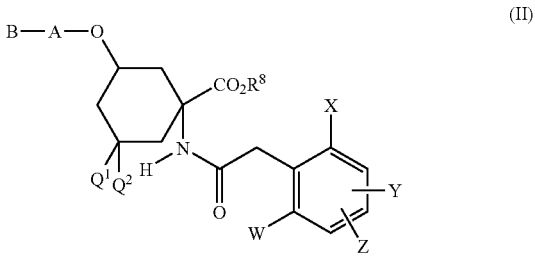

Example: α-isomer (L. Munday, J. Chem. Soc. 4372 (1961).

Furthermore, the starting materials, used in process (A) above, of the formula (II)

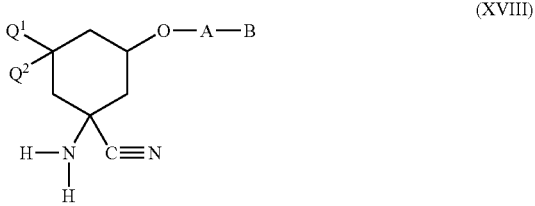

(II)

in which
A, B, $Q^1$, $Q^2$, W, X, Y, Z and $R^1$ are as defined above can be prepared by reacting 1-aminocyclohexanecarbonitriles of the formula (XVIII)

(XVIII)

in which
A, B, $Q^1$ and $Q^2$ are as defined above,
with substituted phenylacetic acid derivatives of the formula (XV)

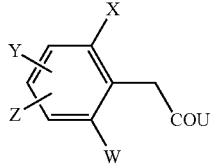
(XV)

in which
U, W, X, Y and Z are as defined above,
to give compounds of the formula (XIX)

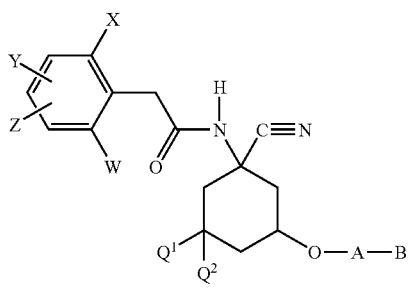
(XIX)

in which
A, B, $Q^1$, W, X, Y and Z are as defined above,
which are then subjected to acid alcoholysis.

The compounds of the formula (XIX) are likewise novel. The compounds of the formula (XVIII) are likewise novel and can be prepared, for example, as described in EP 595 130.

The compounds, required as starting materials for the process (B) according to the invention, of the formula (III)

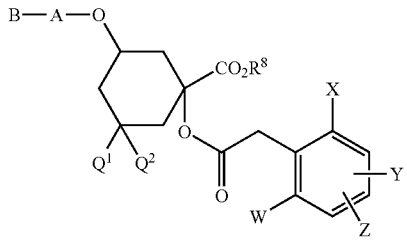
(III)

in which
A, B, $Q^1$, $Q^2$, W, X, Y, Z and $R^8$ are as defined above,
are novel.

They can be prepared by methods known in principle.

The compounds of the formula (III) are obtained, for example, when
1-hydroxycyclohexanecarboxylic esters of the formula (XX)

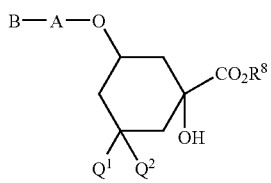
(XX)

in which
A, B, $Q^1$, $Q^2$ and $R^1$ are as defined above,
are acylated with substituted phenyl acetic acid derivatives of the formula (XV)

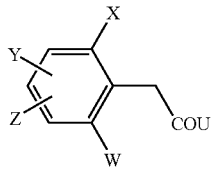
(XV)

in which
U, W, X, Y and Z are as defined above
(Chem. Reviews 52, 237-416 (1953)).

The 1-hydroxy-3-alkoxycyclohexanecarboxylic esters of the formula (XX) are novel. They are obtained, for example, when substituted 1-hydroxy-3-alkoxycyclohexane-carbonitriles are reacted with alcohols in the presence of acids, for example according to Pinner. The cyanohydrin is obtained, for example, by reacting substituted 3-alkoxycyclohexan-1-ones with hydrocyanic acid.

The acid halides of the formula (IV), carboxylic anhydrides of the formula (V), chloroformic esters or chloroformic thioesters of the formula (VI), chloromonothioformic esters or chlorodithioformic esters of the formula (VII), sulphonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) furthermore required as starting materials for carrying out the processes (C), (D), (E), (F), (G), (H) and (I) according to the invention are generally known compounds of organic or inorganic chemistry.

In addition, the compounds of the formula (XV) are known from the patent applications cited at the outset, and/or they can be prepared by the methods given therein.

The process (A) is characterized in that compounds of the formula (II) in which A, B, $Q^1$, $Q^2$, W, X, Y, Z and $R^8$ are as defined above are, in the presence of a diluent and in the presence of a base, subjected to an intramolecular condensation.

Suitable diluents for the process (A) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperature can be varied within a relatively large range. In general, the process is carried out at temperatures between −75° C. and 200° C., preferably between −50° C. and 150° C.

The process (A) according to the invention is generally carried out under atmospheric pressure.

When carrying out the process (A) according to the invention, the reaction components of the formula (II) and the deprotonating bases are generally employed in equimolar to approximately doubly equimolar amounts. However, it is also possible to use a relatively large excess (up to 3 mol) of one component or the other.

The process (B) is characterized in that compounds of the formula (III) in which A, B, $Q^1$, $Q^2$, W, X Y, Z and $R^8$ are as defined above are, in the presence of a diluent and in the presence of a base, subjected to an intramolecular condensation.

Suitable diluents for the process (B) according to the invention are all organic solvents which are inert towards the reaction participant. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl-($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperature can be varied within a relatively wide range. In general, the process is carried out at temperatures between −75° C. and 200° C., preferably between −50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for the process ($C_\alpha$) according to the invention are all solvents which are inert towards the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl formamide, dimethyl sulphoxide and sulpholane. The hydrolytic stability of the acid halide permitting, the reaction can also be carried out in the presence of water.

Suitable acid binders for the reaction according to the process ($C_\alpha$) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

In the process ($C_\alpha$) according to the invention, the reaction temperature can be varied within a relatively wide range. In general, the process is carried out at temperatures between −20° C. and +150° C., preferably between 0° C. and 100° C.

When carrying out the process ($C_\alpha$) according to the invention, the starting materials of the formulae (I-1-a) to (I-2-a) and the carbonyl halide of the formula (IV) are generally each employed in approximately equivalent amounts. However, it is also possible to use a relatively large excess (up to 5 mol) of the carbonyl halide. Work-up is carried out by customary methods.

The process ($C_\beta$) is characterized in that compounds of the formulae (I-1-a) to (I-2-a) are reacted in each case with carboxylic anhydrides of the formula (V), if appropriate in the presence of a diluent and if appropriate in the presence of an acid binder.

Suitable diluents for the process ($C_\beta$) according to the invention are, preferably, those diluents which are also preferred when using acid halides. Besides, it may also be possible for excess carboxylic anhydride to act simultaneously as diluent.

In process ($C_\beta$), suitable acid binders, which are added, if appropriate, are preferably those acid binders which are also preferred when using acid halides.

The reaction temperature in the process ($C_\beta$) according to the invention can be varied within a relatively wide range. In general, the process is carried out at temperatures between −20° C. and +150° C., preferably between 0° C. and 100° C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable acid binders for the process (D) according to the invention are all customary acid acceptors. Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (D) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethyl formamide, dimethyl sulphoxide and sulpholane.

When carrying out the process (D) according to the invention, the reaction temperature can be varied within a relatively wide range. The reaction temperature is generally between −20° C. and +100° C., preferably between 0° C. and 50° C.

The process (D) according to the invention is generally carried out under atmospheric pressure.

When carrying out the process (D) according to the invention, the starting materials of the formulae (I-1-a) to (I-2-a) and the appropriate chloroformic ester or chloroformic thioester of the formula (VI) are generally each employed in approximately equivalent amounts. However, it is also possible to use a relatively large excess (up to 2 mol) of one component or-the other. Work-up is carried out by customary methods. In general, precipitated salts are removed and the reaction mixture that remains is concentrated by removing the diluent under reduced pressure.

The process (E) according to the invention is characterized in that compounds of the formulae (I-1-a) to (I-2-a) are in each case reacted with compounds of the formula (VII), in the presence of a diluent and, if appropriate, in the presence of an acid binder.

In the Preparation Process (E), about 1 mol of chloromonothioformic ester or chlorodithioformic ester of the formula (VII) is reacted per mole of starting material of the formulae (I-1-a) to (I-2-a), at from 0 to 120° C., preferably from 20 to 60° C.

Suitable diluents, which are added, if appropriate, are all inert polar organic solvents, such as ethers, amides, sulphones, sulphoxides, and also halogenated alkanes.

Preference is given to using dimethyl sulphoxide, tetrahydrofuran, dimethyl-formamide, ethyl acetate or methylene chloride.

If, in a preferred embodiment, the enolate salt of the compounds (I-1-a) to (I-2-a) is prepared by the addition of strong deprotonating agents, such as, for example, sodium hydride or potassium tert-butoxide, the further addition of acid binders can be dispensed with.

Suitable bases for the process (E) are all customary proton acceptors. Preference is given to using alkali metal hydrides, alkali metal alkoxides, alkali metal or alkaline earth metal carbonates or bicarbonates or nitrogen bases. Examples which may be mentioned are sodium hydride, sodium methoxide, sodium hydroxide, calcium hydroxide, potassium carbonate, sodium bicarbonate, triethyamine, dibenzylamine, diisopropylethylamine, pyridine, quinoline, diazabicyclooctance (DABCO), diabicyclononene (DBN) and diazabicycloundecene (DBU).

The reaction can be carried out under atmospheric pressure or under elevated pressure and is preferably carried out under atmospheric pressure. Work-up is carried out by customary methods.

The process (F) according to the invention is characterized in that compounds of the formulae (I-1-a) to (I-2-a) are in each case reacted with sulphonyl chlorides of the formula (VIII), if appropriate in the presence of a diluent and if appropriate in the presence of an acid binder.

In the Preparation Process (F), about 1 mol of sulphonyl chloride of the formula (VIII) is reacted per mole of starting material of the formula (I-1-a) to (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulphones, sulphoxides or halogenated hydrocarbons, such as methylene chloride.

Preference is given to using dimethyl sulphoxide, tetrahydrofuran, dimethyl-formamide, ethyl acetate, methylene chloride.

If, in a preferred embodiment, the enolate salt of the compounds (I-1-a) to (I-2-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, pyridine and triethylamine.

The reaction can be carried out under atmospheric pressure or under elevated pressure and is preferably carried out under atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In the Preparation Process (G), to obtain compounds of the formulae (I-1-e) to (I-2-e), 1 to 2, preferably 1 to 1.3 mol of the phosphorus compound of the formula (IX) are reacted to 1 mol of the compounds (I-1-a) to (I-2-a), at temperatures between −40° C. and 150° C., preferably between −10 and 110° C.

The process (G) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide, methylene chloride.

Suitable acid binders, which are added, if appropriate, are customary inorganic or organic bases, such as hydroxides, carbonates or amines. Examples are sodium hydroxide, sodium carbonate, potassium carbonate, pyridine and triethylamine.

The reaction can be carried out under atmospheric pressure or under elevated pressure and is preferably carried out under atmospheric pressure. Work-up is carried out by customary methods of organic chemistry. The end products are preferably purified by crystallization, chromatographic purification or by "incipient distillation", i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a diluent.

Suitable diluents for the process (H) according to the invention are, preferably, ethers, such as tetrahydrofuran, dioxane, diethyl ether, or else alcohols, such as methanol, ethanol, isopropanol, and also water. The process (H) according to the invention is generally carried out under atmospheric pressure. The reaction temperature is generally between −20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or with (Iβ) compounds of the formula (XIII), if appropriate in the presence of a diluent and if appropriate in the presence of an acid binder.

In Preparation Process (Iα), about 1 mol of isocyanate of the formula (XII) is reacted per mole of starting material of the formulae (I-1-a) to (I-2-a), at from 0 to 100° C., preferably at from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to accelerate the reaction. Suitable catalysts are, very advantageously, organotin compounds, such as, for example, dibutyltin dilaurate.

The reaction is preferably carried out under atmospheric pressure.

In the Preparation Process (Iβ), about 1 mol of carbamoyl chloride of the formula (XIII) is reacted per mole of starting material of the formulae (I-1-a) to (I-2-a), at from 0 to 150° C., preferably from 20 to 70° C.

Suitable diluents, which are added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethyl-formamide or methylene chloride.

If, in a preferred embodiment, the enolate salt of the compound (I-1-a) to (I-2-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The active compounds are well tolerated by plants and have advantageous toxicity to warm-blooded species; they can be employed for controlling animal pests, in particular insects, arachnids and nematodes encountered in agriculture, forests, in the protection of stored products and materials and in the hygiene sector. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus* corporis, *Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi Eriosoma lanigerum, Hyalopterus arundinis, Phylloxera vastatrix, Pemphigus* spp., *Macrosiphum avenae, Myzus* spp., *Phorodon humul Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia* ni *Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha*

*melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds or active compound combinations according to the invention may also be used in certain concentrations or application rates to act as herbicides. If appropriate, the compounds can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds and also roots, tubers and rhizomes. The plant parts also include harvested material and vegetative and generative propagation material, for example cuttings, tubers, rhizomes, offsets and seeds.

The treatment according to the invention of the plants and plant parts with the active compounds or active compound combinations is carried out directly or by allowing the compounds to act on the surroundings, environment or storage space by the customary treatment methods, for example by immersion, spraying, injecting, evaporation, fogging, scattering, painting on and, in the case of propagation material, in particular in the case of seeds, also by applying one or more coats.

The active compounds or active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as components in the mixtures are, for example, the following:
Fungicides:
2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris (albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsutfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrin; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]-ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decan-3-amine; sodium tetrathiocarbonate;
and copper salts and preparations such as Bordeaux mixture; copper hydroxide; copper naphthenate; copper oxychloride; copper sulphate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin S-cyclopentyl isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, cloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusate-sodium, dofenapyn, DOWCO-439, eflusilanate, emamectin, emamectin benzoate, empenthrin (1R isomer), endosulfan, *Entomophthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin,
japonilure,
kadethrin, nuclear polyhedrosis viruses, kinoprene, lambda-cyhalothrin, lindane, lufenuron,
malathion, mecarbam, mesulfenfos, metaldehyde, metam-sodium, methacrifos, methamidophos, Metarhizium anisopliae, Metarhizium flavoviride, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800,
naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron,
OK-5101, OK-5201, OK-9601, OK-9602, OK-9701, OK-9802, omethoate, oxamyl, oxydemeton-methyl,
*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen,
quinalphos,
resmethrin, RH-5849, ribavirin, RU-12457, RU-15525,
S-421, S-1833, salithion, sebufos, SI-0009, silafluofen, spinosad, spirodiclofen, spiromesifen, sulfluramid, sulfotep, sulprofos, SZI-121,
tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R isomer), tetrasul, theta-cypermethrin, thiacloprid, thiamethoxam, thiapronil, thiatriphos, thiocyclam hydrogen oxalate, thiodicarb, thiofanox; thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma atroviride*, triflumuron, trimethacarb,
vamidothion, vaniliprole, verbutin, *Verticillium lecanii*, WL-108477, WL-40027,
YI-5201, YI-5301, YI-5302,
XMC, xylylcarb,
ZA-3274, zeta-cypermethrin, zolaprofos, ZXI-8901,
the compound 3-methylphenyl propylcarbamate (Tsumacide Z),
the compound 3-5-chloro-3-pyridinyl)-8-(2,2,2-trifluoroethyl)-8-azabicyclo-[3.2.1]octane-3-carbonitrile (CAS Reg. No. 185982-80-3) and the corresponding 3-endo isomer (CAS Reg. No. 185984-60-5) (cf WO 96/37494, WO 98/25923),
and preparations which contain insecticidally active plant extracts, nematodes, fungi or viruses.

A mixture with other known active compounds, such as herbicides, or with fertilizers and growth regulators is also possible.

When used as insecticides in their commercially available formulations and in the use forms prepared with these formulations, the active compounds according to the invention can furthermore exist in the form of a mixture with synergists. Synergists are compounds by which the activity of the active compounds is increased without it being necessary for the synergist added to be active itself The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound or active compound combinations is/are distinguished by excellent residual action on wood and clay as well as good stability to alkali on limed substrates.

As already mentioned above, it is possible to treat all plants and their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, accelerated maturation, facilitated harvesting, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such traits are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, which must be mentioned especially, are better defence of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, oilseed rape, beet, sugar cane and fruit plants (with the fruits apples, pears, citrus fruits and grapes), with particular emphasis on maize, soybeans, potatoes, cotton and oilseed rape. Traits which are especially emphasized are the increased defence of the plants against insects, owing to toxins being formed in the plants, in particular toxins which are generated in the plants by the genetic material of Bacillus thuringiensis (for example by the genes CryIA(a), CryIA(b), CryIA(c), CryIIA, CryIIIA, CryIIIB2, Cry9c, Cry2Ab, Cry3Bb and CryIF and their combinations; hereinbelow "Bt plants"). Other traits which are particularly emphasized are the increased defence of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include also the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously with the compounds according to the invention or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds or active compound combinations according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damatina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the sub-class of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds or active compound combinations according to the invention are also suitable for controlling arthropods which attack agricultural livestock, such as, for example, cattle, sheep, goats, horses, pigs, donkeys, camels, buffaloes, rabbits, chickens, turkeys, ducks, geese, honey-bees, other domestic animals, such as, for example, dogs, cats, caged birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds or active compound combinations according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds or active compound combinations can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds or active compound combinations according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials, such as, preferably, synthetic materials, glues, sizes, papers and boards, leather, wood and timber products, and paint. The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds or active compound combinations can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries. The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl)adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid and triflumuron, and fungicides, such as epoxyconazole, hexaconazole, azaconazole, propiconazole, tebuconazole, cyproconazole, metconazole, imazalil, dichlofluanid, tolylfluanid, 3-iodo-2-propynylbutyl carbamate, N-octyl-isothiazolin-3-one and 4,5-dichloro-N-octylisothiazolin-3-one.

The compounds or active compound combinations according to the invention can at the same time be employed for protecting objects which come into contact with salt water or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin)sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithio-carbamoylzinc ethylene-bisthiocarbamate, zinc oxide, copper(I) ethylene-bisdithio-carbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridinetriphenylborane, tetrabutyldistannoxane, 2,3,5,6-tetrachloro-4-(methylsulphonyl) pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds or active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries.

They are active against sensitive and resistant species and against all development stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The active compounds or active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds or active compound combinations according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsiurn, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicurn, Paspalum, Phalaris, Phleum, Poa, Rottboellia, Sagittaria, Scirpus, Setaria, Sorghum.*

Monocotyledonous crods of the genera: *Allium, Ananas, Asparagus, Avena, Hordeum, Oryza, Panicum, Saccharum, Secale, Sorghum, Triticale, Triticum, Zea.*

However, the use of the active compounds or active compound combinations according to the invention is in no way restricted to these genera, but extends in the same manner to other plants.

Depending on the concentration, the active compounds or active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantations and hop fields, on lawns, turf and pastureland, and for the selective control of weeds in annual crops.

The compounds or active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds or active compound combinations according to the invention can also be employed for controlling animal pests and fungal or bacterial plant diseases. If appropriate, they can also be used as intermediates or precursors for the synthesis of other active compounds.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latex, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with weed control products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benzcarbazone, benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), diferzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, KIH 485, lactofen, lenacil, linuron, MCPA, mecoprop, mefenacet, mesosulfurone, mesotrione, metanufop metamitron, metazachlor, methabenzthiazuron, metobenzuron, metobromuron, (alpha-) metolachlor, metosulam, metoxuron, metribuzin, metsulfuron (-methyl), molinate, monolnuron, naproanilide, napropamide, neburon, nicosulfuron, norflurazon, orbencarb, orthosulfamuron oryzalin, oxadiargyl, oxadiazon, oxasulfuron, oxaziclomefone, oxyfluorfen, paraquat, pelargonic acid, pendimethalin, pendralin, penoxsulam pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), pyrimisulfan, quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, topramezone thidiazimin, thifensulfuron (-methyl), thiobencarb, tiocarbazil, topramezone tralkoxydim, triallate, triasulfuron, tribenuron, tribenuron (-methyl), triclopyr, tridiphane, trifluralin, trifloxysulfuron, triflusulfuron (-methyl), tritosulfuron and

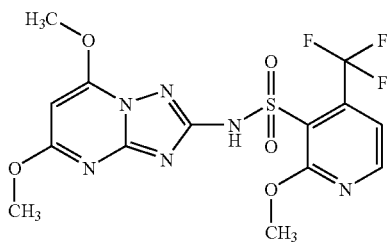 [SMILES: COc1cc(OC)n2nc(NS(=O)(=O)c3c(C(F)(F)F)ccnc3OC)nc2n1]

A mixture with other known active compounds, such as fungicides, insecticides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to sowing.

The application rate of active compound can vary within a relatively large range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound. combinations can be varied within relatively wide ranges. In general, from 0.001 to 1000 parts by weight, preferably from 0.01 to 100 parts by weight, particularly preferably from 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additive in the formulations, mineral or vegetable oils which are tolerated by plants (for example commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley rice), maize, soybeans, potatoes, cotton, oil seed rape, beet, sugar cane and also fruit plants (with the fruits apples, pears, citrus fruits and grapevines), greater emphasis being given to cereals, maize, soybeans, potatoes, cotton and oil seed rape.

Fungicides can be employed in crop protection for controlling *Plasmodiophoromycetes, Oomycetes, Chytridiomycetes, Zygomycetes, Ascomycetes, Basidiomycetes* and *Deuteromycetes*.

Bactericides can be employed in crop protection for controlling *Pseudomonadaceae, Rhizobiaceae, Enterobacteriaceae, Corynebacteriaceae* and *Streptomycetaceae*.

Some pathogens causing fungal and bacterial diseases which come under the generic names listed above may be mentioned as examples, but not by way of limitation:

*Xanthomonas* species, such as, for example, *Xanthomonas campestris* pv. oryzae;

*Pseudomonas* species, such as, for example, *Pseudomonas syringae* pv. lachrymans;

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance against these microorganisms.

In the present case, undesirable microorganisms are to be understood as meaning phytopathogenic fungi bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, papers and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (*Basidiomycetes*), and against slime organisms and algae.

Microorganisms of the following genera may be mentioned as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*, and

*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latex, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of Suitable Mixing Components are the Following:
Fungicides:
2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamide; carvone; quinomethionate; chlobenthiazone; chlorfenazole; chloroneb; chlorothalonil; chlozolinate; clozylacon; cyazofamide; cyflufenamide; cymoxanil; cyproconazole; cyprodinil; cyprofuram; dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamide; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-aluminium; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris-albesil; iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phtha-lide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]-ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazol-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decan-3-amine; sodium tetrathiocarbonate; and copper salts and copper preparations, such as Bordeaux mixture; copper hydroxide; copper naphthenate; copper oxychloride; copper sulphate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin IR isomer, alpha-cypermethrin(alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin S-cyclopentyl isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusate-sodium, dofenapyn, DOWCO-439, eflusilanate, emamectin, emamectin benzoate, empenthrin (1R isomer), endosulfan, *Entomophthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethirin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metarhizium anisopliae, Metarhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MFI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma atroviride*, triflumuron, trimethacarb, varmidothion, vaniliprole, verbutin, *Verticillium lecanii*, VVL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (*Tsumacide Z*), the compound 3-5-chloro-3-pyridinyl)-8-2,2,2-trifluoroethyl)-8-azabicyclo-[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means limits the mycotic spectrum covered, but is only for illustration The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The preparation and the use of the active compounds according to the invention is illustrated by the examples below.

EXAMPLES

Example I-1-a-1

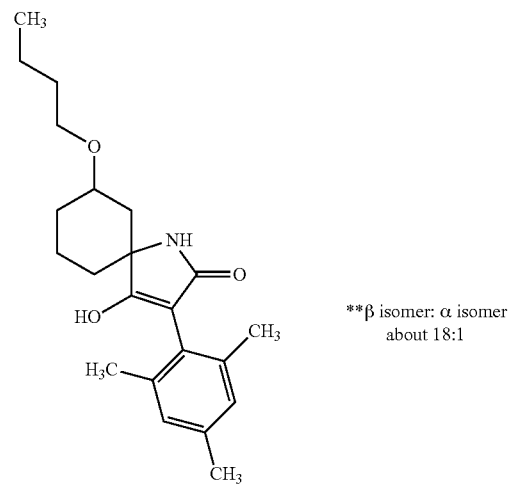 [SMILES: CCCCOC1CCCC2(C1)NC(=O)C(c1c(C)cc(C)cc1C)=C2O]

**β isomer: α isomer about 18:1

In a 100 ml three-necked flask fitted with thermometer and reflux condenser, under argon, 2.2 eq.=1.33 g of potassium tert-butoxide 95% pure (11.3 mmol) are initially charged in 5 ml dimethylacetamide. At 80° C., 2 g of the compound of Example II-1 (5.13 mmol) in 5 ml of dimethylacetamide are added dropwise. The mixture is stirred at 80° C. for 1 hour.

The reaction mixture is stirred into 100 ml of ice-water and adjusted to pH 2 using concentrated HCl, and the precipitate is filtered off with suction.

The product is purified by column chromatography on silica gel (dichloromethane:ethyl acetate 5:3).

Yield: 1.8 g (94% of theory) 72° C.

**Enriched isomer after purification by column chromatography on silica gel

Analogously to Example (I-1-a-1) and in accordance with the general statements on the preparation, the following compounds of the formula (I-1-a) are obtained

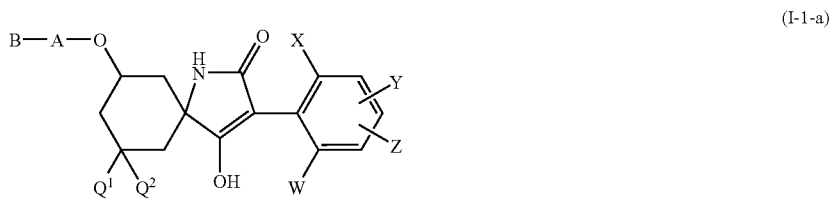

(I-1-a)

| Ex. No. | W | X | Y | Z | A | B | $Q^1$ | $Q^2$ | m.p. ° C. | Isomer |
|---|---|---|---|---|---|---|---|---|---|---|
| I-1-a-2 | $CH_3$ | $CH_3$ | 4-$CH_3$ | H | $CH_2$ | H | H | H | Oil *3.4-3.48, 3.69-3.7 (m, 1H, O—CH) 6.83, (s, 2H, ArH) | α:β 1:1 |
| I-1-a-3 | $CH_3$ | $CH_3$ | 4-$CH_3$ | H | $CH_2$ | H | $CH_3$ | $CH_3$ | Oil *0.97, 1.07 (2s, 6H, $C(CH_3)_2$) | α** |
| I-1-a-4 | $CH_3$ | $CH_3$ | 4-$CH_3$ | H | $CH_2$ | i-$C_3H_7$ | $CH_3$ | $CH_3$ | Wax *3.20 (dd, 2H, $OCH_2$) 6.84 (s, 2-H, ArH) | α** |
| I-1-a-5 | H | $CH_3$ | 5-(4-Cl-Ph) | H | $CH_2$ | $C_3H_7$ | H | H | 139 | α** |
| I-1-a-6 | H | $CH_3$ | 5-(4-Cl-Ph) | H | $CH_2$ | $C_3H_7$ | H | H | 155 | β** |
| I-1-a-7 | Br | $C_2H_5$ | 4-$CH_3$ | H | $CH_2$ | $CH_3$ | H | H | 258 | α** |
| I-1-a-8 | Cl | $C_2H_5$ | 4-Br | H | $CH_2$ | $C_3H_7$ | H | H | 110 | β** |
| I-1-a-9 | Cl | $C_2H_5$ | 4-Br | H | $CH_2$ | $C_3H_7$ | H | H | 128 | α** |
| I-1-a-10 | Br | $C_2H_5$ | 4-$CH_3$ | H | $CH_2$ | $C_2H_5$ | H | H | 235 | α** |
| I-1-a-11 | Br | $C_2H_5$ | 4-$CH_3$ | H | $CH_2$ | $C_3H_7$ | H | H | 228 | α** |
| I-1-a-12 | Br | $C_2H_5$ | 4-$CH_3$ | H | $CH_2$ | $C_2H_5$ | H | H | 174 | β** |
| I-1-a-13 | H | $CH_3$ | H | 5-$CH_3$ | $CH_2$ | $CH_3$ | H | H | 208 | α** |
| I-1-a-14 | Br | $C_2H_5$ | 4-$CH_3$ | H | $CH_2$ | H | H | H | 200 | β** |
| I-1-a-15 | H | $CH_3$ | H | 5-$CH_3$ | $CH_2$ | $CH_3$ | H | H | Oil *2.09, 2.25 (2s, 6H, Ar—$CH_3$) 3.46 (q, 2H, O—$\underline{CH_2}$—$CH_3$) | β** |
| I-1-a-16 | Br | $C_2H_5$ | 4-$CH_3$ | H | $CH_2$ | H | H | H | 228 | α** |
| I-1-a-17 | Br | $C_2H_5$ | 4-$CH_3$ | H | $CH_2$ | $C_3H_7$ | H | H | 228 | β** |
| I-1-a-18 | Br | $C_2H_5$ | 4-$CH_3$ | H | $CH_2$ | $CH_3$ | H | H | 194 | β** |
| I-1-a-19 | $CH_3$ | $CH_3$ | 4-$CH_3$ | H | $CH_2$ | $C_2H_5$ | H | H | 194 | β** |
| I-1-a-20 | $CH_3$ | $CH_3$ | 4-$CH_3$ | H | $CH_2$ | $C_2H_5$ | H | H | 253 | α** |
| I-1-a-21 | H | $CH_3$ | 4-$CH_3$ | 5-$CH_3$ | $CH_2$ | H | H | H | 219 | β** |
| I-1-a-22 | $CH_3$ | $CH_3$ | 4-$CH_3$ | 3-$CH_3$ | $CH_2$ | $C_2H_5$ | H | H | 237 | β** |
| I-1-a-23 | $CH_3$ | $CH_3$ | 4-$CH_3$ | 3-$CH_3$ | $CH_2$ | $C_2H_5$ | H | H | 226 | α** |
| I-1-a-24 | H | $CH_3$ | H | 5-$CH_3$ | $CH_2$ | H | H | H | 96 | β** |
| I-1-a-25 | H | $CH_3$ | H | 5-$CH_3$ | $CH_2$ | H | H | H | 199 | α** |
| I-1-a-26 | $CH_3$ | $CH_3$ | 4-$CH_3$ | 3-$CH_3$ | $CH_2$ | $CH_3$ | H | H | 229 | β** |
| I-1-a-27 | $CH_3$ | $CH_3$ | 4-$CH_3$ | 3-$CH_3$ | $CH_2$ | $CH_3$ | H | H | 265 | α** |
| I-1-a-28 | H | $CH_3$ | 4-$CH_3$ | 5-$CH_3$ | $CH_2$ | $CH_3$ | H | H | 182 | β** |
| I-1-a-29 | H | $CH_3$ | 4-$CH_3$ | 5-$CH_3$ | $CH_2$ | $CH_3$ | H | H | 199 | α** |
| I-1-a-30 | H | $CH_3$ | H | 5-$CH_3$ | $CH_2$ | $C_2H_5$ | H | H | Wax | β** |
| I-1-a-31 | H | $CH_3$ | H | 5-$CH_3$ | $CH_2$ | $C_2H_5$ | H | H | 192 | α** |
| I-1-a-32 | $C_2H_5$ | Cl | 4-Cl | H | $CH_2$ | $C_3H_7$ | H | H | 78 | β** |
| I-1-a-33 | $C_2H_5$ | Cl | 4-Cl | H | $CH_2$ | $C_3H_7$ | H | H | 139 | α** |
| I-1-a-34 | $C_2H_5$ | Br | 4-$CH_3$ | H | —$(CH_2)_2$— | $OCH_3$ | H | H | 213 | α** |
| I-1-a-35 | $CH_3$ | $CH_3$ | 4-$CH_3$ | 3-$CH_3$ | $CH_2$ | H | H | H | 254 | β** |
| I-1-a-36 | $CH_3$ | $CH_3$ | 4-$CH_3$ | H | $CH_2$ | $CH_3$ | H | H | 130 | β** |
| I-1-a-37 | $C_2H_5$ | Br | 4-$CH_3$ | H | $CH_2$ | H | $CH_3$ | $CH_3$ | 247 | β** |
| I-1-a-38 | $CH_3$ | $CH_3$ | 4-$CH_3$ | H | $CH_2$ | $CH_3$ | H | H | 248 | α** |
| I-1-a-39 | $CH_3$ | $CH_3$ | 4-$CH_3$ | 3-$CH_3$ | $CH_2$ | H | H | H | 253 | α** |
| I-1-a-40 | $C_2H_5$ | Br | 4-$CH_3$ | H | —$(CH_2)_2$— | $OCH_3$ | H | H | 129 | β** |
| I-1-a-41 | $CH_3$ | $CH_3$ | 4-$CH_3$ | H | $CH_2$ | $C_3H_7$ | $CH_3$ | $CH_3$ | Wax | β** |
| I-1-a-42 | $CH_3$ | $CH_3$ | 4-$CH_3$ | H | $CH_2$ | $C_3H_7$ | $CH_3$ | $CH_3$ | 255 | α** |
| I-1-a-43 | $CH_3$ | $CH_3$ | 4-$CH_3$ | H | $CH_2$ | $C_3H_7$ | H | H | 211 | β** |
| I-1-a-44 | H | $CH_3$ | 4-$CH_3$ | 5-$CH_3$ | $CH_2$ | $C_2H_5$ | H | H | 87 | β** |
| I-1-a-45 | $CH_3$ | $CH_3$ | 4-$CH_3$ | H | —$(CH_2)_2$— | $OCH_3$ | H | H | Oil | β** |
| I-1-a-46 | $CH_3$ | $CH_3$ | 4-$CH_3$ | H | —$(CH_2)_2$— | $OCH_3$ | H | H | 175 | α** |
| I-1-a-47 | $C_2H_5$ | $C_2H_5$ | 4-$CH_3$ | H | $C_2$ | $C_3H_7$ | H | H | 133 | β** |

-continued

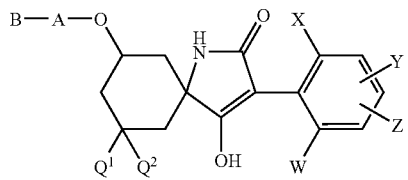
(I-1-a)

| Ex. No. | W | X | Y | Z | A | B | Q¹ | Q² | m.p. ° C. | Isomer |
|---|---|---|---|---|---|---|---|---|---|---|
| I-1-a-48 | $C_2H_5$ | $C_2H_5$ | 4-$CH_3$ | H | $C_2$ | $C_3H_7$ | H | H | 219 | α** |
| I-1-a-49 | $C_2H_5$ | Br | 4-Cl | H | $CH_2$ | $C_3H_7$ | H | H | 114 | β** |
| I-1-a-50 | $C_2H_5$ | Br | 4-Cl | H | $CH_2$ | $C_3H_7$ | H | H | 185 | α** |
| I-1-a-51 | $C_2H_5$ | Br | 4-Cl | H | $CH_2$ | $CH_3$ | H | H | 69 | β** |
| I-1-a-52 | $C_2H_5$ | Br | 4-Cl | H | $CH_2$ | H | H | H | 208 | β** |
| I-1-a-53 | $CH_3$ | $CH_3$ | 4-$CH_3$ | H | $CH_2$ | H | $CH_3$ | $CH_3$ | 274 | β** |
| I-1-a-54 | $C_2H_5$ | Br | 4-Cl | H | $CH_2$ | $CH_3$ | H | H | 223 | α** |
| I-1-a-55 | $C_2H_5$ | Br | 4-Cl | H | $CH_2$ | H | H | H | 215 | α** |
| I-1-a-56 | $C_2H_5$ | Br | 4-Cl | H | $CH_2$ | $C_2H_5$ | H | H | 96 | α** |
| I-1-a-57 | $C_2H_5$ | Br | 4-Cl | H | $CH_2$ | $C_2H_5$ | H | H | 80 | β** |
| I-1-a-58 | $CH_3$ | $CH_3$ | 4-$CH_3$ | H | $CH_2$ | H | H | H | 216 | β** |
| I-1-a-59 | $CH_3$ | $CH_3$ | 4-$CH_3$ | H | $CH_2$ | H | H | H | 267 | α** |
| I-1-a-60 | $C_2H_5$ | Br | 4-$CH_3$ | H | $CH_2$ | $C_3H_7$ | $CH_3$ | $CH_3$ | 225 | β** |
| I-1-a-61 | $C_2H_5$ | Br | 4-$CH_3$ | H | $CH_2$ | $C_3H_7$ | $CH_3$ | $CH_3$ | 270 | α** |
| I-1-a-62 | $C_2H_5$ | Br | 4-$CH_3$ | H | $CH_2$ | i-$C_3H_7$ | $CH_3$ | $CH_3$ | 207 | β** |
| I-1-a-63 | $CH_3$ | $C_2H_5$ | 4-$CH_3$ | H | $CH_2$ | $C_3H_7$ | H | H | 198 | β** |
| I-1-a-64 | $C_2H_5$ | $OCH_3$ | 4-Cl | H | $CH_2$ | $C_3H_7$ | H | H | 111-115 | β** |
| I-1-a-65 | $C_2H_5$ | $OC_2H_5$ | 4-Cl | H | $CH_2$ | $C_3H_7$ | H | H | *3.55 (m, 1H, OCH) 3.97 (m, 2H, $OCH_2$) | β** |
| I-1-a-66 | $C_2H_5$ | $OCH_3$ | 4-Cl | H | $CH_2$ | H | H | H | 175-180 | β** |
| I-1-a-67 | $C_2H_5$ | $OCH_3$ | 4-Cl | H | $CH_2$ | $CH_3$ | H | H | 87-97 | β** |
| I-1-a-68 | $C_2H_5$ | $OCH_3$ | 4-Cl | H | $CH_2$ | $C_2H_5$ | H | H | 182-184 | β** |
| I-1-a-69 | $CH_3$ | $C_2H_5$ | 4-$CH_3$ | H | $CH_2$ | $C_3H_7$ | H | H | 199 | α** |
| I-1-a-70 | $CH_3$ | $C_2H_5$ | 4-$CH_3$ | H | $CH_2$ | H | H | H | 221 | α** |
| I-1-a-71 | $CH_3$ | $C_2H_5$ | 4-$CH_3$ | H | $CH_2$ | H | H | H | 88 | β** |
| I-1-a-72 | $CH_3$ | $C_2H_5$ | 4-Br | H | $CH_2$ | $C_2H_5$ | H | H | 209 | α** |
| I-1-a-73 | $CH_3$ | $C_2H_5$ | 4-Br | H | $CH_2$ | $C_2H_5$ | H | H | 175 | β** |
| I-1-a-74 | $CH_3$ | $C_2H_5$ | 4-Br | H | $CH_2$ | $C_3H_7$ | H | H | 194 | α** |
| I-1-a-75 | $CH_3$ | $C_2H_5$ | 4-Br | H | $CH_2$ | $C_3H_7$ | H | H | 163 | β** |
| I-1-a-76 | $CH_3$ | $C_2H_5$ | 4-Br | H | $CH_2$ | $CH_3$ | H | H | 218 | α** |
| I-1-a-77 | $CH_3$ | $C_2H_5$ | 4-Br | H | $CH_2$ | $CH_3$ | H | H | 92 | β** |
| I-1-a-78 | $CH_3$ | $C_2H_5$ | 4-Br | H | $CH_2$ | H | H | H | 206 | α** |
| I-1-a-79 | $CH_3$ | $C_2H_5$ | 4-Br | H | $CH_2$ | H | H | H | 89 | β** |
| I-1-a-80 | H | $CH_3$ | 4-$CH_3$ | 5-$CH_3$ | $CH_2$ | $C_2H_5$ | H | H | 198 | α** |
| I-1-a-81 | Cl | $H_3CO-(CH_2)_2-O-$ | 4-$CH_3$ | H | $CH_2$ | $C_3H_7$ | H | H | Wax | β** |
| I-1-a-82 | Cl | Cl | 4-Cl | H | $-(CH_2)_2-$ | $OCH_3$ | H | H | 209 | α** |
| I-1-a-83 | Cl | Cl | 4-Cl | H | $CH_2$ | $C_3H_7$ | H | H | 99 | β** |
| I-1-a-84 | Cl | Cl | 4-Cl | H | $-(CH_2)_2-$ | $OCH_3$ | H | H | 162 | β** |
| I-1-a-85 | H | $C_2H_5$ | 4-Cl | H | $-(CH_2)_2-$ | $OCH_3$ | H | H | 117 | β** |
| I-1-a-86 | H | $C_2H_5$ | 4-Cl | H | $-(CH_2)_2-$ | $OCH_3$ | H | H | Wax | α** |
| I-1-a-87 | $C_2H_5$ | Cl | 4-$CH_3$ | H | $CH_2$ | $C_3H_7$ | H | H | 1) | β** |
| I-1-a-88 | H | $CH_3$ | H | 5-$CH_3$ | $CH_2$ | ▷— | H | H | 197 | α** |
| I-1-a-89 | $CH_3$ | $CH_3$ | 4-$CH_3$ | H | $CH_2$ | ▷— | H | H | 113 | α** |
| I-1-a-90 | $CH_3$ | $CH_3$ | 4-$CH_3$ | H | $CH_2$ | ▷— | H | H | 110 | β** |
| I-1-a-91 | $C_2H_5$ | $OCH_3$ | 4-Cl | H | $-(CH_2)_2-$ | $OCH_3$ | H | H | 165 | α** |
| I-1-a-92 | $C_2H_5$ | $OCH_3$ | 4-Cl | H | $-(CH_2)_2-$ | $OCH_3$ | H | H | Oil | β** |
| I-1-a-93 | H | $CH_3$ | H | 5-$CH_3$ | $CH_2$ | ▷— | H | H | 129 | β** |

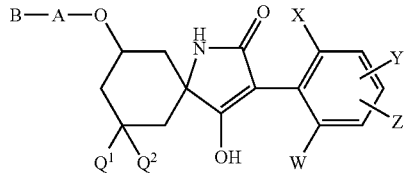

(I-1-a)

| Ex. No. | W | X | Y | Z | A | B | Q¹ | Q² | m.p. °C. | Isomer |
|---|---|---|---|---|---|---|---|---|---|---|
| I-1-a-94 | $C_2H_5$ | Br | 4-$CH_3$ | H | $CH_2$ | cyclopropyl | H | H | 191 | β** |
| I-1-a-95 | $C_2H_5$ | Br | 4-$CH_3$ | H | $CH_2$ | cyclopropyl | H | H | 238 | α** |

\*$^1$H-NMR (400 MHz, $d_6$-DMSO): shift δ in ppm
\*\*Enriched isomer after purification by column chromatography on silica gel
1) $^1$H-NMR (400 MHz, $d_6$-DMSO): δ = 3.55 (m, 1 H, CHO), 7.00 (s, 1 H, Ar—H)

Example I-1-b-1

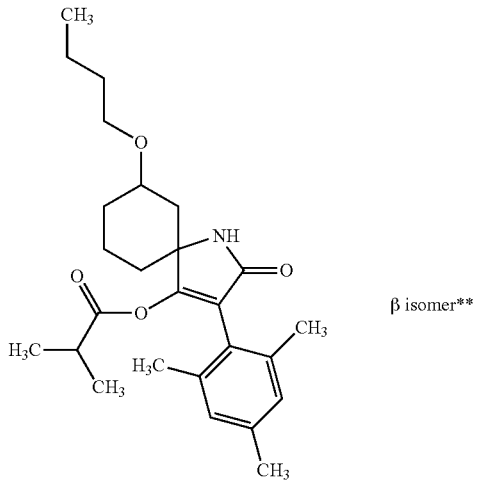 [SMILES: CCCCOC1CCCC2(C1)NC(=O)C(c1c(C)cc(C)cc1C)=C2OC(=O)C(C)C]

β isomer\*\*

In a 100 ml three-necked flask fitted with thermometer and reflux condenser, under argon, 0.25 g of the compound of Example I-1-a-1 is initially charged in 30 ml of anhydrous ethyl acetate and 0.1 ml of triethylamine (0.7 mmol). The reaction is catalysed with 10 mg of Steglich base and, under reflux, 0.08 ml of isobutyryl chloride in 2 ml of anhydrous ethyl acetate is added. The mixture is stirred for 1 hour. The reaction is monitored by thin-layer chromatography. The reaction mixture is concentrated under reduced pressure. The residue is then purified by column chromatography on silica gel (n-hexane:ethyl acetate 8:2).

Yield: 0.2 g (62.2% oftheory) m.p. 153° C.

enriched isomer after purification by column chromatography on silica gel

Analogously to Example (I-1-b-1) and in accordance with the general statements on the preparation, the following compounds of the formula (I-1-b) are obtained

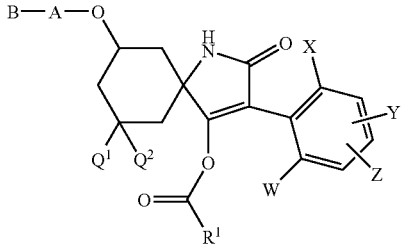

(I-1-b)

| Ex. No. | W | X | Y | Z | A | B | Q¹ | Q² | R¹ | m.p. °C. | Isomer** |
|---|---|---|---|---|---|---|---|---|---|---|---|
| I-1-b-2 | Br | $C_2H_5$ | 4-$CH_3$ | H | $CH_2$ | $C_3H_7$ | H | H | $H_3CO$—$CH_2$— | *2.26 (s, 3H, Ar-4-$\underline{CH_3}$) 4.07 (q, 2H, CO—$\underline{CH_2}$—O—) | α |
| I-1-b-3 | Br | $C_2H_5$ | 4-$CH_3$ | H | $CH_2$ | $C_3H_7$ | H | H | i-$C_3H_7$ | *2.26 (s, 3H, Ar-4-$\underline{CH_3}$) 3.81 (m, 1H, $\underline{CH}$—O) | α |
| I-1-b-4 | Br | $C_2H_5$ | 4-$CH_3$ | H | $CH_2$ | $C_2H_5$ | H | H | $H_3CO$—$CH_2$— | 169-172 | β |
| I-1-b-5 | Br | $C_2H_5$ | 4-$CH_3$ | H | $CH_2$ | $C_2H_5$ | H | H | i-$C_3H_7$ | 184-187 | β |
| I-1-b-6 | $C_2H_5$ | Cl | 4-Br | H | $CH_2$ | $C_3H_7$ | H | H | $H_3CO$—$CH_2$— | *3.83 (m, br, 1H, O—$\underline{CH}$) 7.33 (d, 1H, Ar—$\underline{H}$) | α |
| I-1-b-7 | $C_2H_5$ | Cl | 4-Br | H | $CH_2$ | $C_3H_7$ | H | H | i-$C_3H_7$ | *1.06 (m, 6H, CH($\underline{CH_3}$) 7.32 (d, 1H, Ar—$\underline{H}$) | α |

-continued (I-1-b)

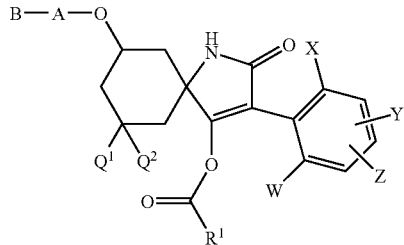

| Ex. No. | W | X | Y | Z | A | B | Q¹ | Q² | R¹ | m.p. ° C. | Isomer** |
|---|---|---|---|---|---|---|---|---|---|---|---|
| I-1-b-8 | C₂H₅ | Cl | 4-Br | H | CH₂ | C₃H₇ | H | H | H₃CO—CH₂— | *3.42 (m, 3H, C<u>H</u>—O, CH₂O), 4.08 (q, 2H, COC<u>H</u>₂O) | β |
| I-1-b-9 | C₂H₅ | Cl | 4-Br | H | CH₂ | C₃H₇ | H | H | i-C₃H₇ | *1.06 (m, 6H, CH(C<u>H</u>₃)₂), 7.33 (d, 1H, Ar—<u>H</u>) | β |
| I-1-b-10 | Br | C₂H₅ | 4-CH₃ | H | CH₂ | CH₃ | H | H | i-C₃H₇ | *1.06 (m, 6H, CH(C<u>H</u>₃)₂) 2.29 (s, 3H, Ar—C<u>H</u>₃) | β |
| I-1-b-11 | Br | C₂H₅ | 4-CH₃ | H | CH₂ | H | H | H | i-C₃H₇ | *1.06 (m, 6H, CH(C<u>H</u>₃)₂) 3.34 (s, 3H, OC<u>H</u>₃) | β |
| I-1-b-12 | Br | C₂H₅ | 4-CH₃ | H | CH₂ | H | H | H | H₃CO—CH₂— | 188-189 | β |
| I-1-b-13 | Br | C₂H₅ | 4-CH₃ | H | CH₂ | C₃H₇ | H | H | i-C₃H₇ | 166-167 | β |
| I-1-b-14 | Br | C₂H₅ | 4-CH₃ | H | CH₂ | C₃H₇ | H | H | H₃CO—CH₂— | *2.29 (s, 3H, Ar—C<u>H</u>₃) 4.07 (q, 2H, CO—C<u>H</u>₂O) | β |
| I-1-b-15 | Br | C₂H₅ | 4-CH₃ | H | CH₂ | CH₃ | H | H | H₃CO—CH₂— | 202-205 | β |
| I-1-b-16 | CH₃ | CH₃ | 4-CH₃ | H | CH₂ | C₃H₇ | H | H | i-C₃H₇ | *2.52 (m, 1H, C<u>H</u>(CH₃)₂) 6.81 (s, 2H, ArH) | β |
| I-1-b-17 | CH₃ | CH₃ | 4-CH₃ | H | CH₂ | C₂H₅ | H | H | i-C₃H₇ | 178 | β |
| I-1-b-18 | C₂H₅ | Cl | 4-Cl | H | CH₂ | C₃H₇ | H | H | i-C₃H₇ | 176 | β |
| I-1-b-19 | C₂H₅ | Cl | 4-Cl | H | CH₂ | C₃H₇ | H | H | H₅C₂O—CH₂— | 157-159 | β |
| I-1-b-20 | C₂H₅ | Cl | 4-Cl | H | CH₂ | C₃H₇ | H | H | H₃CO—CH₂— | *2.64 (m, 2H, Ar—C<u>H</u>₂) 3.30 (s, 3H, OCH₃) | β |
| I-1-b-21 | CH₃ | CH₃ | 4-CH₃ | H | (CH₂)₂ | OCH₃ | H | H | H₃CO—CH₂— | *2.25 (s, 3H, ArC<u>H</u>₃) 3.97 (s, 2H, O—C<u>H</u>₂)) | β |
| I-1-b-22 | CH₃ | CH₃ | 4-CH₃ | H | CH₂ | C₃H₇ | H | H | H₃CO—CH₂— | *2.25 (s, 3H, ArC<u>H</u>₃) 3.16 (s, 3H, OCH₃) | β |
| I-1-b-23 | C₂H₅ | Br | 4-Cl | H | CH₂ | C₃H₇ | H | H | H₃CO—CH₂— | 157 | β |
| I-1-b-24 | C₂H₅ | Br | 4-CH₃ | H | CH₂ | H | CH₃ | CH₃ | H₃CO—CH₂— | 218 | β |
| I-1-b-25 | C₂H₅ | C₂H₅ | 4-CH₃ | H | CH₂ | C₃H₇ | H | H | H₃CO—CH₂— | 156 | β |
| I-1-b-26 | CH₃ | CH₃ | 4-CH₃ | H | CH₂ | C₃H₇ | H | H | H₅C₂O—CH₂— | *2.24 (s, 3H, ArC<u>H</u>₃) 3.28 (q, 2H, OC<u>H</u>₂—CH₃) | β |
| I-1-b-27 | C₂H₅ | C₂H₅ | 4-CH₃ | H | CH₂ | C₃H₇ | H | H | H₅C₂O—CH₂— | 139-141 | β |
| I-1-b-28 | CH₃ | CH₃ | 4-CH₃ | H | CH₂ | C₃H₇ | H | H | t-C₄H₉ | 190 | β |
| I-1-b-29 | C₂H₅ | Br | 4-CH₃ | H | CH₂ | i-C₃H₇ | CH₃ | CH₃ | i-C₃H₇ | 180-183 | β |
| I-1-b-30 | C₂H₅ | Br | 4-CH₃ | H | CH₂ | H | CH₃ | CH₃ | i-C₃H₇ | 185-198 | β |
| I-1-b-31 | C₂H₅ | Br | 4-Cl | H | CH₂ | C₃H₇ | H | H | △ | 224-226 | β |
| I-1-b-32 | CH₃ | CH₃ | 4-CH₃ | H | CH₂ | C₃H₇ | H | H | 2-Cl—C₆H₄— | 192-194 | β |
| I-1-b-33 | C₂H₅ | Br | 4-Cl | H | CH₂ | C₃H₇ | H | H | 2-Cl—C₆H₄— | 216 | β |
| I-1-b-34 | CH₃ | CH₃ | 4-CH₃ | H | CH₂ | C₃H₇ | H | H | △ | 199 | β |
| I-1-b-35 | CH₃ | CH₃ | 4-CH₃ | H | CH₂ | C₃H₇ | H | H | 4-Cl—C₆H₄—O—CH₂— | 168 | β |
| I-1-b-36 | CH₃ | CH₃ | 4-CH₃ | H | CH₂ | C₂H₅ | H | H | H₃CO—CH₂— | 142-143 | β |
| I-1-b-37 | CH₃ | C₂H₅ | 4-CH₃ | H | CH₂ | H | H | H | H₃CO—CH₂— | 195-197 | β |
| I-1-b-38 | CH₃ | C₂H₅ | 4-CH₃ | H | CH₂ | C₃H₇ | H | H | H₃CO—CH₂— | 150-152 | β |
| I-1-b-39 | CH₃ | C₂H₅ | 4-Br | H | CH₂ | H | H | H | H₃CO—CH₂— | 163-165 | β |
| I-1-b-40 | CH₃ | C₂H₅ | 4-Br | H | CH₂ | CH₃ | H | H | H₃CO—CH₂— | 187-189 | β |
| I-1-b-41 | CH₃ | C₂H₅ | 4-Br | H | CH₂ | C₂H₅ | H | H | H₃CO—CH₂— | *2.50 (m, 2H, ArC<u>H</u>₂) 3.25 (s, 3H, OCH₃) | β |

-continued

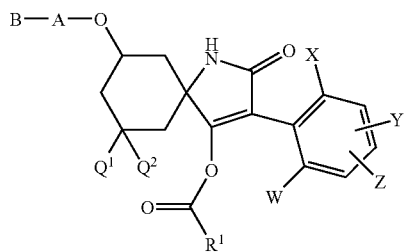

(I-1-b)

| Ex. No. | W | X | Y | Z | A | B | Q¹ | Q² | R¹ | m.p. ° C. | Isomer** |
|---|---|---|---|---|---|---|---|---|---|---|---|
| I-1-b-42 | $CH_3$ | $C_2H_5$ | 4-Br | H | $CH_2$ | $C_3H_7$ | H | H | $H_3CO-CH_2-$ | 150-152 | β |
| I-1-b-43 | $CH_3$ | $CH_3$ | 4-$CH_3$ | H | $CH_2$ | $C_3H_7$ | H | H | 2-thienyl | 219-222 | β |
| I-1-b-44 | $C_2H_5$ | Br | 4-Cl | H | $CH_2$ | $C_3H_7$ | H | H | 2-thienyl | *268 (m, 2H, Ar-$\underline{CH_2}$)<br>7.66 (dd, 1H, thienyl-$H_5$) | β |
| I-1-b-45 | $CH_3$ | $CH_3$ | 4-$CH_3$ | H | $CH_2$ | $C_3H_7$ | H | H | $Cl-CH_2-$ | 177-180 | β |
| I-1-b-46 | $CH_3$ | $CH_3$ | 4-$CH_3$ | H | $CH_2$ | $C_3H_7$ | H | H | 4-methylpyridyl | 252-254 | β |
| I-1-b-47 | $CH_3$ | $C_2H_5$ | 4-Br | H | $CH_2$ | H | H | H | $i-C_3H_7$ | *1.01 (dt, 6H, CH($\underline{CH_3}$)$_2$)<br>3.34 (s, 3H, $OCH_3$) | β |
| I-1-b-48 | $CH_3$ | $C_2H_5$ | 4-Br | H | $CH_2$ | $CH_3$ | H | H | $i-C_3H_7$ | *1.01 (dt, 6H, CH($\underline{CH_3}$)$_2$)<br>2.21 (d, 3H, Ar$\underline{CH_3}$) | β |
| I-1-b-49 | $CH_3$ | $C_2H_5$ | 4-Br | H | $CH_2$ | $C_2H_5$ | H | H | $i-C_3H_7$ | *221 (d, 3H, Ar$\underline{CH_3}$)<br>3.48 (m, 3H, O$\underline{CH}$ and O$\underline{CH_3}$) | β |
| I-1-b-50 | $CH_3$ | $C_2H_5$ | 4-Br | H | $CH_2$ | $C_3H_7$ | H | H | $i-C_3H_7$ | *1.01 (dt, 6H, CH($\underline{CH_3}$)$_2$)<br>3.44 (m, 3H, O$\underline{CH}$ and O$\underline{CH_2}$) | β |
| I-1-b-51 | H | $C_2H_5$ | 4-Cl | H | $(CH_2)_2$ | $OCH_3$ | H | H | $i-C_3H_7$ | *1.04 (d, 6H, CH($\underline{CH_3}$)$_2$)<br>3.6 (m, 2H, O$\underline{CH_2}$) | β** |
| I-1-b-52 | $C_2H_5$ | Cl | 4-$CH_3$ | H | $CH_2$ | $C_3H_7$ | H | H | $i-C_3H_7$ | solidified foam | |
| I-1-b-53 | Cl | Cl | 4-Cl | H | $(CH_2)_2$ | $OCH_3$ | H | H | $i-C_3H_7$ | *1.14 (d, 6H, CH($\underline{CH_3}$)$_2$)<br>3.59 (m, 4H, 2 × O-$\underline{CH_2}$) | |

*$^1$H-NMR (300 MHz, CDCl$_3$): shifts δ in ppm.

** Enriched isomer after purification by column chromatography or recrystallization

Example I-1-c-1

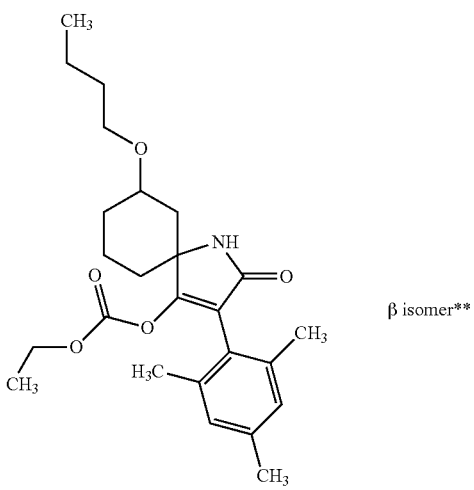 [SMILES: CCCCOC1CCCC2(C1)NC(=O)C(c1c(C)cc(C)cc1C)=C2OC(=O)OCC]

β isomer**

In a 100 ml three-necked flask fitted with thermometer and reflux condenser, under argon, 0.715 g of the compound of Example I-1-a-1 is initially charged in 30 ml of anhydrous dichloromethane and 0.28 ml of triethylamine, and at 20° C., 0.22 g (0.002 mol) of ethyl chloroformate in 2 ml of anhydrous dichloromethane is added. The mixture is stirred for 1 hour. The reaction mixture is concentrated under reduced pressure.

The residue is then purified by column chromatography on silica gel (n-hexane:ethyl acetate 8:2)

Yield: 0.38 g (44% of theory), mp. 181° C.

Enriched isomer after purification by column chromatography on silica gel.

Analogously to Example (I-1-c-1) and in accordance with the general statements on the preparation, the following compounds of the formula (I-1-c) are obtained

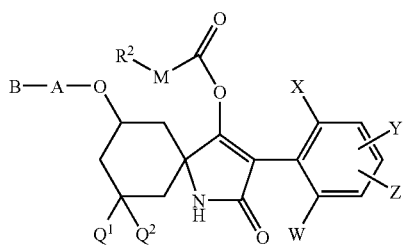

(I-1-c)

| Ex. No. | W | X | Y | Z | A | B | $Q^1$ | $Q^2$ | M | $R^2$ | m.p. ° C. | Isomer** |
|---|---|---|---|---|---|---|---|---|---|---|---|---|
| I-1-c-2 | $CH_3$ | $CH_3$ | 4-$CH_3$ | H | $CH_2$ | H | H | H | O | $C_2H_5$ | Oil *3.73 (m, 1H, O—CH) 3.98 (q, 2H, O—CH$_2$) | α |
| I-1-c-3 | $CH_3$ | $CH_3$ | 4-$CH_3$ | H | $CH_2$ | H | H | H | O | $C_2H_5$ | 179 | β |
| I-1-c-4 | $CH_3$ | $CH_3$ | 4-$CH_3$ | H | $CH_2$ | $C_3H_7$ | H | H | O | $C_2H_5$ | *2.24 (s, 3H, Ar-4-CH$_3$) 4.00 (q, 2H, O—CH$_2$CH$_3$) | α |
| I-1-c-5 | Br | $C_2H_5$ | 4-$CH_3$ | H | $CH_2$ | $C_3H_7$ | H | H | O | $C_2H_5$ | *2.31 (s, 3H, Ar—CH$_3$) 3.83 (m, 1H, CH O) | α |
| I-1-c-6 | Br | $C_2H_5$ | 4-$CH_3$ | H | $CH_2$ | $C_2H_5$ | H | H | O | $C_2H_5$ | 188-191 | β |
| I-1-c-7 | $C_2H_5$ | Cl | 4-Br | H | $CH_2$ | $C_3H_7$ | H | H | O | $C_2H_5$ | *3.83 (m, 1H, CHO) 4.08 (q, 2H, O—CH$_2$CH$_3$) | α |
| I-1-c-8 | $C_2H_5$ | Cl | 4-Br | H | $CH_2$ | $C_3H_7$ | H | H | O | $C_2H_5$ | 188 | β |
| I-1-c-9 | Br | $C_2H_5$ | 4-$CH_3$ | H | $CH_2$ | $CH_3$ | H | H | O | $C_2H_5$ | *2.31 (s, 3H, Ar-4-CH$_3$), 3.47 (m, 1H, CH—O), 4.07 (q, C(O)—O—CH$_2$) | β |
| I-1-c-10 | Br | $C_2H_5$ | 4-$CH_3$ | H | $CH_2$ | H | H | H | O | $C_2H_5$ | 182-185 | β |
| I-1-c-11 | Br | $C_2H_5$ | 4-$CH_3$ | H | $CH_2$ | $C_3H_7$ | H | H | O | $C_2H_5$ | 182-183 | β |
| I-1-c-12 | $CH_3$ | $CH_3$ | 4-$CH_3$ | 3-$CH_3$ | $CH_2$ | $CH_3$ | H | H | O | $C_2H_5$ | 192 | β |
| I-1-c-13 | H | $CH_3$ | H | 5-$CH_3$ | $CH_2$ | $C_2H_5$ | H | H | O | $C_2H_5$ | Wax | β |
| I-1-c-14 | $CH_3$ | $CH_3$ | 4-$CH_3$ | H | $CH_2$ | H | $CH_3$ | $CH_3$ | O | $C_2H_5$ | Wax | β |
| I-1-c-15 | $C_2H_5$ | Cl | 4-Cl | H | $CH_2$ | $C_3H_7$ | H | H | O | $C_2H_5$ | 123 | β |
| I-1-c-16 | $CH_3$ | $CH_3$ | 4-$CH_3$ | H | $CH_2$ | $C_3H_7$ | H | H | O | $C_2H_5$ | 190-193 | β |
| I-1-c-17 | $CH_3$ | $CH_3$ | 4-$CH_3$ | H | $CH_2$ | $C_2H_5$ | H | H | O | $C_2H_5$ | 185-188 | β |
| I-1-c-18 | $CH_3$ | $CH_3$ | 4-$CH_3$ | H | $(CH_2)_2$ | $OCH_3$ | H | H | O | $C_2H_5$ | 165-170 | β |
| I-1-c-19 | $CH_3$ | $CH_3$ | 4-$CH_3$ | H | $CH_2$ | $C_3H_7$ | H | H | O | $C_2H_5$ | 150-154 | β |
| I-1-c-20 | $C_2H_5$ | Br | 4-$CH_3$ | H | $CH_2$ | H | $CH_3$ | $CH_3$ | O | $C_2H_5$ | 206-208 | β |
| I-1-c-21 | $C_2H_5$ | $C_2H_5$ | 4-$CH_3$ | H | $CH_2$ | $C_3H_7$ | H | H | O | $C_2H_5$ | 194-197 | β |
| I-1-c-22 | $C_2H_5$ | Br | 4-Cl | H | $CH_2$ | $C_3H_7$ | H | H | O | $C_2H_5$ | 202-204 | β |
| I-1-c-23 | $C_2H_5$ | $OC_2H_5$ | 4-Cl | H | $CH_2$ | $C_3H_7$ | H | H | O | $C_2H_5$ | 168-172 | β |
| I-1-c-24 | $C_2H_5$ | $OCH_3$ | 4-Cl | H | $CH_2$ | $C_2H_5$ | H | H | O | $C_2H_5$ | 148-156 | β |
| I-1-c-25 | $C_2H_5$ | $OCH_3$ | 4-Cl | H | $CH_2$ | $CH_3$ | H | H | O | $C_2H_5$ | *2.55 (m, 2H, ArCH$_2$) 4.03 (q, 2H, O—CH$_2$) | β |
| I-1-c-26 | $C_2H_5$ | $OCH_3$ | 4-Cl | H | $CH_2$ | $C_3H_7$ | H | H | O | $C_2H_5$ | 155-163 | β |
| I-1-c-27 | $C_2H_5$ | $OCH_3$ | 4-Cl | H | $CH_2$ | H | H | H | O | $C_2H_5$ | 181-187 | β |
| I-1-c-28 | $C_2H_5$ | Br | 4-$CH_3$ | H | $CH_2$ | $C_3H_7$ | H | H | O | $C_2H_5$ | 156-158 | β |
| I-1-c-29 | $C_2H_5$ | Br | 4-$CH_3$ | H | $CH_2$ | i-$C_3H_7$ | $CH_3$ | $CH_3$ | O | $C_2H_5$ | *2.29 (s, 3H, ArCH$_3$) 4.05 (q, 2H, O—CH$_2$) | β |

-continued (I-1-c)

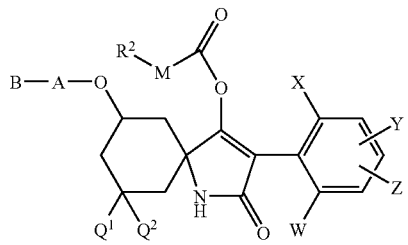

| Ex. No. | W | X | Y | Z | A | B | Q¹ | Q² | M | R² | m.p. °C. | Isomer** |
|---|---|---|---|---|---|---|---|---|---|---|---|---|
| I-1-c-30 | CH₃ | C₂H₅ | 4-CH₃ | H | CH₂ | H | H | H | O | C₂H₅ | 165-167 | β |
| I-1-c-31 | CH₃ | C₂H₅ | 4-CH₃ | H | CH₂ | C₃H₇ | H | H | O | C₂H₅ | 185-188 | β |
| I-1-c-32 | C₂H₅ | Br | 4-Cl | H | CH₂ | H | H | H | O | C₂H₅ | *2.62 (m, 2H, ArCH₂) 4.07 (q, 2H, OCH₂) | β |
| I-1-c-33 | CH₃ | C₂H₅ | 4-Br | H | CH₂ | H | H | H | O | C₂H₅ | *2.21 (s, 3H, ArCH₃) 4.04 (q, 2H, OCH₂) | β |
| I-1-c-34 | CH₃ | C₂H₅ | 4-Br | H | CH₂ | CH₃ | H | H | O | C₂H₅ | 200-202 | β |
| I-1-c-35 | CH₃ | C₂H₅ | 4-Br | H | CH₂ | C₂H₅ | H | H | O | C₂H₅ | *2.52 (m, 2H, ArCH₂) 4.04 (q, 2H, OCH₂) | β |
| I-1-c-36 | CH₃ | C₂H₅ | 4-Br | H | CH₂ | C₃H₇ | H | H | O | C₂H₅ | 192-193 | β |
| I-1-c-37 | C₂H₅ | Br | 4-Cl | H | CH₂ | C₃H₇ | H | H | O | CH₂=CH—CH₂— | 171-180 | β |
| I-1-c-38 | CH₃ | CH₃ | 4-CH₃ | H | CH₂ | C₃H₇ | H | H | O | t-C₄H₉—CH₂— | 212-214 | β |
| I-1-c-39 | C₂H₅ | Br | 4-Cl | H | CH₂ | C₃H₇ | H | H | O | t-C₄H₉—CH₂— | 240-243 | β |
| I-1-c-40 | CH₃ | CH₃ | 4-CH₃ | H | CH₂ | C₃H₇ | H | H | O | CH₂=CH—CH₂— | 159-167 | β |
| I-1-c-41 | CH₃ | CH₃ | 4-CH₃ | H | CH₂ | C₃H₇ | H | H | O | C₆H₅—CH₂— | *2.29 (s, 3H, ArCH₃) 4.96 (s, 2H, O—CH₂Ar) | β |
| I-1-c-42 | C₂H₅ | Br | 4-Cl | H | CH₂ | C₃H₇ | H | H | O | C₆H₅—CH₂— | 171-174 | β |
| I-1-c-43 | H | C₂H₅ | 4-Cl | H | —(CH₂)₂— | OCH₃ | H | H | O | C₂H₅ | *3.6 (m, 2H, O—CH₂) 4.05 (q, 2H, CO—O—CH₂) | β** |
| I-1-c-44 | C₂H₅ | Cl | 4-CH₃ | H | CH₂ | C₃H₇ | H | H | O | C₂H₅ | 186-190 | β** |
| I-1-c-45 | C₂H₅ | OCH₃ | 4-CH₃ | H | CH₂ | C₃H₇ | H | H | O | C₂H₅ | 178-181 | β** |

*¹H-NMR (400 MHz, CD₃CN): shift δ in ppm
**Enriched isomer after purification by column chromatography or by recrystallization Example I-1-c-46

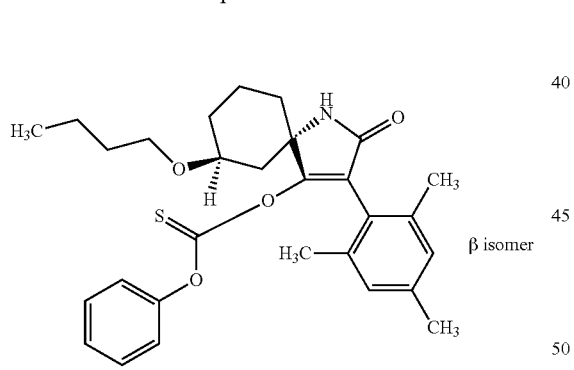

β isomer

Example I-1-d-1

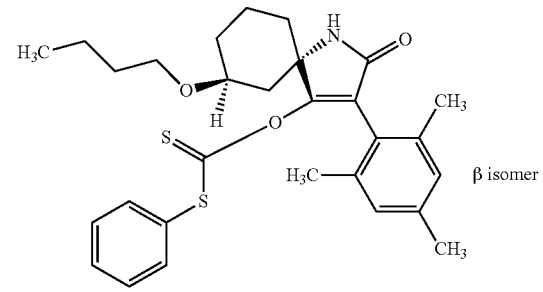

β isomer 0.214 g of the compound of Example I-1-a-43 (0.6 mmol) is initially charged in 10 ml of dichloromethane, and 0.10 ml of triethylamine (0.72 mmol, 1.2 eq) is added. 0.09 ml of O-phenyl chlorothioformate (0.66 mmol, 1.1 eq) is added, and the mixture is stirred at room temperature over the weekend. 2.5% strength sodium carbonate solution is added, the mixture is then extracted and the extract is dried using sodium sulphate and purified by column chromatography using ethyl acetate/n-heptane (3:7 to 100:0). This gives 0.084 g (28.4%) of a solid (m.p.: 192-94° C.).

Example I-1-c-47 with m.p. 166-168° C. is obtained analogously to Example I-1-c-46

0.063 g (0.176 mmol) of the compound of Ex. No. I-1-a-43 is initially charged in 10 ml of dichloromethane, and 0.03 ml of triethylamine is added. 0.02 ml of methanesulphonyl chloride is added a little at a time, and the mixture is stirred at room temperature for 24 h. 5% strength NaHCO$_3$ solution is added, the organic phase is separated off and the aqueous phase is extracted with dichloromethane. The combined organic phases are dried with sodium sulphate and then, under reduced pressure, evaporated to dryness, and the residue obtained is purified chromatographically using ethyl acetate/n-heptane (gradient ¼ to ⅔).

Yield: 0.05 g (68% of theory), m.p. 183-184° C.

Analogously to Example (I-1-d-1) and in accordance with the general statements on the preparation, the following compounds of the formula (I-1-d) are obtained 0.143 g of the compound of Example I-1-a-43 (0.4 mmol) is dissolved in 8 ml of methanol, and 0.39 ml of a 40% strength methanolic solution of tetrabutylammonium hydroxide (1 eq) is added. After 4 h at room temperature, the mixture is concentrated and the residue formed is co-evaporated with methanol three times. This gives 0.3 g of a highly viscous oil as product in quantitative yield.

$^1$H-NM (CDCl$_3$): 3.44 ppm (q, 2H, OCH$_2$), 2.88 ppm (pseudo-t, 8H, NCH$_2$)

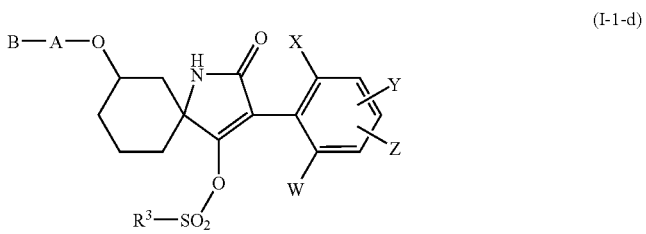

(I-1-d)

| Ex. No. | W | X | Y | Z | A | B | Q$^1$ | Q$^2$ | R$^3$ | m.p. ° C. | Isomer** |
|---|---|---|---|---|---|---|---|---|---|---|---|
| I-1-d-2 | CH$_3$ | CH$_3$ | 4-CH$_3$ | H | CH$_2$ | C$_3$H$_7$ | H | H | 4-CH$_3$—C$_6$H$_4$ | 237 | β |
| I-1-d-3 | C$_2$H$_5$ | Br | 4-Cl | H | CH$_2$ | C$_3$H$_7$ | H | H | 4-CH$_3$—C$_6$H$_4$ | 231-234 | β |

**Enriched isomer after purification by column chromatography or by recrystallization.

Example I-1-f-1

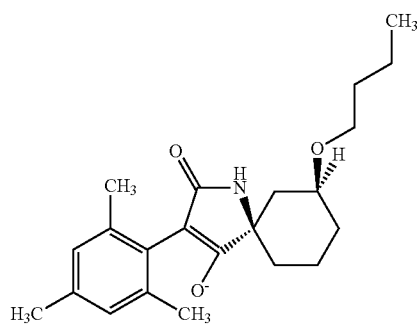

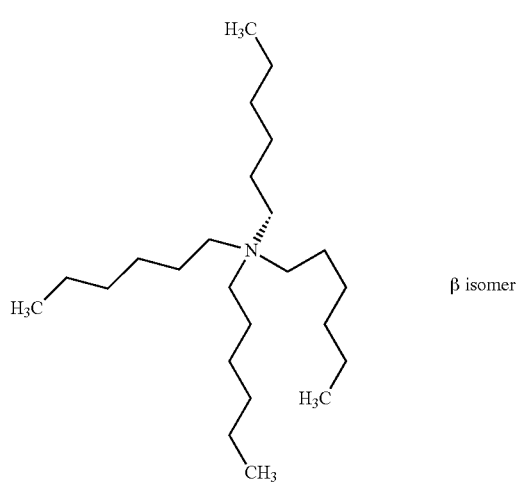

β isomer

Example I-1-g-1

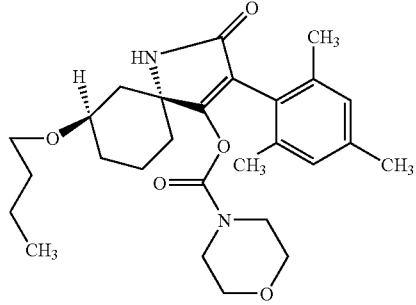 [SMILES: CCCCO[C@@H]1CCC[C@]2(C1)NC(=O)C(c1c(C)cc(C)cc1C)=C2OC(=O)N1CCOCC1]

0.179 g (0.5 mmol) of the compound of Example I-1-a-43 is dissolved in 5 ml of chloroform, and 0.09 g (1.2 eq) of morpholino-N-carbonyl chloride and 0.1 ml of triethylamine are added at room temperature. Under reflux, the mixture is heated at the boil for 24 h and then poured into saturated sodium chloride solution. The organic phase is separated off and then dried using sodium sulphate. Chromatographic purification on silica gel using an n-heptane/ethyl acetate gradient (4:1 to 1:4) gives 140 mg of a solid (yield 59%).

m.p. ° C.: 189-196° C.

Example II-1

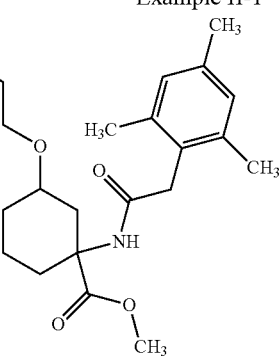

β isomer (enriched)

In a 100 ml three-necked flask fitted with thermometer and reflux condenser, under argon, 3.8 g of the compound of Example XIV-1 (0.015 mol) are initially charged in 50 ml of anhydrous tetrahydrofuran and 4.6 ml of triethylamine, and 2.95 g (0.01 mol) of mesityleneacetyl chloride in 5 ml of anhydrous tetrahydrofuran are added at 0-10° C. The reaction mixture is stirred for 1 hour and then concentrated under reduced pressure.

The residue is subsequently purified by column chromatography on silica gel (hexane:ethyl acetate 8:2).

Yield: 2.1 g (35% of theory) m.p. 98° C.

Analogously to Example (II-1) and in accordance with the general statements on the preparation, the following compounds of the formula (II) are obtained

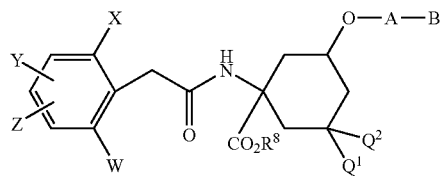

(II-1)

| Ex. No. | W | X | Y | Z | A | B | $Q^1$ | $Q^2$ | $R^8$ | m.p. ° C. | Isomer |
|---|---|---|---|---|---|---|---|---|---|---|---|
| II-2 | $CH_3$ | $CH_3$ | 4-$CH_3$ | H | $CH_2$ | H | H | H | $CH_3$ | Oil *2.89. 3.24 (2s, 3H, O$CH_3$) 3.57, 3.58 (2s, 3H, $CO_2CH_3$) | α:β about 1:1 |
| II-3 | $CH_3$ | $CH_3$ | 4-$CH_3$ | H | $CH_2$ | H | $CH_3$ | $CH_3$ | $CH_3$ | 148 | α |
| II-4 | $CH_3$ | $CH_3$ | 4-$CH_3$ | H | $CH_2$ | i-$C_3H_7$ | $CH_3$ | $CH_3$ | $CH_3$ | Oil *3.18-3.21 (m, 2H, O—$CH_2$) 0.86, 0.88 (2s, 6H, (C($CH_3$)$_2$) | α:β about 2:1 |
| II-5 | H | $CH_3$ | 5-(4-Cl—Ph) | H | $CH_2$ | $C_3H_7$ | H | H | $CH_3$ | Oil *0.79, 0.87 (2t, 3H, $CH_2$—$CH_3$) 3.32, 2.33 (2s, 3H, Ar$CH_3$) | α:β about 3:1 |
| II-6 | H | $CH_3$ | H | 5-$CH_3$ | $CH_2$ | H | H | H | $CH_3$ | *2.96, 3.23 (2s, 3H, O$CH_3$), 3.59 (2s, 3H, $CO_2CH_3$) | α:β** about 1:1 |
| II-7 | H | $CH_3$ | 4-$CH_3$ | 5-$CH_3$ | $CH_2$ | H | H | H | $CH_3$ | 125 | α:β** about 1:2 |
| II-8 | $CH_3$ | $CH_3$ | 4-$CH_3$ | 3-$CH_3$ | $CH_2$ | H | H | H | $CH_3$ | 136 | α:β** about 1:8 |
| II-9 | Br | $C_2H_5$ | 4-$CH_3$ | H | $CH_2$ | H | H | H | $CH_3$ | 114 | α:β** about 1:3 |
| II-10 | H | $CH_3$ | H | 5-$CH_3$ | $CH_2$ | $CH_3$ | H | H | $CH_3$ | Oil | α:β** about 3:2 |
| II-11 | H | $CH_3$ | 4-$CH_3$ | 5-$CH_3$ | $CH_2$ | $CH_3$ | H | H | $CH_3$ | 117 | α:β** about 1:35 |
| II-12 | $CH_3$ | $CH_3$ | 4-$CH_3$ | 3-$CH_3$ | $CH_2$ | $CH_3$ | H | H | $CH_3$ | 143 | α:β** about 1:28 |
| 11-13 | Br | $C_2H_5$ | 4-$CH_3$ | H | $CH_2$ | $CH_3$ | H | H | $CH_3$ | 128 | α:β** about 1:2 |
| II-14 | $CH_3$ | $CH_3$ | 4-$CH_3$ | H | $CH_2$ | $CH_3$ | H | H | $CH_3$ | 129 | α:β** about 1:59 |
| II-15 | Br | $C_2H_5$ | 4-$CH_3$ | H | $CH_2$ | $C_2H_5$ | H | H | $CH_3$ | 120 | α:β** about 1:83 |
| II-16 | Br | $C_2H_5$ | 4-$CH_3$ | H | $CH_2$ | $C_2H_5$ | H | H | $CH_3$ | Oil *3.57 (s, 3H, $CO_2CH_3$) | α:β** about 3.7:1 |
| II-17 | H | $CH_3$ | H | 5-$CH_3$ | $CH_2$ | $C_2H_5$ | H | H | $CH_3$ | Oil log P 3.87, 3.21 | α:β about 1:1 |
| II-18 | H | $CH_3$ | 4-$CH_3$ | 5-$CH_3$ | $CH_2$ | $C_2H_5$ | H | H | $CH_3$ | Oil, log P 4.2, 3.51 *6.94-6.94 (m, 2H, ArH) | α:β about 5:4 |
| II-19 | $CH_3$ | $CH_3$ | 4-$CH_3$ | 3-$CH_3$ | $CH_2$ | $C_2H_5$ | H | H | $CH_3$ | Oil *6.85, 6.88 (2s, 1H, ArH) | α:β about 1:1 |

-continued

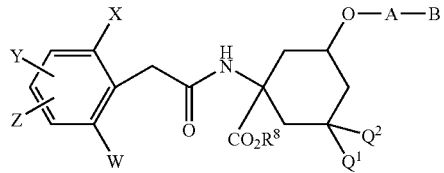

(II-1)

| Ex. No. | W | X | Y | Z | A | B | Q¹ | Q² | R⁸ | m.p. ° C. | Isomer |
|---|---|---|---|---|---|---|---|---|---|---|---|
| II-20 | $CH_3$ | $CH_3$ | 4-$CH_3$ | H | $CH_2$ | $C_2H_5$ | H | H | $CH_3$ | 125 | α:β about 1:54 |
| II-21 | $C_2H_5$ | Cl | 4-Br | H | $CH_2$ | $C_3H_7$ | H | H | $CH_3$ | Oil *2.65-2.68 (m, 2H, Ar—$\underline{CH_2}CH_3$) | α:β about 1:1 |
| II-22 | $C_2H_5$ | Cl | 4-Cl | H | $CH_2$ | $C_3H_7$ | H | H | $CH_3$ | Oil, log P 5.28, 4.46 *2.65-2.69 (m, 2H, Ar—$\underline{CH_2}CH_3$) | α:β about 1:1 |
| II-23 | Br | $C_2H_5$ | 4-$CH_3$ | H | $CH_2$ | $C_3H_7$ | H | H | $CH_3$ | Oil *2.63-2.66 (m, 2H, Ar—$\underline{CH_2}CH_3$) | α:β about 3:2 |
| II-24 | Br | $C_2H_5$ | 4-$CH_3$ | H | $CH_2$ | $CH_3$ | H | H | $CH_3$ | Oil *3.57 (s, 3H, $CO_2\underline{CH_3}$), 7.09 (s, 1H, Ar—H) | α**:β about 4.7:1 |
| II-25 | H | $CH_3$ | 4-$CH_3$ | 5-$CH_3$ | $CH_2$ | $CH_3$ | H | H | $CH_3$ | Oil log P 3.7, 3.04 | α + β** 2:1 |
| II-26 | Cl | Cl | 4-Cl | H | $(CH_2)_2$ | $OCH_3$ | H | H | $CH_3$ | 106 | α** |
| II-27 | Cl | $H_3CO$—$(CH_2)_2$—O— | 4-$CH_3$ | H | $CH_2$ | $C_3H_7$ | H | H | $CH_3$ | <60 | β** |
| II-28 | $C_2H_5$ | Br | 4-$CH_3$ | H | $(CH_2)_2$ | $OCH_3$ | H | H | $CH_3$ | Oil log P 3.64 | α** |
| II-29 | $C_2H_5$ | Br | 4-$CH_3$ | H | $CH_2$ | H | $CH_3$ | $CH_3$ | $CH_3$ | 133 | α + β** about 1:12 |
| II-30 | $CH_3$ | $CH_3$ | 4-$CH_3$ | H | $CH_2$ | $CH_3$ | H | H | $CH_3$ | Oil log P 3.74, 3.14 | α + β** about 3.5:1 |
| II-31 | $CH_3$ | $CH_3$ | 4-$CH_3$ | 3-$CH_3$ | $CH_2$ | H | H | H | $CH_3$ | Oil log P 3.48, 2.99 | α + β** about 5.4:1 |
| II-32 | $C_2H_5$ | Br | 4-$CH_3$ | H | $(CH_2)_2$ | $OCH_3$ | H | H | $CH_3$ | Oil log P 3.64, 3.18 | α + β** about 1:5.7 |
| II-33 | $CH_3$ | $CH_3$ | 4-$CH_3$ | H | $CH_2$ | $C_3H_7$ | $CH_3$ | $CH_3$ | $CH_3$ | Oil log P 5.26, 4.96 | α + β** about 1:2.8 |
| II-34 | $C_2H_5$ | $OCH_3$ | 4-Cl | H | $CH_2$ | $C_3H_7$ | H | H | $CH_3$ | Oil log P 4.85, 4.2 | α + β about 2:6.5 |
| II-35 | $CH_3$ | $CH_3$ | 4-$CH_3$ | H | $(CH_2)_2$ | $OCH_3$ | H | H | $CH_3$ | Oil log P 3.17, 2.76 | α + β about 1:1 |
| II-36 | $C_2H_5$ | $C_2H_5$ | 4-$CH_3$ | H | $CH_2$ | $C_3H_7$ | H | H | $CH_3$ | Oil log P 5.43, 4.70 | α + β** about 1:2 |
| II-37 | $C_2H_5$ | Br | 4-Cl | H | $CH_2$ | $C_3H_7$ | H | H | $CH_3$ | Oil log P 5.4, 4.56 | α + β** about 1:2.4 |
| II-38 | $C_2H_5$ | Br | 4-Cl | H | $CH_2$ | $CH_3$ | H | H | $CH_3$ | Oil log P 4.41, 3.61 | α + β about 1:1 |
| II-39 | $C_2H_5$ | Br | 4-Cl | H | $CH_2$ | H | H | H | $CH_3$ | Oil log P 3.96, 3.31 | α + β about 1:1.3 |
| II-40 | $CH_3$ | $CH_3$ | 4-$CH_3$ | H | $CH_2$ | H | $CH_3$ | $CH_3$ | $CH_3$ | 159 | α + β** about 1:19.7 |
| II-41 | $C_2H_5$ | Br | 4-Cl | H | $CH_2$ | $C_2H_5$ | H | H | $CH_3$ | Oil log P 4.95, 4.15 | α + β about 1:1 |

-continued

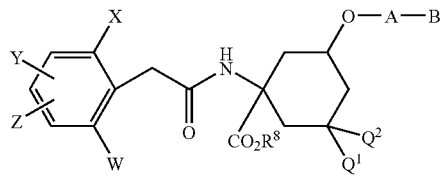
(II-1)

| Ex. No. | W | X | Y | Z | A | B | $Q^1$ | $Q^2$ | $R^8$ | m.p. ° C. | Isomer |
|---|---|---|---|---|---|---|---|---|---|---|---|
| II-42 | $C_2H_5$ | Br | 4-$CH_3$ | H | $CH_2$ | $C_3H_7$ | $CH_3$ | $CH_3$ | $CH_3$ | Oil<br>log P 5.62, 5.32 | α + β**<br>about 1:2.7 |
| II-43 | $C_2H_5$ | Br | 4-$CH_3$ | H | $CH_2$ | i-$C_3H_7$ | $CH_3$ | $CH_3$ | $CH_3$ | Oil<br>log P 5.69, 5.41 | α + β**<br>about 1:6.9 |
| II-44 | $CH_3$ | $C_2H_5$ | 4-$CH_3$ | H | $CH_2$ | $C_3H_7$ | H | H | $CH_3$ | Oil<br>log P 5.1, 4.6 | α + β**<br>about 1:3 |
| II-45 | $CH_3$ | $C_2H_5$ | 4-Br | H | $CH_2$ | $C_2H_5$ | H | H | $CH_3$ | Oil<br>log P 4.84, 4.09 | α + β**<br>about 1:2 |
| II-46 | $CH_3$ | $C_2H_5$ | 4-Br | H | $CH_2$ | $C_3H_7$ | H | H | $CH_3$ | Oil<br>log P 5.26, 4.49 | α + β**<br>about 1:3 |
| II-47 | $CH_3$ | $C_2H_5$ | 4-Br | H | $CH_2$ | $CH_3$ | H | H | $CH_3$ | Oil<br>log P 4.33, 3.61 | α + β<br>about 4:5 |
| II-48 | $CH_3$ | $C_2H_5$ | 4-Br | H | $CH_2$ | H | H | H | $CH_3$ | Oil<br>log P 3.85, 3.24 | α + β**<br>about 1:2 |
| II-49 | Cl | Cl | 4-Cl | H | $CH_2$ | $C_3H_7$ | H | H | $CH_3$ | 147 | β** |
| II-50 | Cl | Cl | 4-Cl | H | —$(CH_2)_2$— | $OCH_3$ | H | H | $CH_3$ | 164 | β** |
| II-51 | H | $C_2H_5$ | 4-Cl | H | $CH_2$ | $C_3H_7$ | H | H | $CH_3$ | 126 | β** |
| II-52 | $OCH_3$ | Cl | 4-$CH_3$ | H | $CH_2$ | $C_3H_7$ | H | H | $CH_3$ | 100 | β** |
| II-53 | $OC_2H_5$ | Cl | 4-$CH_3$ | H | $CH_2$ | $C_3H_7$ | H | H | $CH_3$ | 106 | β** |
| II-54 | $C_2H_5$ | $OCH_3$ | 4-Cl | H | —$(CH_2)_2$— | $OCH_3$ | H | H | $CH_3$ | Oil<br>log P 3.29, 2.97 | α + β**<br>about 1:1 |
| II-55 | H | $C_2H_5$ | 4-Cl | H | —$(CH_2)_2$— | $OCH_3$ | H | H | $CH_3$ | 120 | α + β**<br>about 1:20 |
| II-56 | H | $C_2H_5$ | 4-Cl | H | —$(CH_2)_2$— | $OCH_3$ | H | H | $CH_3$ | Oil<br>log P 3.35, 2.85 | α + β**<br>about 5:1 |
| II-57 | H | $CH_3$ | 5-$CH_3$ | H | $CH_2$ | cyclopropyl | H | H | $CH_3$ | Oil<br>log P 3.76, 3.11 | α + β<br>about 1:1 |
| II-58 | $CH_3$ | $CH_3$ | 4-$CH_3$ | H | $CH_2$ | cyclopropyl | H | H | $CH_3$ | Oil<br>log P 4.14, 3.51 | α + β<br>about 3:4 |
| II-59 | $C_2H_5$ | Br | 4-$CH_3$ | H | $CH_2$ | cyclopropyl | H | H | $CH_3$ | Oil<br>log P 4.58, 3.90 | α + β<br>about 3:4 |
| II-60 | $C_2H_5$ | Br | 4-Br | H | $CH_2$ | $C_3H_7$ | H | H | $CH_3$ | 115 | β** |
| II-61 | $C_2H_5$ | Cl | 4-$CH_3$ | H | $CH_2$ | $C_3H_7$ | H | H | $CH_3$ | 105 | β** |
| II-62 | $C_2H_5$ | $OCH_3$ | 4-$CH_3$ | H | $CH_2$ | $C_3H_7$ | H | H | $CH_3$ |  | β** |

*$^1$H-NMR (400 MHz, $CD_3CN$): shift δ in ppm
**Enriched isomer after purification by column chromatography on silica gel

Example XIV-1

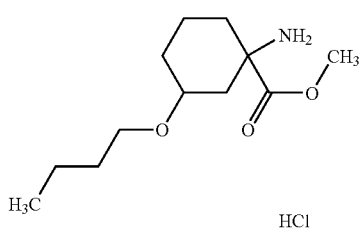 [SMILES: CCCCOC1CCCC(N)(C(=O)OC)C1 ; Cl]

Example XVII-1

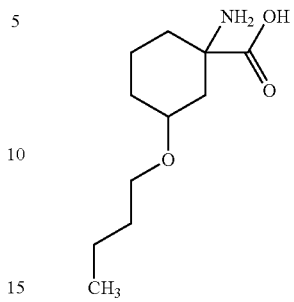

In a 3000 ml three-necked flask fitted with thermometer and reflux condenser, under argon, 120 g (1 eq.) of the compound of Example XVII-1 (contains potassium salts) are initially charged in 1200 ml of methanol at 0-5° C., and 52 ml of thionyl chloride are added dropwise. The mixture is stirred at 0° C. for 30 min and then at 40° C. for 1 day. The mixture is cooled to 5° C., the salt is filtered off with suction and the filtrate is concentrated under reduced pressure.

Yield: 108 g (72% of theory) of a viscous syrup over two steps starting with the hydantoin of the formula (XXI).

$^1$H-NMR (400 MHz, $d_6$-DMSO): δ=0.85-0.90 (m, 3H, $CH_2CH_3$), 3.73, 3.76 (2s, 3H, $OCH_3$) ppm.

Analogously to Example (XIV-1) and in accordance with the general statements on the preparation, the following compounds of the formula (XIV) are obtained in the form of their hydrochlorides In a 3000 ml three-necked flask fitted with thermometer and reflux condenser, under argon, 135 g of the compound of Example XXI-1 are suspended in 600 ml of 20% strength KOH. Under an atmosphere of nitrogen, the mixture is stirred under reflux. The reaction is monitored by thin-layer chromatography. Using a rotary evaporator the mixture is concentrated to about 25% of the original volume and, at 0-10° C., the pH is adjusted to 4.5 using concentrated HCl. The solution that remains is concentrated under reduced pressure, and the residue is dried.

Without further characterization, the total amount was used for the synthesis of Example XIV-1. The hydantoins of the formula (XXI) are novel and can be prepared by the subsequent process (J).

Analogously to Example (XVII-1) and in accordance with the general statements on the preparation, the following compounds of the formula (XVII) are obtained

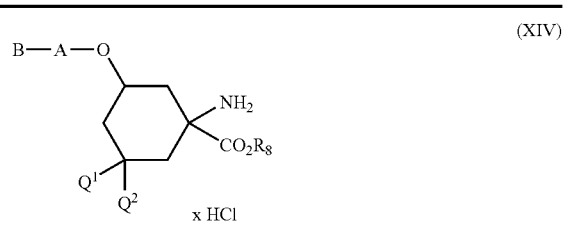

(XIV)

| Ex. No. | A | B | $Q^1$ | $Q^2$ | $R^8$ | $^1$H-NMR (400 MHz, $d_6$-DMSO) shifts δ in ppm |
|---|---|---|---|---|---|---|
| XIV-2 | $CH_2$ | H | H | H | $CH_3$ | 3.19, 3.24 (2s, 3H, O$CH_3$)<br>3.73, 3.76 (2s, 3H, $CO_2CH_3$) |
| XIV-3 | $CH_2$ | $CH_3$ | H | H | $CH_3$ | 1.06, 1.11 (2t, 3H, $CH_2$—$CH_3$)<br>3.73, 3.76 (2s, 3H, O$CH_3$) |
| XIV-4 | $CH_2$ | $C_2H_5$ | H | H | $CH_3$ | 0.82-0.88 (m, 3H, $CH_2$—$CH_3$)<br>3.73, 3.76 (2s, 3H, O$CH_3$) |
| XIV-5 | $CH_2$ | H | $CH_3$ | $CH_3$ | $CH_3$ | 3.17, 3.35 (2s, 3H, O$CH_3$)<br>3.75, 3.77 (2s, 3H, $CO_2CH_3$) |
| XIV-6 | $CH_2$ | i-$C_3H_7$ | $CH_3$ | $CH_3$ | $CH_3$ | 0.84, 0.85 (2s, 6H, $C(CH_3)_2$))<br>3.14-3.22 (m, 2H, O$CH_2$) |
| XIV-7 | $CH_2$ | △ | H | H | $CH_3$ | -0.15-0.02, 0.27-0.31 (2m, 4H, 2 cyclopr. —$CH_2$) 3.59 (2s, 3H, $CO_2CH_3$) |
| XIV-8 | $CH_2$ | (tetrahydrofuryl-methyl) | H | H | $CH_3$ | 3.58, 3.60, 3.61, 3.63 (4s, 3H, $CO_2CH_3$) |

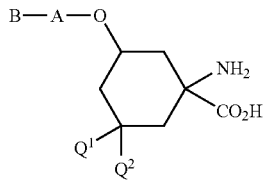

(XVII)

| Ex. No. | A | B | Q¹ | Q² |
|---|---|---|---|---|
| XVII-2 | $CH_2$ | H | H | H |
| XVII-3 | $CH_2$ | $CH_3$ | H | H |
| XVII-4 | $CH_2$ | $C_2H_5$ | H | H |
| XVII-5 | $CH_2$ | H | $CH_3$ | $CH_3$ |
| XVII-6 | $CH_2$ | $i\text{-}C_3H_7$ | $CH_3$ | $CH_3$ |
| XVII-7 | $CH_2$ |  | H | H |
| XVII-8 | $CH_2$ |  | H | H |

Example (I-2-a-1)

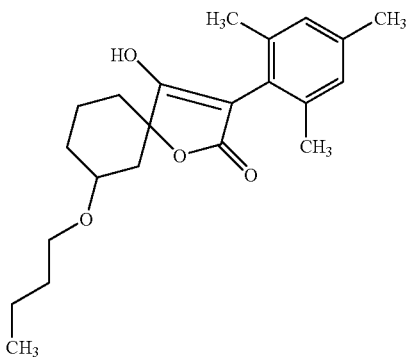 [SMILES: CCCCOC1CCCC2(C1)OC(=O)C(c1c(C)cc(C)cc1C)=C2O]

0.48 g (2 mmol) mesitylacetyl chloride and 0.39 g (2 mmol) of ethyl 1-hydroxy-3-n-butoxycyclohexylcarboxylate are heated at 140° C. for 10 h. After cooling, 5 ml of DMF is added, and 2.4 ml of 1M potassium tert-butoxide solution (2.4 mmol) are added dropwise.

The mixture is stirred at room temperature for 10 h. The solvent is then removed using a rotary evaporator. The residue is partitioned between water and ethyl acetate, the aqueous phase is acidified with 2N HCl and the product is extracted with ethyl acetate. The organic phase is dried and concentrated using a rotary evaporator.

Yield: 0.10 g (13% of theory)

log P 3.57

Analogously to Example (I-2-a-1) and in accordance with the general statements on the preparation, the following compounds of the formula (I-2-a) are obtained

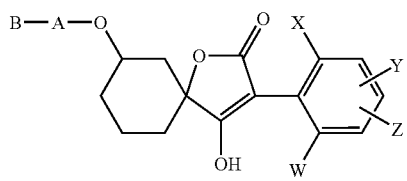

(I-2-a)

| Ex. No. | W | X | Y | Z | A | B | logP |
|---|---|---|---|---|---|---|---|
| I-2-a-2 | H | $CH_3$ | 5-(4-Cl—Ph) | 4-$CH_3$ | $CH_2$ | H | 3.4 |
| I-2-a-3 | $C_2H_5$ | $C_2H_5$ | 4-Br | H | $CH_2$ | H | 2.98 |
| I-2-a-4 | $CH_3$ | Br | 4-Cl | H | $CH_2$ | H | 2.46 |
| I-2-a-5 | Cl | Br | 4-$CH_3$ | H | $CH_2$ | H | 2.40 |
| I-2-a-6 | H | $CH_3$ | 4-Cl | H | $CH_2$ | H | 2.19 |
| I-2-a-7 | H | $CH_3$ | H | H | $CH_2$ | H | 1.81 |
| I-2-a-8 | H | $CH_3$ | 4-Cl | H | $CH_2$ | H | 2.11 |
| I-2-a-9 | H | Br | 4-$CH_3$ | 5-$CH_3$ | $CH_2$ | H | 2.35 |
| I-2-a-10 | $CH_3$ | $CH_3$ | 4-Br | H | $CH_2$ | H | 2.40 |
| I-2-a-11 | H | $CH_3$ | 4-$CH_3$ | 5-$CH_3$ | $CH_2$ | H | 2.21 |
| I-2-a-12 | $CH_3$ | $CH_3$ | 4-$CH_3$ | 3-$CH_3$ | $CH_2$ | H | 2.50 |
| I-2-a-13 | $CH_3$ | $C_2H_5$ | 4-Br | H | $CH_2$ | H | 2.74 |
| I-2-a-14 | $CH_3$ | $CH_3$ | 4-$CH_3$ | H | $CH_2$ | H | 2.31[1] |
| I-2-a-15 | Cl | Cl | H | H | $CH_2$ | H | 1.93 |
| I-2-a-16 | $CH_3$ | $OCH_3$ | 4-$CH_3$ | H | $CH_2$ | H | 2.10[1] |
| I-2-a-17 | $CH_3$ | $C_2H_5$ | 4-(4-Cl—Ph) | H | $CH_2$ | $CH_3$ | 4.19 |
| I-2-a-18 | H | Br | 4-Br | 5-$CH_3$ | $CH_2$ | H | 2.58 |
| I-2-a-19 | Br | Br | 4-$CH_3$ | H | $CH_2$ | H | 2.51 |
| I-2-a-20 | $CH_3$ | Cl | 4-Cl | H | $CH_2$ | H | 2.41 |
| I-2-a-21 | Cl | Cl | 4-$CH_3$ | H | $CH_2$ | H | 2.27 |
| I-2-a-22 | H | Cl | 4-$CH_3$ | H | $CH_2$ | H | 2.13 |
| I-2-a-23 | H | $CH_3$ | 5-Br | H | $CH_2$ | H | 2.30 |
| I-2-a-24 | H | 2-$CF_3$ | 4-Cl | H | $CH_2$ | H | 2.37 |
| I-2-a-25 | $CH_3$ | Cl | H | H | $CH_2$ | H | 1.92 |

-continued

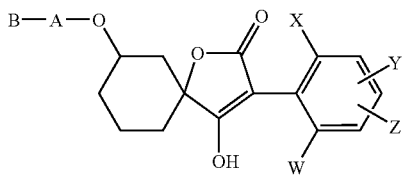
(I-2-a)

| Ex. No. | W | X | Y | Z | A | B | logP |
|---|---|---|---|---|---|---|---|
| I-2-a-26 | $C_2H_5$ | Br | 4-Br | H | $CH_2$ | H | 2.77 |
| I-2-a-27 | $CH_3$ | Cl | 4-$CH_3$ | H | $CH_2$ | H | 2.31 |
| I-2-a-28 | $CH_3$ | Br | 4-$CH_3$ | H | $CH_2$ | H | 2.36 |
| I-2-a-29 | Cl | Br | 4-$C_2H_5$ | H | $CH_2$ | H | 2.62 |
| I-2-a-30 | $CH_3$ | $CH_3$ | 5-(4-Cl—Ph) | 4-$CH_3$ | $CH_2$ | H | 3.60 |
| I-2-a-31 | H | Cl | 5-(4-Cl—Ph) | H | $CH_2$ | H | 3.14 |
| I-2-a-32 | H | $CH_3$ | 5-(4-Cl—Ph) | H | $CH_2$ | H | 3.19[1] |
| I-2-a-33 | H | $CH_3$ | 5-(3-Cl—Ph) | H | $CH_2$ | H | 3.16 |
| I-2-a-34 | H | Cl | 5-(3-Cl—Ph) | H | $CH_2$ | H | 3.11 |
| I-2-a-35 | H | $CH_3$ | H | 5-$CH_3$ | $CH_2$ | H | 2.15 |
| I-2-a-36 | H | Br | 4-Cl | H | $CH_2$ | H | 2.25 |
| I-2-a-37 | H | Cl | 4-Br | H | $CH_2$ | H | 2.31 |
| I-2-a-38 | H | Cl | H | H | $CH_2$ | H | 1.86 |
| I-2-a-39 | H | Cl | 4-Cl | H | $CH_2$ | H | 2.21 |
| I-2-a-40 | H | Cl | 4-Br | 5-Cl | $CH_2$ | H | 2.53 |
| I-2-a-41 | $CH_3$ | $CH_3$ | 4-$CH_3$ | 3-Br | $CH_2$ | H | 2.70 |
| I-2-a-42 | $CH_3$ | $CH_3$ | 5-(4-Cl—Ph) | H | $CH_2$ | H | 3.29 |
| I-2-a-43 | H | $CH_3$ | 4-Cl | 5-$CH_3$ | $CH_2$ | H | 2.47 |
| I-2-a-44 | H | Br | 4-$CH_3$ | 5-F | $CH_2$ | H | 2.25 |
| I-2-a-45 | H | $CH_3$ | 4-$CH_3$ | 5-F | $CH_2$ | H | 2.25 |
| I-2-a-46 | $CH_3$ | $CH_3$ | H | 3-Cl | $CH_2$ | H | 2.42 |
| I-2-a-47 | $CH_3$ | Br | 4-Br | 3-$CH_3$ | $CH_2$ | H | 2.78 |
| I-2-a-48 | H | Cl | 4-$CH_3$ | 5-Cl | $CH_2$ | H | 2.47 |
| I-2-a-49 | H | Br | H | 5-$CH_3$ | $CH_2$ | H | 2.16 |
| I-2-a-50 | H | $CH_3$ | 4-$OCH_3$ | H | $CH_2$ | H | 2.21 |
| I-2-a-51 | H | Br | H | 5-Br | $CH_2$ | H | 2.27 |
| I-2-a-52 | Cl | Cl | H | 3-$CH_3$ | $CH_2$ | H | 2.23 |
| I-2-a-53 | Cl | Cl | 4-Br | 3-$CH_3$ | $CH_2$ | H | 2.70 |
| I-2-a-54 | $CH_3$ | $CH_3$ | 4-$CH_3$ | 3-F | $CH_2$ | H | 2.45 |
| I-2-a-55 | $C_2H_5$ | $C_2H_5$ | 4-Br | H | $CH_2$ | $C_3H_7$ | 4.24 |
| I-2-a-56 | H | Cl | 4-$CH_3$ | H | $CH_2$ | $C_3H_7$ | 3.32 |
| I-2-a-57 | H | $CH_3$ | H | H | $CH_2$ | $C_3H_7$ | 3.03 |
| I-2-a-58 | H | $CH_3$ | 4-$CH_3$ | H | $CH_2$ | $C_3H_7$ | 3.32 |
| I-2-a-59 | H | Br | 4-$CH_3$ | 5-$CH_3$ | $CH_2$ | $C_3H_7$ | 3.57 |
| I-2-a-60 | $CH_3$ | Cl | 4-$CH_3$ | H | $CH_2$ | $C_3H_7$ | 3.49 |
| I-2-a-61 | $CH_3$ | $CH_3$ | 4-$CH_3$ | 3-$CH_3$ | $CH_2$ | $C_3H_7$ | 3.76 |
| I-2-a-62 | H | $CH_3$ | H | 5-$CH_3$ | $CH_2$ | $C_3H_7$ | 3.36 |
| I-2-a-63 | $CH_3$ | $C_2H_5$ | 4-Br | H | $CH_2$ | $C_3H_7$ | 3.99 |
| I-2-a-1 | $CH_3$ | $CH_3$ | 4-$CH_3$ | H | $CH_2$ | $C_3H_7$ | 3.57 |

The Compounds of the formula (I-2-a) are generally obtained as isomer mixtures and, in the cases marked [1], were separated by column chromatography into the cis and trans diastereomers.

Ph = 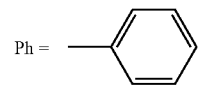

Example (I-2-b-1)

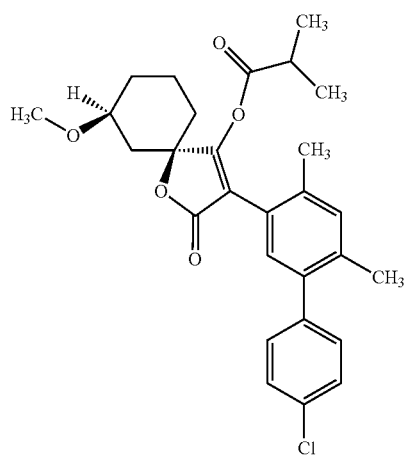

0.20 g (0.48 mmol) of the compound of Example I-2-a-32 (cis isomer) and 0.06 g (0.58 mmol) of triethylamine are initially charged in 20 ml of dichloromethane, 0.58 ml (0.58 mmol) of a 1M solution of isobutyryl chloride in tetrahydrofuran is added dropwise and the mixture is stirred at room temperature for 12 h.

For work-up, the mixture is washed with 10% strength citric acid, 10% strength aqueous sodium hydroxide solution and water, dried and concentrated using a rotary evaporator.

Purification is carried out by column chromatography (silica gel, dichloromethane/acetone 95:5).

Yield: 0.23 g (98% of theory)
log P 5.37
$^1$H-NMR (400 MHz, CD$_3$CN): δ=1.02 (d, 6H, CH(CH$_3$)$_2$), 3.31 (s, 3H, OCH$_3$), 3.50

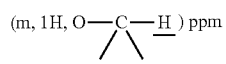

(m, 1H, O—C—H) ppm

Analogously to Example (I-2-b-1) and in accordance with the general statements on the preparation, the following compounds of the formula (I-2-b) are obtained

Example (I-2-c-1)

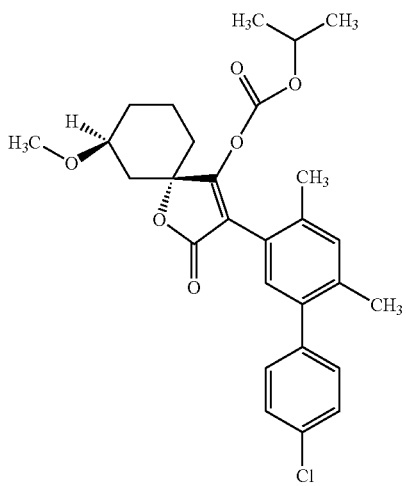

0.20 g (0.48 mmol) of the compound of Example I-2-a-32 (trans isomer) and 0.06 g (0.58 mmol) of triethylamine are initially charged in 20 ml of dichloromethane, 0.58 mol (0.58 mmol) of a 1M solution of isobutyryl chloride in tetrahydrofuran is added and the mixture is stirred at room temperature for 12 h.

For work-up, the mixture is washed with 10% strength citric acid, 10% strength aqueous sodium hydroxide solution and water, dried and concentrated using a rotary evaporator.

(I-2-b)

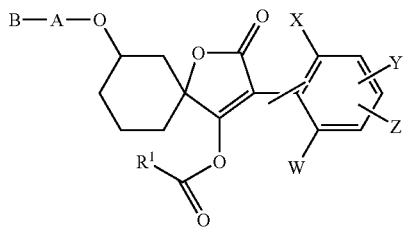

| Ex. No. | W | X | Y | Z | A | B | R$^1$ | logP | Isomer |
|---|---|---|---|---|---|---|---|---|---|
| I-2-b-2 | H | CH$_3$ | 5-(4-Cl—Ph) | 4-CH$_3$ | CH$_2$ | H | i-C$_3$H$_7$ | 5.25 | trans |
| I-2-b-3 | CH$_3$ | CH$_3$ | 4-CH$_3$ | H | CH$_2$ | H | i-C$_3$H$_7$ | 4.32 | cis |
| I-2-b-4 | CH$_3$ | CH$_3$ | 4-CH$_3$ | H | CH$_2$ | H | i-C$_3$H$_7$ | 4.15 | trans |
| I-2-b-5 | CH$_3$ | OCH$_3$ | 4-CH$_3$ | H | CH$_2$ | H | i-C$_3$H$_7$ | 3.90 | cis |
| I-2-b-6 | CH$_3$ | OCH$_3$ | 4-CH$_3$ | H | CH$_2$ | H | i-C$_3$H$_7$ | 3.75 | trans |
| I-2-b-7 | H | CH$_3$ | 4-Cl | H | CH$_2$ | H | i-C$_3$H$_7$ | 4.19, 3.98 | α + β about 1:1 |
| I-2-b-8 | CH$_3$ | Cl | 4-Cl | H | CH$_2$ | H | i-C$_3$H$_7$ | 4.49, 4.34 | α + β about 1:1 |

Ph = 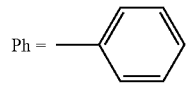

Further purification is carried out by column chromatography (silica gel, dichloromethane/acetone 95:5).

Yield: 0.20 g (75% of theory)

log P 5.21

$^1$H-NMR (400 MHz, CD$_3$CN): δ=1.04 (d, 6H, CH(CH$_3$)$_2$), 3.28 (s, 3H, OCH$_3$), 3.51

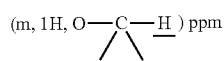 (m, 1H, O—C—H) ppm

Analogously to Example (I-2-c-1) and in accordance with the general statements on the preparation, the following compounds of the formula (I-2-c) are obtained

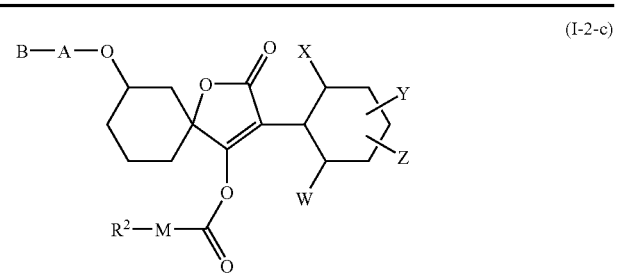

(I-2-c)

| Ex. No. | W | X | Y | Z | A | B | M | R² | logP | Isomer |
|---|---|---|---|---|---|---|---|---|---|---|
| I-2-c-2 | H | CH$_3$ | 5-(4-Cl—Ph) | 4-CH$_3$ | CH$_2$ | H | O | i-C$_3$H$_7$ | 5.32 | cis |
| I-2-c-3 | CH$_3$ | CH$_3$ | 4-CH$_3$ | H | CH$_2$ | H | O | i-C$_3$H$_7$ | 4.17 | trans |
| I-2-c-4 | CH$_3$ | CH$_3$ | 4-CH$_3$ | H | CH$_2$ | H | O | i-C$_3$H$_7$ | 4.34 | cis |
| I-2-c-5 | CH$_3$ | OCH$_3$ | 4-CH$_3$ | H | CH$_2$ | H | O | i-C$_3$H$_7$ | 3.75 | trans |
| I-2-c-6 | CH$_3$ | OCH$_3$ | 4-CH$_3$ | H | CH$_2$ | H | O | i-C$_3$H$_7$ | 3.90 | cis |

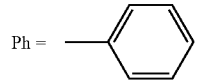

Process (J)

Synthesis of 7-alkoxy-1,3-diazaspiro-[4,5]-decane-2,4-diones of the formula (XXI) as precursors of 1-amino-3-alkoxycydohexanecarboyxlic acids of the formula (XVII)

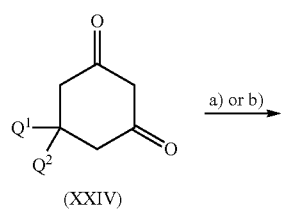

(XXIV)

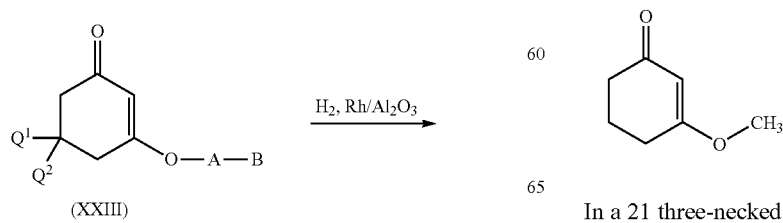

(XXII)

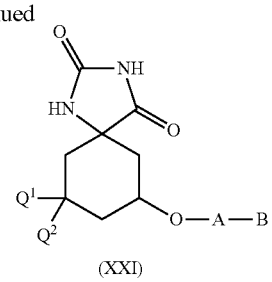

(XXI)

Preparation of 3-methoxycyclohex-2-enone (XXIII-1) variant a)

In a 2l three-necked flask, 100 g (0.89 mol) of cyclohexane-1,3-dione are initially charged and dissolved in 300 ml of methanol, 1000 ml of toluene and 97.6 ml of trimethyl orthoformate, 5 g of p-toluenesulphonic acid dihydrate are added and the mixture is heated under reflux for 2 h. After cooling, the mixture is washed 4× with in each case 200 ml of 10% strength NaOH and the organic phase is dried over sodium sulphate and concentrated on a rotary evaporator. This gives 73.4 g of a light-brown oil which is used for the next step without further purification.

Preparation of 3-propoxycyclohex-2-enone (XXIII-2 (variant b)

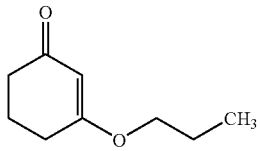

In a 2l three-necked flask, 100 g (0.89 mol) of cyclohexane-1,3-dione are initially charged and dissolved in 166.6 ml (2.23 mol) of n-propane and 600 ml of toluene and 97.6 ml (892 mmol) of trimethyl orthoformate, 5 g of p-toluenesulphonic acid dihydrate are added and the mixture is stirred under reflux on a water separator for 5 h until no more water separates off. The solution is then concentrated under reduced pressure on a rotary evaporator and the residue is taken up in 400 ml of MTBE and washed three times with 100 ml of 10% strength NaOH and saturated NaCl solution. The organic phase is dried over sodium sulphate and concentrated using a rotary evaporator. This gives 124.8 g yield of a yellow oil which is used for the next step without further purification.

Analogously to Examples (XXIII-1) and (XXIII-2) and in accordance with the other processes described in the literature, the following compounds of the formula (XXIII) are obtained (XXIII)

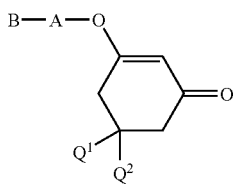

| Ex. No. | A | B | $Q^1$ | $Q^2$ |
|---|---|---|---|---|
| XXIII-3 | $CH_2$ | $CH_3$ | H | H |
| XXIII-4 | $CH_2$ | $C_3H_7$ | H | H |
| XXIII-5 | $CH_2$ | H | $CH_3$ | $CH_3$ |
| XXIII-6 | $CH_2$ | i-$C_3H_7$ | $CH_3$ | $CH_3$ |
| XXIII-7 | $CH_2$ | △ | H | H |
| XXIII-8 | $CH_2$ | (tetrahydrofuranyl) | H | H |

Example XXII-1

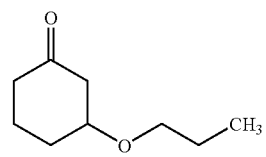

122 g (0.791 mmol) of 3-propoxycyclohex-2-enone (XXIII-2) are dissolved in 1200 ml of ethyl acetate, 12.2 g of Rh/Al$_2$O$_3$ (5% Rh) are added and the mixture is hydrogenated in an autoclave at room temperature and under a hydrogen pressure of 6.5 bar for 9 h. The catalyst is filtered off and washed with ethyl acetate, and the solution is concentrated on a rotary evaporator. The resulting brown oil is distilled under high vacuum. This gives 2 fractions of 47 g (99% pure) and 47.7 g (78% pure; contains 21% of 3-propoxycyclohexan-1-ol as only impurity), respectively, which corresponds to a total yield of 68%.

Analogously to Example (XXII-1) and in accordance with the statements, known from the literature, on the hydrogenation of compounds of the formula (XXIII), the following compounds of the formula (XXII) are obtained.

(XXII)

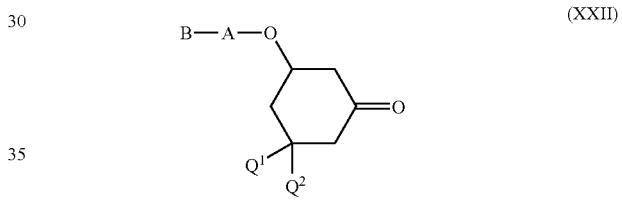

| Ex. No. | A | B | $Q^1$ | $Q^2$ |
|---|---|---|---|---|
| XXII-2 | $CH_2$ | H | H | H |
| XXII-3 | $CH_2$ | $CH_3$ | H | H |
| XXII-4 | $CH_2$ | $C_3H_7$ | H | H |
| XXII-5 | $CH_2$ | H | $CH_3$ | $CH_3$ |
| XXII-6 | $CH_2$ | i-$C_3H_7$ | $CH_3$ | $CH_3$ |
| XXII-7 | $CH_2$ | △ | H | H |
| XXII-8 | $CH_2$ | (tetrahydrofuranyl) | H | H |

Example XXI-1

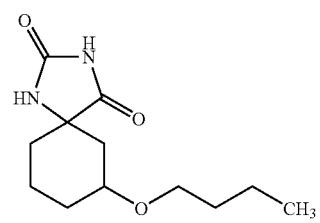 [SMILES: CCCCOC1CCCC2(C1)NC(=O)NC2=O]

18.4 g (1.1 eq.) of NaCN and 154.2 g (4.7 eq.) of ammonium carbonate are initially charged in 612 ml of water. At room temperature, 61.2 g (1 eq.) of the compound of Example (XXII-4) dissolved in 612 ml of ethanol, are slowly added dropwise. After 16 h at 55-60° C., the mixture is cooled to room temperature and, on a rotary evaporator, concentrated to dryness.

The solid is triturated in 300 ml of ethanol for 30 min, the solution is decanted and the solid is again triturated. The combined ethanol phases are dried over $MgSO_4$ and filtered through a nutsch filter, and the filtrate is concentrated using a rotary evaporator.

Yield: 61.4 g (88% of theory)

$^1$H-NMR (400 MHz, DMSO): 7.70 (bs, 1H); 6.66 (bs, 1H); 3.70-3.76 (m, 0.5H); 3.31-3.43 (m, 2.5H); 1.91-1.99 (m, 0.5H); 1.82-1.88 (m, 0.5H); 1,26-1.75 (bm, 11H); 0.86-0.92 (m, 3H)

Analogously to Example (XXI-1) and in accordance with the preparation processes described in the literature (for example L. Munday, J. Chem. Soc. 4372 (1961)), the following compounds of the formula (XXI) are obtained The log P values given in the tables and preparation examples above are determined in accordance with EEC-Directive 79/831 Annex V.A8 by HPLC (High Performance Liquid Chromatography) on a reverse-phase column (C 18). Temperature: 43° C.

The determination is carried out in the acidic range at pH 2.3 using the mobile phases 0.1% aqueous phosphoric acid and acetonitrile; linear gradient from 10% acetonitrile to 95% acetonitrile.

The LC-MS determination in the acidic range is carried out at pH 2.7 using the mobile phases 0.1% aqueous formic acid and acetonitrile (contains 0.1% formic acid); linear gradient from 100% acetonitrile to 95% acetonitrile.

The LC-MS determination in the neutral range is carried out at pH 7.8 using the mobile phases 0.001 molar aqueous ammonium bicarbonate solution and acetonitrile; linear gradient from 10% acetonitrile to 95% acetonitrile.

The calibration is carried out using unbranched alkan-2-ones (with 3 to 16 carbon atoms) with known log P values

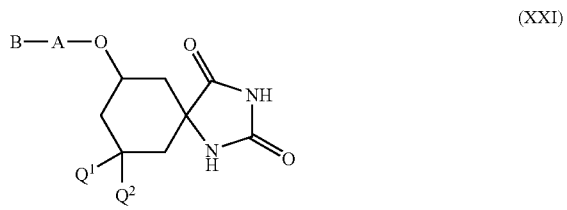

(XXI)

| Ex. No. | A | B | $Q^1$ | $Q^2$ | $^1$H-NMR (400 MHz, DMSO): shift δ in ppm |
|---|---|---|---|---|---|
| XXI-2 | $CH_2$ | H | H | H | 7.67 (bs, 1H); 6.80 (bs, 1H); 3.59-3.66 (m, 0.5H); 3.25-3.35 (m, 0.5H) 3.22 (s, 1.5H); 3.18 (s, 1.5H); 1.95-2.01 (m, 0.5H); 1.80-1.87 (dd, 0.5H); 1.27-1.75 (bm, 7H) |
| XXI-3 | $CH_2$ | $CH_3$ | H | H | 7.97 (bs, 1H); 7.06 (bs, 1H); 3.70-3.76 (m, 0.5H); 3.34-3.45 (bm, 2.5H); 1.91-1.98 (m, 0.5H); 1.82-1.89 (dd, 0.5H); 1.58-1.77 (bm, 3H); 1.32-1.58 (bm, 4H); 1.02-1.12 (m, 3H) |
| XXI-4 | $CH_2$ | $C_3H_7$ | H | H | 7.98 (bs, 1H); 6.98 (bs, 1H); 3.70-3.76 (m, 0.5H); 3.3-3.43 (m, 2.5H); 1.92-2.00 (m, 0.5H); 1.85-1.91 (dd, 0.5H); 1.58-1.80 (bm, 3H); 1.35-1.56 (bm, 6H); 0.82-0.9 (m, 3H) |
| XXI-5 | $CH_2$ | H | $CH_3$ | $CH_3$ | 0.9, 0.99 (2s, 6H, 2 × $CH_3$); 3.21 (s, 3H, $OCH_3$) |
| XXI-6 | $CH_2$ | i-$C_3H_7$ | $CH_3$ | $CH_3$ | 0.82, (d, 6H, $CH(CH_3)_2$); 0.90, 0.99 (2s, 6H, 2 × $CH_3$) |
| XXI-7 | $CH_2$ | △ | H | H | 0.01. 0.30 (2m, 4 H, —<$CH_2$|$CH_2$); 3.08 (m, 2 H, —O—$CH_2$—◁); 3.32, 3.62 (2m, 1 H, CH—O) |
| XXI-8 | $CH_2$ | (tetrahydrofuranylmethyl) | H | H | 2.30-2.90 (several multiplets, 12H, $CH_2$); 3.30-4.0 (several multiplets, 6H, 2 × O—CH, 2 × $OCH_2$); 8.26 (bs, 1H, NH) |

(determination of the log P values by retention times using linear interpolation between two successive alkanones).

The lambda max values were determined in the maxima of the chromatographic signals using the UV spectra from 200 nm to 400 nm.

Example A

Myzus Test (Spray Treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with a preparation of active compound of the desired concentration.

After the desired period of time, the effect in % is determined. 100% means that all aphids have been killed; 0% means that none of the aphids have been killed.

In this test, the compounds of Preparation Examples I-1-a-1, I-1-a-2, I-1-a-6, I-1-a-7, I-1-a-8, I-1-a-9, I-1-a-10, I-1-a-12, I-1-a-14, I-1-a-15, I-1-a-16, I-1-a-17, I-1-a-18, I-1-a- 19, I-1-a-20, I-1-a-21, I-1-a-22, I- 1-a-24, I- 1-a-25, I-1-a-26, I-1-a-27, I-1-a-28, I-1-a-29, I-1-a-30, I-1-a-32, I-1-a-35, I-1-a-36, I-1-a-40, I-1-a-51, I-1-a-52, I-2-a-1, I-2-a-2, I-2-a-4, I-2-a-5, I-2-a-6, I-2-a-7, I-2-a-8, I-2-a-9, I-2-a-10, I-2-a-11, I-2-a-12, I-2-a-13, I-2-a-14, I-2-a-15, I-2-a-16, I-2-a-18, I-2-a-20, I-2-a-21, I-2-a-22, I-2-a-26, I-2-a-27, I-2-a-28, I-2-a-29, I-2-a-31, I-2-a-32, I-2-a-33, I-2-a-34, I-2-a-35, I-2-a-36, I-2-a-37, I-2-a-39, I-2-a-42, I-2-a-45, I-2-a-46, I-2-a-47, I-2-a-49, I-2-a-50, I-2-a-52, I-2-a-54, I-2-b-1, I-2-b-2, I-2-b-3, I-2-b-4, I-2-b-5, I-2-b-6, I-1-c-2, I-2-c-3, I-2-c-1, I-2-c-2, I-2-c-3, I-2-c-4, I-2-c-5 and I-2-c-6 exhibit, at active compound concentrations of 500 g/ha, a kill rate against Myzus persicae of ≧90%.

Example B

Phaedon Test (Spray Treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after drying, are populated with larvae of the mustard beetle (*Phaedon cochleariae*).

After the desired period of time, the effect in % is determined. 100% means that all beetle larvae have been killed; 0% means that none of the beetle larvae have been killed.

In this test, the compounds of Preparation Examples I-1-a-1, I-1-a-2, I-1-b-1, I-1-a-5, I-1-a-6, I-1-a-8, I-1-a-14, I-1-a-15, I-1-a-17, I-1-a-19, I-1-a-20, I-1-a-21, I-1-a-22, I-1-a-24, I-1-a-26, I-1-a-28, I-1-a-29, I-1-a-30, I-1-a-31, I-1-a-36, I-1-a-38, I-1-a-44, I-1-a-46, I-1-a-51, I-2-a-1, I-2-a-2, I-2-a-12, I-2-a-14, I-2-a-16, I-2-a-17, I-2-a-31, I-2-a-33, I-2-a-42 and I-2-b-1 exhibit, at active compound concentrations of 500 g/ha, a kill rate against Phaedon cochleariae of ≧90%.

Example C

*Spodoptera frugiperda* Test (Spray Treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with a preparation of active compound of the desired concentration and, after drying, populated with caterpillars of the army worm (*Spodoptera frugiperda*).

After the desired period of time, the effect in % is determined. 100% means that all caterpillars have been killed; 0% means that none of the caterpillars have been killed.

In this test, the compounds of Preparation Examples I-1-c-3, I-1-a-6, I-1-a-36, I-2-a-8, I-2-a-11, I-2-a-14, I-2-a-31, I-2-a-32, I-2-b-3 and I-2-c-4 exhibit, at active compound concentrations of 500 g/ha, a kill rate against Spodoptera frugiperda of ≧80%.

Example D

*Tetranychus* Test (OP-Resistant/Spray Treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are heavily infested by all stages of the greenhouse red spider mite (*Tetranychus urticae*) are sprayed with a preparation of active compound of the desired concentration.

After the desired period of time, the effect in % is determined. 100% means that all spider mites have been killed; 0% means that none of the spider mites have been killed.

In this test, the compounds of Preparation Examples I-1-a-1, I-1-a-6, I-1-a-7, I-1-a-10, I-1-a-14, I-1-a-15, I-1-a-18, I-1-a-26, I-1-a-28, I-1-a-29, I-1-a-30, I-1-a-32, I-1-a-33, I-1-a-35, I-1-a-36, I-1-a-40, I-1-a-42, I-1-a-45, I-1-a-46, I-1-a-51, I-1-a-52, I-2-a-1, I-2-a-2, I-2-a-16, I-2-a-42, I-2-b-1, I-2-b-3, I-2-b-4, I-2-b-5, I-2-b-6, I-2-c-1, I-2-c-2, I-2-c-3, I-2-c-4, I-2-c-5, I-2-c-6, I-1-c-2, I-1-c-1, I-1-c-3, I-1-a-5 and I-1-a-4 exhibit, at active compound concentrations of 100 g/ha, a kill rate against Tetranychus urticae of ≧70%.

Example E

Critical Concentration Test/Soil Insects—Treatment of Transgenic Plants

| Test insect: | *Diabrotica balteata* - larvae in the soil |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l) matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example F

*Heliothis* virescens test—treatment of transgenic plants

| Solvent: | 7 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration Soybean shoots (*Glycine max*) of the cultivar Roundup Ready (trade mark of Monsanto Comp., USA) are treated by being dipped into the preparation of active compound of the desired concentration and are populated with the tobacco budworm Heliothis virescens while the leaves are still moist.

After the desired period of time, the kill of the insects is determined.

Examples G

Herbicidal Pre-Emergence Action

Seeds of monocotyledonous and dicotyledonous weed and crop plants are placed into sandy loam in wood fibre pots and covered with soil. The test compounds, formulated in the form of wettable powders (WP) or emulsion concentrates (EC), are then, as an aqueous suspension with a water application rate of 800 l/ha (converted), with 0.2% of wetting agent added, applied to the surface of the covering soil.

After the treatment, the pots are placed in a greenhouse and kept under good growth conditions for the test plants. The visual assessment of the emergence damage on the test plants is carried out after a trial period of 3 weeks by comparison with untreated controls (herbicidal effect in per cent (%): 100% effect=the plants have died, 0% effect=like control plants).

Herbicidal Post-Emergence Action

Seeds of monocotyledonous and dicotyledonous weed and crop plants are placed into sandy loam in wood fibre pots, covered with soil and cultivated in a greenhouse under good growth conditions. 2-3 weeks after sowing, the test plants are treated at the one-leaf stage. The test compounds, formulated as wettable powders (WP) or emulsion concentrates (EC) are then, as an aqueous suspension with a water application rate of 800 l/ha (converted), with 0.2% of wetting agent added, sprayed onto the green parts of the plants. After the test plants were kept in the greenhouse under optimum growth conditions for about 3 weeks, the effect of the preparations is rated visually in comparison to untreated controls (herbicidal effect in per cent (%): 100% effect=the plants have died, 0% effect=like control plants).

At 320 g/ha of a.i., the following compounds, applied by the pre-emergence method, show an effect of ≧80% against Avena sativa, Lolium multiflorum and Setaria viridis:

I-1-a-12, I-1-a-17, I-1-a-36, I-1-a-63, I-1-a-71.

At 320 g/ha of a.i., the following compounds, applied by the post-emergence method, show an effect of ≧70% against Avena sativa, Lolium multiflorum and Setaria viridis and Echinochloa:

I-1-a-1, I-1-a-12, I-1-a-14, I-1-a-17, I-1-a-18, I-1-a-36, I-1-a-40, I-1-a-47, I-1-a-66, I-1-a-67, I-1-a-63, I-1-a-71, I-1-a-49, I-1-a-64, I-1-a-79, I-1-b-1, I-1-b-26, I-1-c-1, I-1-c-2, I-1-c-3, I-1-c-18, I-2-a-3, I-2-a-13.

Example H

Herbicidal Post-Emergence Action

Seeds of monocotyledonous and dicotyledonous weed and crop plants are placed into sandy loam in wood fibre pots or in plastic pots, covered with soil and cultivated in a greenhouse, during the vegetation period also outdoors outside of the greenhouse, under good growth conditions. 2-3 weeks after sowing, the test plants are treated at the one- to three-leaf stage. The test compounds, formulated as wettable powders (WP) or emulsifiable concentrates (EC) are, in various dosages with a water application rate of 300 l/ha (converted), with wetting agent (0.2 to 0.3%) added, sprayed onto the plants and the surface of the soil. 3-4 weeks after the treatment of the test plants, the effect of the preparations is rated visually in comparison to untreated controls (herbicidal effect in per cent (%): 100%=the plants have died, 0% effect=like control plants).

Use of Safeners

If it is additionally to be tested as to whether safeners can improve the crop plant compatibility of test substances in the case of crop plants, the following options are used for applying the safener:

- seeds of the crop plants are, before sowing, dressed with the safener substance (the amount of safener stated in per cent, based on the weight of the seed)
- before the application of the test substances, the crop plants are sprayed with the safener at a certain application rate per hectare (usually 1 day before the application of the test substances)
- the safener is applied together with the test substance as a tank mix (the amount of safener is stated in g/ha or as a ratio, based on the herbicide).

By comparing the effect of the test substances on crop plants without or with safener treatment, it is possible to assess the effect of the safener substance.

Container Trials with Cereal in a Greenhouse

Mefenpyr 1 Day Prior to Herbicide Application

TABLE

|  | Application rate g of a.i./ha | Summer wheat observed (%) |
|---|---|---|
| Ex. I-1-a-2 | 100 | 60 |
| Ex. I-1-a-2 + mefenpyr | 100 + 100 | 15 |

TABLE

|  | Application rate g of a.i./ha | Summer barley observed (%) | Summer wheat observed (%) |
|---|---|---|---|
| Ex. I-1-a-12 | 12.5 | 99 | 97 |
|  | 6.25 | 97 | 10 |
|  | 3.125 | 30 |  |
| Ex. I-1-a-12 + mefenpyr | 12.5 + 100 | 30 | 20 |
|  | 6.25 + 100 | 5 | 5 |
|  | 3.125 + 100 | 0 |  |

TABLE

|  | Application rate g of a.i./ha | Summer barley observed (%) | Summer wheat observed (%) |
|---|---|---|---|
| Ex. I-1-a-14 | 25 | 93 | 93 |
|  | 12.5 | 30 | 30 |
| Ex. I-1-a-14 + mefenpyr | 25 + 100 | 30 | 50 |
|  | 12.5 + 100 | 10 | 15 |

TABLE

|  | Application rate g of a.i./ha | Summer wheat observed (%) |
|---|---|---|
| Ex. I-1-a-17 | 25 | 70 |
|  | 12.5 | 60 |
|  | 6.25 | 10 |
| Ex. I-1-a-17 + mefenpyr | 25 + 100 | 30 |
|  | 12.5 + 100 | 10 |
|  | 6.25 + 100 | 0 |

TABLE

|  | Application rate g of a.i./ha | Summer barley observed (%) | Summer wheat observed (%) |
|---|---|---|---|
| Ex. I-1-a-18 | 12.5 | 93 | 95 |
|  | 6.25 | 50 | 40 |
|  | 3.125 |  | 30 |
| Ex. I-1-a-18 + mefenpyr | 12.5 + 100 | 40 | 40 |
|  | 6.25 + 100 | 5 | 5 |
|  | 3.125 + 100 |  | 0 |

TABLE

|  | Application rate g of a.i./ha | Summer barley observed (%) |
|---|---|---|
| Ex. I-1-a-19 | 100 | 30 |
|  | 50 | 25 |
| Ex. I-1-a-19 + mefenpyr | 100 + 100 | 10 |
|  | 50 + 100 | 0 |

TABLE

|  | Application rate g of a.i./ha | Summer barley observed (%) | Summer wheat observed (%) |
|---|---|---|---|
| Ex. I-1-b-8 | 50 | 70 | 50 |
|  | 25 | 30 | 30 |
| Ex. I-1-b-8 + mefenpyr | 50 + 100 | 20 | 20 |
|  | 25 + 100 | 10 | 10 |

TABLE

|  | Application rate g of a.i./ha | Summer barley observed (%) | Summer wheat observed (%) |
|---|---|---|---|
| Ex. I-1-b-9 | 50 | 90 | 90 |
|  | 25 | 30 | 20 |
| Ex. I-1-b-9 + mefenpyr | 50 + 100 | 20 | 10 |
|  | 25 + 100 | 10 | 0 |

TABLE

|  | Application rate g of a.i./ha | Summer wheat observed (%) |
|---|---|---|
| Ex. I-1-c-9 | 100 | 60 |
|  | 50 | 30 |
| Ex. I-1-c-9 + mefenpyr | 100 + 100 | 20 |
|  | 50 + 100 | 10 |

TABLE

|  | Application rate g of a.i./ha | Summer wheat observed (%) |
|---|---|---|
| Ex. I-1-c-10 | 12.5 | 60 |
| Ex. I-1-c-10 + mefenpyr | 12.5 + 100 | 10 |

TABLE

|  | Application rate g of a.i./ha | Summer wheat observed (%) |
|---|---|---|
| Ex. I-1-b-11 | 50 | 70 |
|  | 25 | 10 |
| Ex. I-1-b-11 + mefenpyr | 50 + 100 | 10 |
|  | 25 + 100 | 5 |

TABLE

|  | Application rate g of a.i./ha | Summer wheat observed (%) |
|---|---|---|
| Ex. I-1-b-14 | 6.25 | 30 |
|  | 3.125 | 20 |
| Ex. I-1-b-14 + mefenpyr | 6.25 + 100 | 0 |
|  | 3.125 + 100 | 0 |

Container Trials with Maize in a Greenhouse

Isoxadifen 1 Day Prior to the Herbicide Application

| | Application rate g of a.i./ha | Cecilia Mais observed (%) |
|---|---|---|
| Ex. I-1-c-10 | 12.5 | 40 |
| Ex. I-1-c-10 + isoxadifen | 12.5 + 100 | 15 |

Container Trials with Cereals Outdoors

Mefenpyr 1 Day Prior to the Herbicide Application

| | Application rate g of a.i./ha | Summer barley observed (%) | Summer wheat observed (%) |
|---|---|---|---|
| Ex. I-1-a-43 | 25 | 70 | 60 |
| | 12.5 | 10 | 30 |
| Ex. I-1-a-43 + mefenpyr | 25 + 100 | 5 | 0 |
| | 12.5 + 100 | 0 | 0 |

| | Application rate g of a.i./ha | Summer barley observed (%) | Summer wheat observed (%) |
|---|---|---|---|
| Ex. I-1-a-43 | 100 | 30 | 30 |
| | 50 | 20 | 15 |
| Ex. I-1-a-43 + mefenpyr | 100 + 100 | 0 | 0 |
| | 50 + 100 | 0 | 0 |

Container Trials with Cereals Outdoors

Mefenpyr in Tank Mix 50 g/ha

| | Application rate g of a.i./ha | Summer barley observed (%) | Summer wheat observed (%) |
|---|---|---|---|
| Ex. I-1-a-1 | 100 | 70 | 35 |
| Ex. I-1-a-1 + mefenpyr | 100 + 50 | 20 | 15 |

| | Application rate g of a.i./ha | Summer barley observed (%) | Summer wheat observed (%) |
|---|---|---|---|
| Ex. I-1-a-43 | 100 | 60 | 60 |
| | 50 | 50 | 50 |
| | 25 | 40 | 40 |
| Ex. I-1-a-43 + mefenpyr | 100 + 50 | 25 | 10 |
| | 50 + 50 | 25 | 5 |
| | 25 + 50 | 5 | 0 |

Method: Tank Mix Post-Emergence

| | Application rate g of a.i./ha | Summer barley (Baronesse) observed (%) | Winter barley observed (%) |
|---|---|---|---|
| Ex. I-1-a-43 | 80 | 30 | 30 |
| Ex. I-1-a-43 + cloquintocet | 80 + 100 | 0 | 5 |

| | Application rate g of a.i./ha | Summer barley (Scarlett) observed (%) | Winter barley observed (%) |
|---|---|---|---|
| Ex. I-1-a-43 | 20 | 30 | 20 |
| Ex. I-1-a-43 + isoxadifen | 20 + 100 | 10 | 10 |

The invention claimed is:

1. A compound of formula (I)

$$\text{(I)}$$

in which
W represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano,
X represents halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano,
Y in the 4-position represents hydrogen, halogen, $C_1$-$C_6$-alkoxy, cyano, $C_1$-$C_4$-haloalkyl or $C_1$-$C_4$-haloalkoxy,
Z represents hydrogen, or
W represents hydrogen, halogen or $C_1$-$C_6$-alkyl,
X represents halogen, $C_1$-$C_6$-alkyl, $C_1$-$C_6$-alkoxy, $C_1$-$C_4$-haloalkyl, $C_1$-$C_4$-haloalkoxy or cyano,
Y in the 4-position represents $V^1$- and $V^2$-substituted phenyl or pyridyl,
Z represents hydrogen,
$V^1$ represents halogen, $C_1$-$C_{12}$-alkyl, $C_1$-$C_6$-alkoxy, $C_1$-$C_4$-haloalkyl or $C_1$-$C_4$-haloalkoxy,
$V^2$ represents hydrogen, halogen, $C_1$-$C_6$-alkyl, $C_1$-$C_6$-alkoxy or $C_1$-$C_4$-haloalkyl, or
$V^1$ and $V^2$ together represent $C_3$-$C_4$-alkanediyl which is optionally substituted by halogen and/or $C_1$-$C_2$-alkyl and which is optionally interrupted by one or two oxygen atoms, or
W represents hydrogen, halogen or $C_1$-$C_6$-alkyl,
X represents halogen, $C_1$-$C_6$-alkyl, $C_1$-$C_6$-alkoxy, $C_1$-$C_4$-haloalkyl, $C_{1-4}$ haloalkoxy or cyano, Y in the 5-position represents $V^1$- and $V^2$-substituted phenyl or pyridyl, Z in the 4-position represents hydrogen, $C_1$-$C_6$-alkyl, or halogen, $V^1$ represents halogen, $C_1$-$C_{12}$-alkyl, $C_1$-$C_6$-alkoxy, $C_1$-$C_4$-haloalkyl or $C_1$-$C_4$-aloalkoxy, $V^2$ represents hydrogen, halogen, $C_1$-$C_6$-alkyl, $C_1$-$C_6$-alkoxy or $C_1$-$C_4$-haloalkyl, or $V^1$ and $V^2$ together represent $C_3$-$C_4$-alkanediyl which is optionally substituted by halogen and/or $C_1$-$C_2$-alkyl and which is optionally interrupted by one or two oxygen atoms, or W represents hydrogen, $C_1$-$C_6$-alkyl, $C_2$-$C_6$-alkenyl, $C_2$-$C_6$-alkynyl, $C_1$-$C_6$-alkoxy, halogen, trifluoromethyl or cyano, X represents halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y in the 4-position represents $C_1$-$C_6$-alkyl, Z represents hydrogen, or W represents hydrogen, halogen, $C_1$-$C_6$-alkyl or $C_1$-$C_6$-alkoxy, X represents halogen, $C_1$-$C_6$-alkyl, $C_1$-$C_6$-alkoxy, $C_1$-$C_4$-haloalkyl, $C_1$-$C_4$-haloalkoxy or cyano, Y in the 4-position represents hydrogen, halogen, $C_1$-$C_6$-alkyl, $C_1$-$C_4$-haloalkyl or $C_1$-$C_4$-haloalkoxy, Z in the 3- or 5-position represents halogen, $C_1$-$C_6$-alkyl, $C_1$-$C_4$-haloalkyl, cyano, $C_1$-$C_6$-alkoxy or $C_1$-$C_4$-haloalkoxy, A represents optionally $C_1$-$C_4$-alkyl-substituted $C_1$-$C_4$-alkanediyl or optionally $C_1$-$C_4$-alkyl-substituted $C_1$-$C_4$-alkanediyl or optonally $C_1$-$C_4$-alkyl-substituted $C_5$-$C_8$-cycloalkyl in which optionally one methylene group is replaced by oxygen, B represents hydrogen; represents in each case optionally halogen-substituted $C_1$-$C_8$-alkyl, $C_2$-$C_8$-alkenyl, $C_1$-$C_6$-alkoxy, $C_1$-$C_6$-alkoxy-$C_1$-$C_4$-alkoxy, $C_1$-$C_4$-alkoxy-bis-$C_1$-$C_4$-alkoxy; represents optionally halogen-, $C_1$-$C_6$-alkyl-, $C_1$-$C_6$-alkoxy-, $C_1$-$C_4$-haloalkyl-, $C_1$-$C_4$-halo-alkoxy-, cyano- or nitro-substituted phenyl; represents optionally halogen-, $C_1$-$C_4$-alkyl- or $C_1$-$C_2$-haloalkyl-substituted pyridyl, pyrimidyl, thiazolyl or thienyl; or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which optionally one or two not directly adjacent methylene groups are replaced by oxygen, two methylene groups are replaced by the radical —O—CO— or three methylene groups are replaced by the radical —O—CO—O—, $Q^1$ represents hydrogen; represents in each case optionally halogen-substituted $C_1$-$C_6$-alkyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl; represents optionally halogen-, $C_1$-$C_4$-alkyl- or $C_1$-$C_4$-alkoxy-substituted $C_3$-$C_6$-cycloalkyl in which optionally one methylene group is replaced by oxygen; or represents phenyl, phenyl-$C_1$-$C_2$-alkyl or heteroaryl, each of which is optionally mono- or disubstituted by halogen, $C_1$-$C_4$-alkyl, $C_1$-$C_4$-alkoxy, $C_1$-$C_4$-haloalkyl or $C_1$-$C_4$-haloalkoxy, $Q^2$ represents hydrogen or $C_1$-$C_6$-alkyl, or $Q^1$ and $Q^2$ together with the carbon to which they are attached represent a $C_3$-$C_6$-ring which is optionally mono- or disubstituted by fluorine, chlorine, $C_1$-$C_4$-alkyl, $C_1$-$C_4$-alkoxy or trifluoromethyl and in which optionally one methylene group is replaced by oxygen, G represents hydrogen (a),

(b)

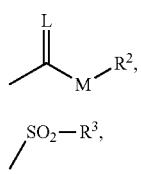
(c)

(d)

in which

L represents oxygen or sulphur,

M represents oxygen or sulphur, $R^1$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkyl-thio-$C_1$-$C_8$-alkyl or poly-$C_1$-$C_8$-alkoxy-$C_1$-$C_8$-alkyl; represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur;

represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl;

represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl;

represents optionally halogen- or $C_1$-$C_6$-alkyl-substituted 5- or 6-membered heteroaryl having one or two heteroatoms selected from the group consisting of oxygen, sulphur and nitrogen;

represents optionally halogen- or $C_1$-$C_6$-alkyl-substituted phenoxy-$C_1$-$C_6$-alkyl; or represents optionally halogen-, amino- or $C_1$-$C_6$-alkyl-substituted 5- or 6-membered heteroaryloxy-$C_1$-$C_6$-alkyl having one or two heteroatoms selected from the group consisting of oxygen, sulphur and nitrogen, $R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl;

represents optionally halogen-, $C_1$-$C_6$-alkyl- or $C_1$-$C_6$-alkoxy-substituted $C_3$-$C_8$-cycloalkyl; or represents in each case optionally halogen -, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, and $R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl.

2. A compound of formula (I) according to claim 1, in which

W represents hydrogen, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y in the 4-position represents hydrogen, fluorine, chlorine, bromine, methoxy, ethoxy, cyano, trifluoromethyl, difluoromethoxy or trifluoromethoxy, Z represents hydrogen, or W represents hydrogen, chlorine, bromine or $C_1$-$C_4$-alkyl, X represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y in the 4-position represents the radical

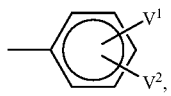

Z represents hydrogen, $V^1$ represents fluorine, chlorine, $C_1$-$C_4$-alkyl, $C_1$-$C_4$-alkoxy, $C_1$-$C_2$-haloalkyl or $C_1$-$C_2$-haloalkoxy,
$V^2$ represents hydrogen, fluorine, chlorine, $C_1$-$C_4$-alkyl, $C_1$-$C_4$-alkoxy or $C_1$-$C_2$-haloalkyl, or
$V^1$ and $V^2$ together represent —O—$CH_2$—O— or —O—$CF_2$—O—, or
W represents hydrogen, chlorine, bromine or $C_1$-$C_4$-alkyl,
X represents chlorine, bromine, $C_1$-$C_4$-alkyl or $C_1$-$C_2$-haloalkyl,
Y in the 5-position represents the radical

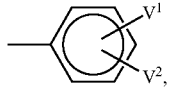

Z in the 4-position represents hydrogen, $C_1$-$C_4$-alkyl or chlorine,
$V^1$ represents fluorine, chlorine, $C_1$-$C_4$-alkyl, $C_1$-$C_4$-alkoxy, $C_1$-$C_2$-haloalkyl or $C_1$-$C_2$-haloalkoxy,
$V^2$ represents hydrogen, fluorine, chlorine, $C_1$-$C_4$-alkyl, $C_1$-$C_4$-alkoxy or $C_1$-$C_2$-haloalkyl, or
$V^1$ and $V^2$ together represent —O—$CH_2$—O— or —O—$CF_2$—O—, or
W represents hydrogen, $C_1$-$C_4$-alkyl, $C_2$-$C_4$-alkenyl, $C_2$-$C_4$-alkynyl, $C_1$-$C_4$-alkoxy, chlorine, bromine or trifluoromethyl,
X represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano,
Y in the 4-position represents $C_1$-$C_4$-alkyl,
Z represents hydrogen, or
W represents hydrogen, chlorine, bromine, $C_1$-$C_4$-alkyl or $C_1$-$C_4$-alkoxy,
X represents chlorine, bromine, $C_1$-$C_4$-alkyl, $C_1$-$C_4$-alkoxy, $C_1$-$C_2$-haloalkyl, $C_1$-$C_2$-haloalkoxy or cyano,
Y in the 4-position represents hydrogen, chlorine, bromine, $C_1$-$C_4$-alkyl, $C_1$-$C_2$-haloalkyl or $C_1$-$C_2$-haloalkoxy,
Z in the 3- or 5-position represents fluorine, chlorine, bromine, $C_1$-$C_4$-alkyl, $C_1$-$C_2$-haloalkyl, $C_1$-$C_4$-alkoxy or $C_1$-$C_2$-halo-alkoxy,
A represents an optionally $C_1$-$C_2$-alkyl-substituted $C_1$-$C_3$-alkanediyl group or represents $C_5$-$C_6$-cycloalkyl in which optionally one methylene group is replaced by oxygen,
B represents hydrogen, or represents $C_1$-$C_6$-alkyl, $C_2$-$C_6$-alkenyl, $C_1$-$C_4$-alkoxy, $C_1$-$C_4$-alkoxy-$C_1$-$C_3$-alkoxy, $C_1$-$C_4$-alkoxy-bis-$C_1$-$C_3$-alkoxy, each of which is optionally mono- to trisubstituted by fluorine or chlorine; represents phenyl which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro; represents pyridyl, pyrimidyl, thiazolyl or thienyl, each of which is optionally mono- or disubstituted by fluorine, chlorine, bromine, methyl, ethyl or trifluoromethyl; or represents $C_3$-$C_6$-cycloalkyl which is mono- or disubstituted by fluorine, chlorine, methyl, methoxy or trifluorom ethyl and in which optionally two not directly adjacent methylene groups are replaced by oxygen,
$Q^1$ represents hydrogen, $C_1$-$C_4$-alkyl, $C_1$-$C_4$-alkoxy, or $C_1$-$C_2$-alkoxy-$C_1$-$C_2$-alkyl, each of which is optionally mono- to trisubstituted by fluorine; or represents $C_3$-$C_6$-cycloalkyl which is optionally mono- or disubstituted by fluorine, chlorine, methyl, ethyl or methoxy and in which optionally one methylene group is replaced by oxygen,
$Q^2$ represents hydrogen or $C_1$-$C_4$-alkyl, or
$Q^1$ and $Q^2$ together with the carbon atom to which they are attached represent a $C_3$-$C_6$-ring which is optionally monosubstituted by fluorine, methyl, methoxy or trifluoromethyl and in which optionally one methylene group is replaced by oxygen,
G represents hydrogen (a), (b)

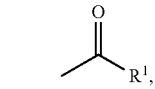

(c)

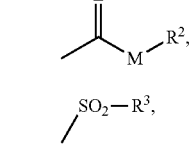

(d)

in which
L represents oxygen or sulphur and
M represents oxygen or sulphur,
$R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine; or represents $C_3$-$C_7$-cycloalkyl which is optionally mono- or disubstituted by fluorine, chlorine, $C_1$-$C_5$-alkyl, or $C_1$-$C_5$-alkoxy and in which optionally one or two not directly adjacent methylene groups are replaced by oxygen and/or sulphur;
represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl;
represents phenyl-$C_1$-$C_4$-alkyl, which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy;
represents pyrazolyl, thiazolyl, pyridyl, pyrimidyl, furanyl or thienyl, each of which is optionally mono- or disubstituted by fluorine, chlorine, bromine or $C_1$-$C_4$-alkyl;
represents phenoxy-$C_1$-$C_5$-alkyl which is optionally mono- or disubstituted by fluorine, chlorine, bromine or -$C_1$-$C_4$-alkyl; or
represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl,
$R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine;
represents $C_3$-$C_7$-cycloalkyl which is optionally mono- or disubstituted by fluorine, chlorine, $C_1$-$C_4$-alkyl or $C_1$-$C_4$-alkoxy; or
represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, and $R^3$ represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro.

3. A compound of formula (I) according to claim 1 in which
W represents hydrogen, methyl, chlorine, bromine, ethyl, methoxy, ethoxy or trifluoromethyl,
X represents chlorine, bromine, methyl, ethyl, propyl, methoxy, ethoxy, propoxy, methoxyethoxy, ethoxyethoxy, trifluoromethyl, difluoromethoxy, trifluoromethoxy or cyano,
Y in the 4-position represents hydrogen, chlorine, bromine, trifluorom ethyl or trifluoromethoxy
Z represents hydrogen, or
W represents hydrogen, chlorine, bromine, methyl or ethyl,
X represents chlorine, bromine, methyl, ethyl, propyl, methoxy, trifluoromethyl, difluoromethoxy or cyano,
Y in the 4-position represent the radical

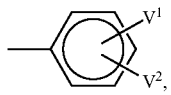

Z represents hydrogen,
$V^1$ represents fluorine, chlorine, methyl, methoxy, trifluorom ethyl or trifluoromethoxy,
$V^2$ represents hydrogen, fluorine, chlorine, methyl, methoxy or trifluoromethyl, or
W represents hydrogen, chlorine, or methyl,
X represents chlorine, methyl or trifluoromethyl,
Y in the 5-position represents the radical

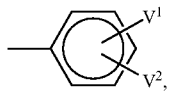

Z in the 4-position represents hydrogen or methyl,
$V^1$ represents fluorine, chlorine, methyl, methoxy, trifluorom ethyl or trifluoromethoxy,
$V^2$ represents hydrogen, fluorine, chlorine, methyl, methoxy or trifluoromethyl, or
W represents hydrogen, methyl, ethyl, methoxy, ethoxy, chlorine or bromine,
X represents chlorine, bromine, methyl, ethyl, propyl, methoxy, ethoxy, propoxy, methoxyethoxy, ethoxyethoxy, trifluoromethyl, difluoromethoxy, trifluoromethoxy or cyano,
Y in the 4-position represent methyl or ethyl,
Z represents hydrogen, or
W represents hydrogen, chlorine, bromine, methyl or ethyl,
X represents chlorine, bromine, methyl, ethyl, methoxy, trifluoromethyl, difluoromethoxy or trifluoromethoxy,
Y in the 4-position represents hydrogen, chlorine, bromine, methyl or ethyl,
Z in the 3- or 5-position represents fluorine, chlorine, bromine, methyl, ethyl, trifluoromethyl or trifluoromethoxy,
A represents —$CH_2$—, —$CHCH_3$—, —$CH_2$—$CH_2$—, —$CH_2$—$CHCH_3$—, —$CH_2$—$CH_2$—$CH_2$—,
B represents hydrogen, methyl, ethyl, propyl, isopropyl, butyl, isobutyl, $C_2$-$C_4$-alkenyl, methoxy, ethoxy, propoxy, isopropoxy, butoxy, isobutoxy, methoxyethoxy, ethoxyethoxy; represents phenyl which is optionally mono- or disubstituted by fluorine, chlorine, bromine, methyl, methoxy, trifluoromethyl, trifluoromethoxy, cyano or nitro; represents cyclopropyl; or represents cyclopentyl or cyclohexyl in which optionally one methylene group is replaced by oxygen,
$Q^1$ represents hydrogen, methyl, ethyl, propyl, isopropyl, cyclopropyl, cyclopentyl or cyclohexyl,
$Q^2$ represents hydrogen, methyl or ethyl, or
$Q^1$ and $Q^2$ together with the carbon atom to which they are attached represent cyclopropyl, cyclopentyl or cyclohexyl,
G represents hydrogen (a),

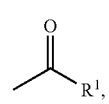 (b)

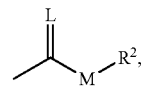 (c)

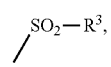 (d)

in which
L represents oxygen or sulphur and
M represents oxygen or sulphur,
$R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine; represents $C_3$-$C_6$-cycloalkyl which is optionally monosubstituted by fluorine, chlorine, methyl, ethyl or methoxy;
represents phenyl which is optionally mono- or disubstituted by fluorine, chlorine, bromine, cyano, nitro, methyl, ethyl, n-propyl, i-propyl, methoxy, ethoxy, trifluoromethyl or trifluoromethoxy; or
represents furanyl, thienyl or pyridyl, each of which is optionally monosubstituted by chlorine, bromine or methyl,
$R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine;
represents cyclopentyl or cyclohexyl;
or represents phenyl or benzyl, each of which is optionally mono- or disubstituted by fluorine, chlorine, cyano, nitro, methyl, ethyl, methoxy, trifluoromethyl or trifluoromethoxy, and
$R^3$ represents methyl, ethyl, propyl or isopropyl, each of which is optionally mono- to trisubstituted by fluorine or chlorine; or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro.

4. A compound of formula (I) according to claim 1 in which
W represents hydrogen, methyl, ethyl, chlorine or bromine,
X represents chlorine, bromine, methyl, ethyl, propyl, methoxy, ethoxy, propoxy, methoxyethoxy, cyclopropylmethyloxy, trifluoromethyl or difluoromethoxy,
Y in the 4-position represents hydrogen, chlorine, bromine, trifluoromethyl or trifluoromethoxy,
Z represents hydrogen,
A represents —$CH_2$—, —$CHCH_3$— or —$CH_2$—$CH_2$—,
B represents hydrogen, methyl, ethyl, propyl, isopropyl, $C_2$-$C_4$-alkenyl, methoxy, ethoxy, propoxy, isopropoxy, butoxy, isobutoxy; represents phenyl which is optionally mono- or disubstituted by fluorine, chlorine, bromine, methyl, methoxy, trifluoromethyl, trifluoromethoxy, cyano or nitro; or represents cyclopropyl, cyclopentyl or cyclohexyl, $Q^1$ represents hydrogen or methyl,
$Q^2$ represents hydrogen or methyl,
G represents hydrogen (a),

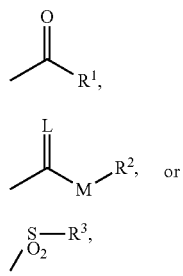

in which L represents oxygen and
M represents oxygen or sulphur,
$R^1$ represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine; represents cyclopropyl, cyclopentyl or cyclohexyl;
represents phenyl which is optionally monosubstituted by fluorine, chlorine, bromine, cyano, nitro, methyl, methoxy, trifluoromethyl or trifluoromethoxy; or
represents furanyl, thienyl or pyridyl, each of which is optionally monosubstituted by chlorine or methyl,
$R^2$ represents $C_1$-$C_8$-alkyl, $C_2$-$C_6$-alkenyl or $C_1$-$C_2$-alkoxy-$C_2$-$C_3$-alkyl;
represents cyclopentyl or cyclohexyl;
or represents phenyl or benzyl, each of which is optionally monosubstituted by fluorine, chlorine, cyano, nitro, methyl, methoxy, trifluoromethyl or trifluoromethoxy.
$R^3$ represents methyl-substituted phenyl.

5. A compound of formula (I) according to claim 1 in which
W represents hydrogen, chlorine, bromine, methyl or ethyl,
X represents chlorine, bromine, methyl, ethyl, propyl, methoxy, trifluoromethyl, difluoromethoxy or cyano,
Y in the 4-position represents the radical

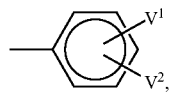

Z represents hydrogen,
$V^1$ represents fluorine, chlorine, methyl, methoxy, trifluoromethyl or trifluoromethoxy,
$V^2$ represents hydrogen, fluorine, chlorine, methyl, methoxy or trifluoromethyl,
A represents —$CH_2$—, —$CHCH_3$— or —$CH_2$—$CH_2$—,
B represents hydrogen, methyl, ethyl, propyl, isopropyl, $C_2$-$C_4$-alkenyl, methoxy, ethoxy, propoxy, isopropoxy, butoxy, or isobutoxy; or represents phenyl which is optionally mono- or disubstituted by fluorine, chlorine, bromine, methyl, methoxy, trifluoromethyl, trifluoromethoxy, cyano or nitro,
$Q^1$ represents hydrogen or methyl,
$Q^2$ represents hydrogen or methyl,
G represents hydrogen (a),

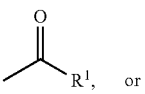

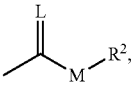

in which
L represents oxygen and
M represents oxygen or sulphur,
$R^1$ represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine; or represents cyclopropyl, cyclopentyl or cyclohexyl;
represents phenyl which is optionally monosubstituted by fluorine, chlorine, bromine, cyano, nitro, methyl, methoxy, trifluoromethyl or trifluoromethoxy; or
represents furanyl, thienyl or pyridyl, each of which is optionally monosubstituted by chlorine or methyl,
$R^2$ represents $C_1$-$C_8$-alkyl, $C_2$-$C_6$-alkenyl or $C_1$-$C_2$-alkoxy-$C_2$-$C_3$-alkyl;
represents cyclopentyl or cyclohexyl; or
represents phenyl or benzyl, each of which is optionally monosubstituted by fluorine, chlorine, cyano, nitro, methyl, methoxy, trifluoromethyl or trifluoromethoxy.

6. A compound of formula (I) according to claim 1 in which
W represents hydrogen or methyl,
X represents chlorine or methyl,
Y in the 5-position represents the radical

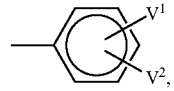

Z in the 4-position represents hydrogen or methyl,
$V^1$ represents fluorine, chlorine, methyl, methoxy, trifluoromethyl or trifluoromethoxy,
$V^2$ represents hydrogen, fluorine, chlorine, methyl, methoxy or trifluoromethyl,
A represents —$CH_2$—, —$CHCH_3$— or —$CH_2$—$CH_2$—,
B represents hydrogen, methyl, ethyl, propyl, isopropyl, $C_2$-$C_4$-alkenyl, methoxy, ethoxy, propoxy, isopropoxy, butoxy, or isobutoxy; or represents phenyl which is optionally mono- or disubstituted by fluorine, chlorine, bromine, methyl, methoxy, trifluoromethyl, trifluoromethoxy, cyano or nitro,
$Q^1$ represents hydrogen or methyl,
$Q^2$ represents hydrogen or methyl,
G represents hydrogen (a),

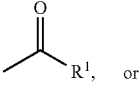

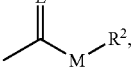

in which
L represents oxygen and
M represents oxygen or sulphur,

R¹ represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine; represents cyclopropyl, cyclopentyl or cyclohexyl;

represents phenyl which is optionally monosubstituted by fluorine, chlorine, bromine, cyano, nitro, methyl, methoxy, trifluoromethyl or trifluoromethoxy; or represents furanyl, thienyl or pyridyl, each of which is optionally monosubstituted by chlorine or methyl, R² represents $C_1$-$C_8$-alkyl, $C_2$-$C_6$-alkenyl or $C_1$-$C_2$-alkoxy-$C_2$-$C_3$-alkyl;

represents cyclopentyl or cyclohexyl;

or represents phenyl or benzyl, each of which is optionally monosubstituted by fluorine, chlorine, cyano, nitro, methyl, methoxy, trifluoromethyl or trifluoromethoxy.

7. A compound of formula (I) according to claim 1, in which

W represents hydrogen, methyl, ethyl, chlorine or bromine,

X represents chlorine, bromine, methyl, ethyl, propyl, methoxy, ethoxy, propoxy, $H_3CO$—$(CH_2)_2$—O, cyclopropylmethoxy, trifluoromethyl or difluoromethoxy, Y in the 4-position represents methyl, Z represents hydrogen, A represents —$CH_2$—, —$CHCH_3$— or —$CH_2$—$CH_2$—, B represents hydrogen, methyl, ethyl, propyl, isopropyl, $C_2$-$C_4$-alkenyl, methoxy, ethoxy, propoxy, isopropoxy, butoxy, or isobutoxy; represents phenyl which is optionally mono- or disubstituted by fluorine, chlorine, bromine, methyl, methoxy, trifluoromethyl, trifluoromethoxy, cyano or nitro; represents cyclopropyl; or represents cyclopentyl or cyclohexyl in which optionally one methylene group is replaced by oxygen, Q¹ represents hydrogen or methyl, Q² represents hydrogen or methyl, G represents hydrogen (a),

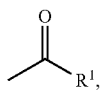

(b)

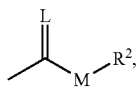

(c)

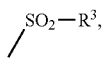

(d)

in which

L represents oxygen or sulphur and

M represents oxygen or sulphur,

R¹ represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine; represents cyclopropyl, cyclopentyl or cyclohexyl;

represents phenyl which is optionally monosubstituted by fluorine, chlorine, bromine, cyano, nitro, methyl, methoxy, trifluoromethyl or trifluoromethoxy;

represents

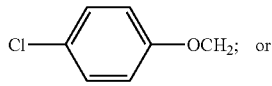

represents furanyl, thienyl or pyridyl, each of which is optionally monosubstituted by chlorine or methyl, R² represents $C_1$-$C_{10}$-alkyl, $C_2$-$C_{10}$-alkenyl or $C_1$-$C_2$-alkoxy-$C_2$-$C_4$-alkyl;

represents cyclopentyl or cyclohexyl;

or represents phenyl or benzyl, each of which is optionally monosubstituted by fluorine, chlorine, cyano, nitro, methyl, methoxy, trifluoromethyl or trifluoromethoxy, and R³ represents methyl or methyl-substituted phenyl.

8. A compound of formula (I) according to claim 1 in which

W represents hydrogen, methyl, chlorine or bromine,

X represents chlorine, bromine, methyl, methoxy or trifluoromethyl,

Y in the 4-position represents hydrogen, chlorine, bromine or methyl,

Z in the 3- or 5-position represents chlorine, bromine, methyl, ethyl, trifluoromethyl or trifluoromethoxy, A represents —$CH_2$—, —$CHCH_3$— or —$CH_2$—$CH_2$—, B represents hydrogen, methyl, ethyl, propyl, isopropyl, $C_2$-$C_4$-alkenyl, methoxy, ethoxy, propoxy, isopropoxy, butoxy, isobutoxy, or cyclopropyl; or represents phenyl which is optionally mono- or disubstituted by fluorine, chlorine, bromine, methyl, methoxy, trifluoromethyl, trifluoromethoxy, cyano or nitro, Q¹ represents hydrogen or methyl, Q² represents hydrogen or methyl, G represents hydrogen (a),

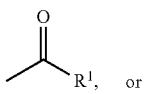

(b)

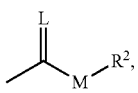

(c)

in which

L represents oxygen and

M represents oxygen or sulphur,

R¹ represents $C_1$-$C_6$-alkyl, $C_2$-$C_6$-alkenyl, $C_1$-$C_2$-alkoxy-$C_1$-$C_2$-alkyl, or $C_1$-$C_2$-alkylthio-$C_1$-$C_2$-alkyl each of which is optionally mono- to trisubstituted by fluorine or chlorine; represents cyclopropyl, cyclopentyl or cyclohexyl;

represents phenyl which is optionally monosubstituted by fluorine, chlorine, bromine, cyano, nitro, methyl, methoxy, trifluoromethyl or trifluoromethoxy; or represents furanyl, thienyl or pyridyl, each of which is optionally monosubstituted by chlorine or methyl, R² represents $C_1$-$C_8$-alkyl, $C_2$-$C_6$-alkenyl or $C_1$-$C_2$-alkoxy-$C_2$-$C_3$-alkyl;

represents cyclopentyl or cyclohexyl;

or represents phenyl or benzyl, each of which is optionally monosubstituted by fluorine, chlorine, cyano, nitro, methyl, methoxy, trifluoromethyl or trifluoromethoxy.

9. A composition comprising an effective amount of an active compound combination comprising, (a') at least one compound of formula (I) according to claim 1, and (b') at least one compound which improves crop plant tolerance and which is selected from the group consisting of:

4-dichloroacetyl-1-oxa-4-azaspiro[4.5]decane (AD-67, MON-4660), 1-dichloro-acetylhexahydro-3,3,8a-trimethylpyrrolo[1,2-a]pyrimidin-6(2H)one(dicyclonon, BAS-145138), 4-dichloroacetyl-3,4-dihydro-3-methyl-2H-1,4-benzoxazine(benoxacor), 1-methylhexyl 5-chloro-quinolin-8-oxyacetate(cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methyl-phenyl)urea (daimuron, dymron), 3,6-dichloro-2-methoxybenzoic acid(dicamba), S-1-methyl-1-phenylethyl piperidine-1-thiocarboxylate(dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenyl-pyrimidine (fenclorim), ethyl 1-(2,4-dichlorophenyl)-5-trichloromethyl-1H-1,2,4-triazole-3-carboxylate (fenchlorazole-ethyl), phenylmethyl2-chloro-4-trifluoromethylthiazole-5-carboxylate(flurazole), 4-chloro-N-(1,3-dioxolan-2-ylmethoxy)-α-trifluoroacetophenone oxime(fluxofenim), 3-dichloroacetyl-5-(2-furanyl)-2,2-dimethyloxazolidine(furilazole, MON-13900), ethyl 4,5-dihydro-5,5-diphenyl-3-isoxazole-carboxylate(isoxadifen-ethyl), 1-(ethoxycarbonyl)ethyl-3,6-dichloro-2-methoxybenzoate(lactidichlor), (4-chloro-o-tolyloxy)acetic acid(MCPA), 2-(4-chloro-o-tolyloxy)propionic acid(mecoprop), diethyl 1-(2,4-dichlorophenyl)-4,5-dihydro-5-methyl-1H-pyrazole-3,5-dicarboxylate(mefenpyr-diethyl), 2-dichloromethyl-2-methyl-1,3-dioxolane(MG-191), 2-propenyl-1-oxa-4-azaspiro[4.5]decane4-carbodithioate(MG-838), 1,8-naphthalicanhydride, α-(1,3-dioxolan-2-ylmethoximino)phenylacetonitrile(oxabetrinil), 2,2-dichloro-N-(1,3-dioxolan-2-ylmethyl)-N-(2-propenyl) acetamide(PPG-1292), 3-dichloroacetyl-2,2-dimethyloxazolidine(R-28725), 3-dichloroacetyl-2,2,5-trimethyloxazolidine(R-29148), 4-(4-chloro-o-tolyl)butyric acid, 4-(4-chlorophenoxy)butyric acid, diphenyl methoxyacetic acid, methyl diphenylmethoxyacetate, ethyl diphenylmethoxyacetate, methyl1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl5-chloro-quinolin-8-oxyacetate, 4-allyloxybutyl 5-chloroquinolin-8-oxy-acetate, 1-allyloxyprop-2-yl 5-chloroquinolin-8-oxyacetate, methyl 5-chloroquinoxalin-8-oxyacetate, ethyl 5-chloroquinolin-8-oxy-acetate, allyl 5-chloroquinoxalin-8-oxyacetate, 2- oxo-prop-1-yl 5-chloroquinolin-8-oxyacetate, diethyl 5-chloroquinolin-8-oxy-malonate, diallyl 5-chloroquinoxalin-8-oxymalonate, diethyl 5-chloroquinolin-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea(N-(2-methoxybenzoyl)-4-[(methylaminocarbonyl) amino]-benzenesulphonamide), 1-[4-(N-2-methoxybenzoylsulphamoyl)-phenyl]-3,3-dimethylurea, 1-[4-(N-4,5-dimethylbenzoylsulphamoyl)-phenyl]-3-methylurea, 1-[4-(N-naphthylsulphamoyl)-phenyl]-3,3-dimethylurea, N-(2-methoxy-5-methylbenzoyl)-4-(cyclopropyl-aminocarbonyl)benzenesulphonamide, a compound of the general formula (IIa)

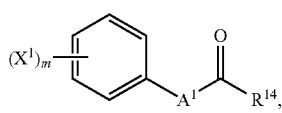

a compound of the general formula (IIb)

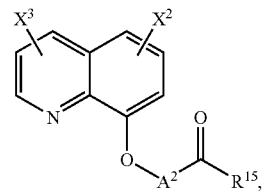

a compound of the general formula (IIc)

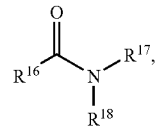

where
m represents a number 0, 1, 2, 3, 4 or 5,
$A^1$ represents one of the following divalent heterocyclic groups,

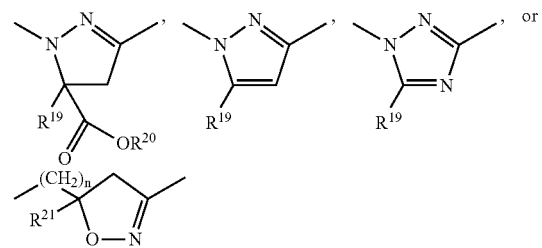

n represents a number 0, 1, 2, 3, 4 or 5,
$A^2$ represents alkanediyl having 1 or 2 carbon atoms which is optionally substituted by one or more of $C_1$-$C_4$-alkyl and/or $C_1$-$C_4$-alkoxycarbonyl and/or $C_1$-$C_4$-alkenyloxycarbonyl,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)amino,
$R^{16}$ represents $C_1$-$C_4$-alkyl which is optionally substituted by fluorine, chlorine or bromine,
$R^{17}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine, bromine and/or $C_1$-$C_4$-alkyl,
$R^{18}$ represents hydrogen; represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine; or represents phenyl which is optionally substituted by fluorine, chlorine, bromine and/or $C_1$-$C_4$-alkyl; or $R^{17}$ and $R^{18}$ together also represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle,
$R^{19}$ represents hydrogen, cyano, or halogen; or represents $C_1$-$C_4$-alkyl, $C_3$-$C_6$-cycloalkyl or phenyl, each of which is optionally substituted by fluorine, chlorine and/or bromine, $R^{20}$ represents hydrogen; or represents $C_1$-$C_6$-alkyl, $C_3$-$C_6$-cycloalkyl or tri($C_1$-$C_4$-alkyl)silyl, each of which is optionally substituted by hydroxyl, cyano, halogen or $C_1$-$C_4$-alkoxy, $R^{21}$ represents hydrogen, cyano, halogen; or represents $C_1$-$C_4$-alkyl, $C_3$-$C_6$-cycloalkyl or phenyl, each of which is optionally substituted by fluorine, chlorine and/or bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, a compound of the general formula (IId)

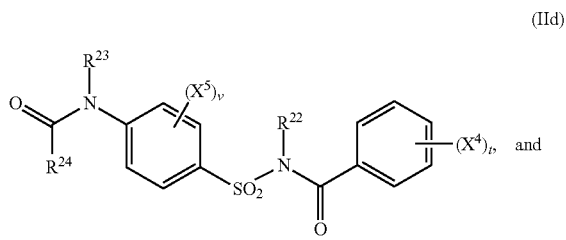

(IId)

a compound of the general formula (IIe)

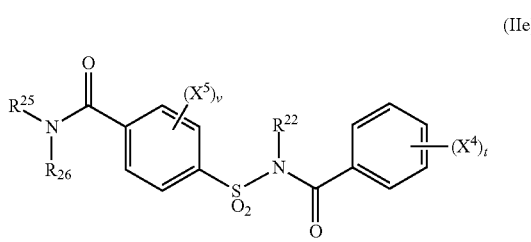

(IIe)

where
t represents a number 0, 1, 2, 3, 4 or 5,
v represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen; or represents $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, each of which is optionally substituted by cyano, halogen or $C_1$-$C_4$-alkoxy; or represents $C_3$-$C_6$-cycloalkyl, $C_3$-$C_6$-cycloalkyloxy, $C_3$-$C_6$-cycloalkylthio or $C_3$-$C_6$-cycloalkylamino, each of which is optionally substituted by cyano, halogen or $C_1$-$C_4$-alkyl, $R^{25}$ represents hydrogen; represents $C_1$-$C_6$-alkyl which is optionally substituted by cyano, hydroxyl, halogen or $C_1$-$C_4$-alkoxy; represents $C_3$-$C_6$-alkenyl or $C_3$-$C_6$-alkynyl, each of which is optionally substituted by cyano or halogen; or represents $C_3$-$C_6$-cycloalkyl which is optionally substituted by cyano, halogen or $C_1$-$C_4$-alkyl, $R^{26}$ represents hydrogen; represents $C_1$-$C_6$-alkyl which is optionally substituted by cyano, hydroxyl, halogen or $C_1$-$C_4$-alkoxy; represents $C_3$-$C_6$-alkenyl or $C_3$-$C_6$-alkynyl, each of which is optionally substituted by cyano or halogen; represents $C_3$-$C_6$-cycloalkyl which is optionally substituted by cyano, halogen or $C_1$-$C_4$-alkyl; or represents phenyl which is optionally substituted by nitro, cyano, halogen, $C_1$-$C_4$-alkyl, $C_1$-$C_4$-haloalkyl, $C_1$-$C_4$-alkoxy or $C_1$-$C_4$-haloalkoxy; or together with $R^{25}$ represents $C_2$-$C_6$-alkanediyl or $C_2$-$C_5$-oxaalkanediyl, each of which is optionally substituted by $C_1$-$C_4$-alkyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

10. A pesticide, herbicide or fungicide comprising at least one compound of formula (I) according to claim 1, and an extender.

11. A composition according to claim 9, in which the compound which improves cropplant tolerance is selected from the group consisting of:
cloquintocet-mexyl, fenchlorazole-ethyl, isoxadifen-ethyl, mefenpyr-diethyl, furilazole, fenclorim, cumyluron, dymron, a compound of the formula IIe-5

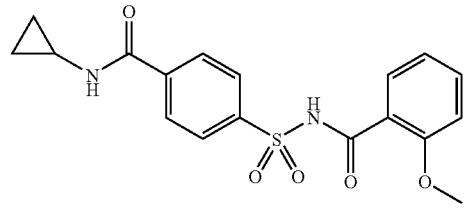

IIe-5 and a compound of the formula IIe-11

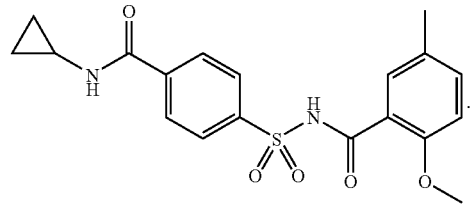

IIe-11

12. The compound of claim 1, having a structure according to Formula (I- 1a), (I-1b), (I-1c), or (I-1d):

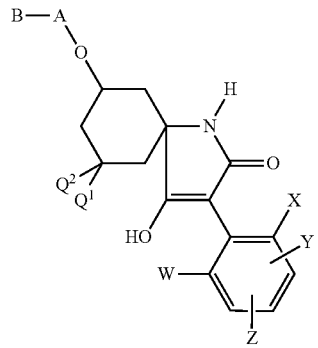

(I-1a)

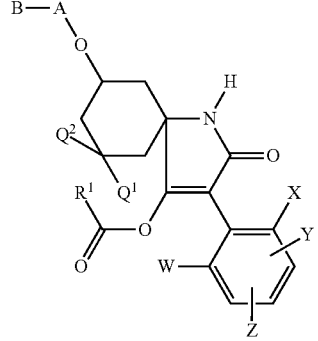

(I-1-b)

-continued (I-1-c)

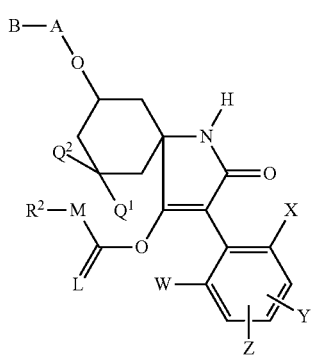

(I-1-d)

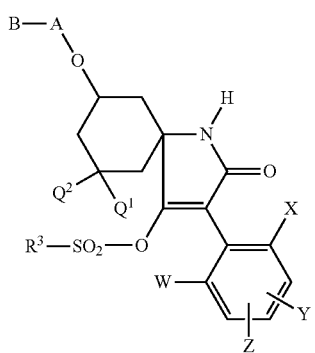

wherein A, B, L, M, $Q^1$, $Q^2$, W, X, Y, Z, $R^1$, $R^2$, and $R^3$ are defined as in claim 1.

13. The compound of claim 12 having a structure according to Formula (I-1a):

(I-1a)

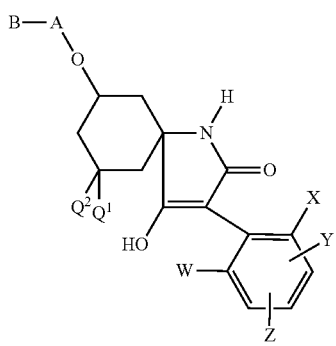

wherein
W, X, Y and Z are defined as in claim 1;
$Q^1$ and $Q^2$ are members independently selected from H and $CH_3$;
A is a member selected from —$CH_2$— and —$CH_2$—$CH_2$—; and
B is a member selected from H, $CH_3$, $C_2H_5$, $C_3H_7$, i-$C_3H_7$, $OCH_3$, $OC_2H_5$,

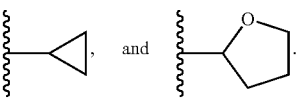

14. A compound having the formula:

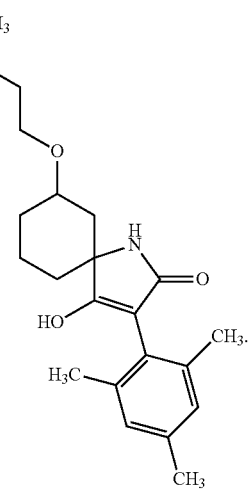

* * * * *